(12) United States Patent
Zhou et al.

(10) Patent No.: US 8,003,407 B2
(45) Date of Patent: Aug. 23, 2011

(54) LATERAL FLOW SYSTEM AND ASSAY

(75) Inventors: Siliang Zhou, Hayward, CA (US);
William Rutter, San Francisco, CA (US); Ning Liu, Sichuan (CN)

(73) Assignee: Relia Diagnostic Systems, LLC, San Francisco, CA (US)

( * ) Notice: Subject to any disclaimer, the term of this patent is extended or adjusted under 35 U.S.C. 154(b) by 571 days.

(21) Appl. No.: 11/572,568

(22) PCT Filed: Jul. 29, 2005

(86) PCT No.: PCT/US2005/027182
§ 371 (c)(1),
(2), (4) Date: Dec. 23, 2008

(87) PCT Pub. No.: WO2006/073500
PCT Pub. Date: Jul. 13, 2006

(65) Prior Publication Data
US 2009/0253119 A1 Oct. 8, 2009

Related U.S. Application Data

(60) Provisional application No. 60/592,202, filed on Jul. 29, 2004.

(51) Int. Cl.
*G01N 33/558* (2006.01)

(52) U.S. Cl. ........ 436/514; 422/401; 422/420; 422/421; 422/422; 422/424; 422/425; 422/426; 422/427; 422/429; 435/287.2; 435/287.7; 435/287.9; 435/805; 435/810; 435/970; 436/169; 436/518; 436/807; 436/810

(58) Field of Classification Search ........................ None
See application file for complete search history.

(56) References Cited

U.S. PATENT DOCUMENTS 4,340,482 A  7/1982 Sternberg
(Continued)

FOREIGN PATENT DOCUMENTS

CN   2484568   4/2002
(Continued)

OTHER PUBLICATIONS

Extended Search Report, European Patent Office, for PCT/US2005/027182 (corresponding National Phase Application filed with EPO), dated Apr. 15, 2008, 6 pages.
(Continued)

*Primary Examiner* — Chris L Chin
(74) *Attorney, Agent, or Firm* — Dennis A. Bennett; Suman R. Mirmira

(57) ABSTRACT

The present invention relates to a lateral flow assay and system, including a test strip, for detection and quantification of analytes in samples, such as samples containing cells and fluid. In general, according to the present invention, a test strip for a lateral flow assay for detection of at least one analyte in a sample comprises: (1) a chromatographic strip, a sample filter, a fluid-impermeable barrier, and means for providing a mobilizable detectable agent that is capable of binding to the at least one analyte or to the capture agent after capturing the analyte to the chromatographic strip such that the mobilizable detectable agent migrates through the chromatographic strip and contacts sample that has passed through the sample filter and also has migrated through the chromatographic strip. The test strip allows detection with or without quantitation of an analyte in a sample containing whole cells.

39 Claims, 23 Drawing Sheets

Port-1: Used for adding sample in indirect bilateral flow assay; used for adding sample or buffer in sandwich bilateral flow assay.

Port-2: Used for adding buffer in indirect bilateral flow assay; used for adding sample or buffer in sandwich bilateral flow assay.

U.S. PATENT DOCUMENTS

| | | | |
|---|---|---|---|
| 4,618,533 A | 10/1986 | Steuck | |
| 4,626,684 A | 12/1986 | Landa | |
| 4,703,017 A | 10/1987 | Campbell et al. | |
| 4,743,560 A | 5/1988 | Campbell et al. | |
| 4,816,224 A | 3/1989 | Vogel | |
| 4,822,566 A | 4/1989 | Newman | |
| 4,943,522 A | 7/1990 | Eisinger | |
| 5,028,535 A | 7/1991 | Buechler | |
| 5,037,736 A | 8/1991 | Freitag | |
| 5,049,487 A | 9/1991 | Phillips | |
| 5,089,391 A | 2/1992 | Buechler | |
| 5,096,837 A | 3/1992 | Fan | |
| 5,211,914 A | 5/1993 | Vogel | |
| 5,232,835 A | 8/1993 | Litman | |
| 5,234,813 A | 8/1993 | McGeehan | |
| 5,238,652 A | 8/1993 | Sun | |
| 5,240,862 A | 8/1993 | Koenhen | |
| 5,266,497 A | 11/1993 | Imai | |
| 5,300,779 A | 4/1994 | Hillman | |
| 5,344,754 A | 9/1994 | Zweig | |
| 5,356,785 A | 10/1994 | McMahon | |
| 5,384,264 A | 1/1995 | Chen et al. | |
| 5,413,939 A | 5/1995 | Gustafson | |
| 5,418,143 A | 5/1995 | Zweig | |
| 5,458,852 A | 10/1995 | Buechler | |
| 5,468,648 A | 11/1995 | Chandler | |
| 5,554,531 A | 9/1996 | Zweig | |
| 5,580,794 A | 12/1996 | Allen | |
| 5,589,399 A | 12/1996 | Allen et al. | |
| 5,602,040 A | 2/1997 | May et al. | |
| 5,650,334 A | 7/1997 | Zuk et al. | |
| 5,656,448 A | 8/1997 | Kang et al. | |
| 5,660,993 A | 8/1997 | Cathey et al. | |
| 5,679,526 A | 10/1997 | Buechler et al. | |
| 5,679,579 A | 10/1997 | Gustafson | |
| 5,712,172 A | 1/1998 | Huang et al. | |
| 5,726,010 A | 3/1998 | Clark | |
| 5,728,587 A | 3/1998 | Kang et al. | |
| 5,750,333 A | 5/1998 | Clark | |
| 5,753,517 A | 5/1998 | Brooks | |
| 5,766,552 A | 6/1998 | Doshi et al. | |
| 5,766,875 A | 6/1998 | Hafeman et al. | |
| 5,821,073 A | 10/1998 | Lee | |
| 5,824,268 A | 10/1998 | Bernstein | |
| 5,922,615 A | 7/1999 | Nowakowski et al. | |
| 5,939,272 A | 8/1999 | Buechler et al. | |
| 5,985,675 A | 11/1999 | Charm et al. | |
| 6,001,658 A | 12/1999 | Fredrickson | |
| 6,007,999 A | 12/1999 | Clark | |
| 6,136,610 A | 10/2000 | Polito et al. | |
| 6,139,757 A | 10/2000 | Ohmura et al. | |
| 6,187,598 B1 | 2/2001 | May et al. | |
| 6,284,194 B1 | 9/2001 | Chu | |
| 6,410,341 B1 | 6/2002 | Freitag et al. | |
| 6,524,864 B2 | 2/2003 | Fernandez Decastro | |
| 6,528,323 B1 | 3/2003 | Thayer et al. | |
| 6,541,277 B1 | 4/2003 | Kang et al. | |
| 6,551,842 B1 | 4/2003 | Carpenter | |
| 6,602,719 B1 | 8/2003 | Carpenter | |
| 6,617,116 B2 | 9/2003 | Guan | |
| 6,713,308 B1 | 3/2004 | Lu et al. | |
| 6,737,278 B1 | 5/2004 | Carlsson et al. | |
| 6,753,190 B1 | 6/2004 | Okada et al. | |
| 6,766,817 B2 | 7/2004 | da Silva | |
| 6,767,710 B2 | 7/2004 | DiNello | |
| 6,815,160 B1 | 11/2004 | Chien et al. | |
| 6,818,627 B1 | 11/2004 | Mahalingam et al. | |
| 6,918,404 B2 | 7/2005 | Dias da Silva | |
| 6,951,924 B2 | 10/2005 | Rosen et al. | |
| 7,066,586 B2 | 6/2006 | da Silva | |
| 7,229,839 B2 | 6/2007 | Thayer | |
| 7,270,995 B2 | 9/2007 | Matsushita | |
| 7,285,255 B2 | 10/2007 | Kadlec et al. | |
| 7,297,529 B2 | 11/2007 | Polito | |
| 7,309,611 B2 | 12/2007 | DiNello | |
| 7,521,196 B2 | 4/2009 | Dinello | |
| 7,605,004 B2 | 10/2009 | Zhou | |
| 2004/0018637 A1 | 1/2004 | Polito | |
| 2004/0096356 A1 | 5/2004 | Degelaen | |
| 2007/0283747 A1 | 12/2007 | DiNello | |
| 2008/0031779 A1 | 2/2008 | Polito | |
| 2009/0253119 A1 | 10/2009 | Zhou | |
| 2009/0257915 A1 | 10/2009 | DiNello | |
| 2010/0092945 A1 | 4/2010 | Zhou | |
| 2010/0099112 A1 | 4/2010 | Zhou | |

FOREIGN PATENT DOCUMENTS

| | | |
|---|---|---|
| EP | 322340 | 6/1989 |
| GB | 2204398 | 11/1988 |
| WO | 8809499 A1 | 12/1988 |
| WO | 9113998 | 9/1991 |
| WO | 9209892 A1 | 6/1992 |
| WO | 9212428 | 7/1992 |
| WO | 9303176 | 2/1993 |
| WO | 9428414 A1 | 12/1994 |
| WO | 9516914 A1 | 6/1995 |
| WO | 9607101 | 3/1996 |
| WO | 9622533 | 7/1996 |
| WO | 9707993 | 3/1997 |
| WO | 9708551 | 3/1997 |
| WO | 9709620 A1 | 3/1997 |
| WO | 9737222 | 10/1997 |
| WO | 9821587 A1 | 5/1998 |
| WO | 9827435 | 6/1998 |
| WO | 9918439 | 4/1999 |
| WO | 9940438 A1 | 8/1999 |
| WO | 0058730 | 10/2000 |
| WO | 0062060 | 10/2000 |
| WO | 03008933 | 1/2003 |

OTHER PUBLICATIONS

Office Action for corresponding EP National Phase Application, European Patent Convention, dated Apr. 17, 2009, 2 pages.

Notice of Allowance for corresponding EP National Phase Application, European Patent Convention, dated Feb. 18, 2010, 139 pages (including allowed claims).

Notice of First Office Action, Intellectual Property Office of the People's Republic of China for the corresponding National Phase Application filed in China, dated Sep. 13, 2010, 9 pages.

Birnbaum, Staffan et al; Latex-Based Thin-Layer Immunoaffinity chromatography for Quantitation of Protein Analytes; Anal. Biochem 206(1) 168-171 (1992); Academic Press Inc. 30 Corporate Dr., Ste. 400, Burlington, MA, United States.

Chamow, Steven et al; Immunoadhesins: Principles and Applications; Trends Biotech. 14(2) 52-60 (1996); Elsevier Science Ltd, 6277 Sea Harbor Drive Orlando, Fl 32887-4800 USA.

Fu, Guohui et al; Purification and Characterization of the Human Erythrocyte Band 3 Protein C-terminal Domain; Biochem 43 (6) 1633-1638 (2004) American Chemical Society 1155 16th Street NW Washington, DC 20036.

Goldstein, IJ et al; What should be called a lectin?; Nature, 285 66 (1980); Palgrave Macmillan Ltd., Houndmills, Basingstoke, Hampshire, RG21 6XS, England.

Hayes, Fred et al; Simultaneous Immunoassay Using Electrochemical Detection of Metal Ion Labels; Anal Chem, 66 (11) 1860-1865 (1994); American Chemical Society 1155 16th Street NW Washington, DC 20036.

Holliger, Philip et al; Artificial antibodies and Enzymes: Mimicking Nature and Beyond; Trends Biotech 13 (1) 7-9 (1995); Elsevier Science Ltd, 6277 Sea Harbor Drive Orlando, FL 32887-4800 USA.

Klimov, Alex et al; Improved Immunochromatographic Format for Competitive-Type Assays; Clin Chem 41;1360 (1995); American Association for Clinical Chemistry, 1850 K Street, NW Suite 625 Washington, DC 20006.

McNeil, C. J., et al, Electrochemical sensors based on impedance measurement of enzyme-catalyzed polymer dissolution: theory and applications, Analytical Chemistry, American Chem. Soc., Columbus, US, vol. 67, No. 21, Nov. 1, 1995, pp. 3928-3935.

Roberts, Matthew et al; Investigation of Liposome-Based Immunomigration Sensors for the Detection of Polychlorinated Biophenyls; Anal Chem. (67) 482-491 (1995); American Chemical Society 1155 16th Street NW Washington, DC 20036.

Schnebli, H.P. et al; Reaction of Lectins with Human Erythrocytes. I. Factors Governing the Agglutination Reaction; Exp Cell Res. 91 (1) 175-183 (1975); Academic Press Inc. 30 Corporate Dr., Ste. 400, Burlington, MA, United States.

Stephenson, Joanne; RAMP: A Quantitative Immunoassay Platform Takes Shape; IVD Technology 51 (1998); Canon Communications. 11444 W. Olympic Blvd. Los Angeles, CA 90064.

Van Oudheusden, A.P.M. et al; A Multilayer Membrane System for Blood Plasma Isolation for use in Primary Health Care; Ann Clin Biochem. 28 (Pt. 1) 55-59 (1991); Association for Clinical Biochemistry, 130-132 Tooley St, London SE1 2TU.

Wang, Da Neng; Band 3 Protein: Structure, Flexibility and Function; FEBS Letter 346 (1) 26-31 (1994); FEBS Federation of European Biochemical Societies.

Young, Mark et al; Distinct Regions of Human Glycophorin A Enhance Human Red Cell Anion Exchanger (Band 3; AE1) Transport Function and Surface Trafficking; Biol Chem. 278 (35) 32954-61 (2003); American Society for Biochemistry and Molecular Biology, Inc., Bethesda, MD, 20814.

Biosite Diagnostics, Inc., Triage Drugs of Abuse Panel, website: www.biosite.com/products/doa/doa.html, retrieved Feb. 23, 1999. (Previously submitted for U.S. Appl. No. 10/346,683).

Biosite Diagnostics, Inc., Triage C. Difficile Panel, website: www.biosite.com/products/cdiff/cdifficile.html, retrieved Feb. 23, 1999. (Previously submitted for U.S. Appl. No. 10/346,683).

Biosite Diagnostics, Inc., Triage Parasite Panel, webiste: www.biosite.com/products/parasite/parasite.html, retrieved Feb. 23, 1999. (Previously submitted for U.S. Appl. No. 10/346,683).

Biosite Diagnostics, Inc., Triage Cardiac System, website: www.biosite.com/cardiac/cardsystem.html, retrieved Feb. 23, 1999. (Previously submitted for U.S. Appl. No. 10/346,683).

Port-1: Used for adding sample in indirect bilateral flow assay; used for adding sample or buffer in sandwich bilateral flow assay.

Port-2: Used for adding buffer in indirect bilateral flow assay; used for adding sample or buffer in sandwich bilateral flow assay.

Side View of Strip with Blood Filter in Port-1

For HIV, HCV antibody indirect assay, blood applied on Port-1

Side View of Strip with Blood Filter in Port-2

For HBsAg, Syphilis antibody Sandwich Assay, blood applied in Port-2

Side View of Strip with Blood Filter in Port-2

For PSA, TSH Sandwich Assay, blood applied in both Port-1 and Port-2

1. (24a) means a double-sided adhesive tape, which could be totally situated under (12a) or partly extended toward (10).

2. This figure could be applied to FIG. 2, 4, 9, and 11.

3. The function of (24a) here is to prevent liquid from flowing in the direction from (12a) to (10a) and to ensure the liquid flowing in the direction of (11a) in the first direction of flow when sample or buffer is added to Port-1.

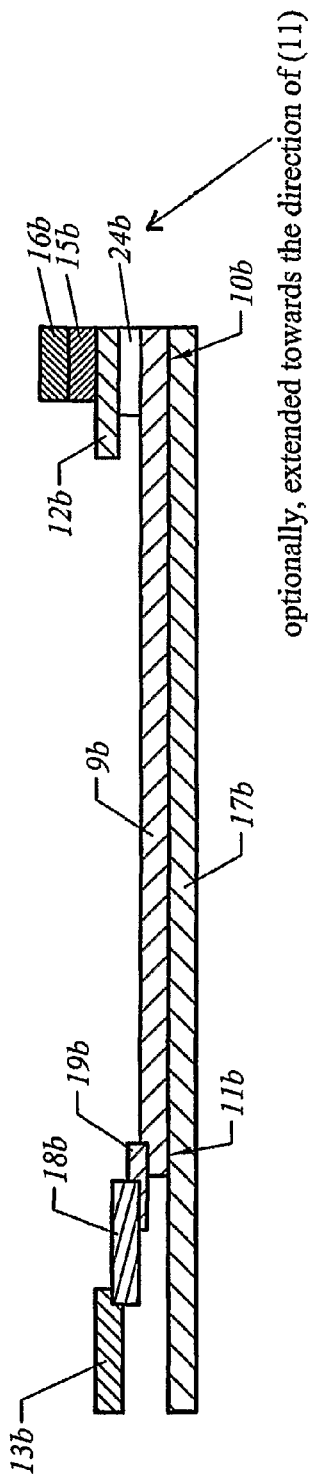

FIG. 13

1. (23b) means a double-sided adhesive tape, which could be totally situated under (12b) or partly extended toward (10b).

2. This figure could be applied to FIG. 3, 8, and 10.

3. The function of (24b) here is to prevent liquid from flowing in the direction from (12b) to (10b) and to ensure the liquid flowing in the direction of (11a) in the first direction of flow when sample or buffer is added to Port-1. Because the capillary rise of (9b) is much higher than that of (15b), the sample or buffer will flow in the direction of (11b) rather than in the direction of (15b).

LATERAL FLOW SYSTEM AND ASSAY

CROSS-REFERENCE TO RELATED APPLICATIONS

This application hereby claims priority from PCT Application Serial No. PCT/US05/19348, filed Jun. 2, 2005 by Zhou, et al. and entitled "Quantitative Lateral Flow System and Assay," as well as from U.S. Provisional Application Ser. No. 60/592,202, filed Jul. 29, 2004 by Zhou, et al. and also entitled "Quantitative Lateral Flow System and Assay." The disclosures of these two prior applications are hereby incorporated herein in their entirety by this reference.

TECHNICAL FIELD

This application generally relates to a qualitative and quantitative assay and system for detecting the presence of at least one analyte in biological samples, particularly samples that contain whole blood, red blood cells, white blood cells, or other cell types, and determining or quantifying the amount of the at least one analyte present.

BACKGROUND OF THE INVENTION

Many have tried to design a lateral flow assay for determining the presence and quantity of analytes in biological samples, such as blood samples that contain whole blood, red blood cells, or white blood cells, but have failed. The reasons for failure are many but may be attributable primarily to factors such as hemolysis of the red blood cells creating high background noise, low filtering efficiency, for example, resulting in leakage of the red blood cells onto the chromatographic strip, requirement for a relatively large sample volume (such as requiring 100 µl of sample or more), low efficiency in dissolving a conjugate or detectable agent, volume variation because of variation in cell volume when cells are present and long assay time. It would be desirable to design a lateral flow assay and system that can overcome one or more of these problems in the prior art.

In addition, it would be desirable to simplify the structure of the test strips for lateral flow assays to improve efficiency of the assay and to reduce manufacturing cost.

U.S. Pat. No. 6,136,610 to Polito et al. describes a method and apparatus for performing a lateral flow assay. U.S. Pat. No. 6,528,323 to Thayer et al. describes a bidirectional lateral flow test strip and method for conducting a lateral flow assay. While the methods and system described in these patents are useful for detecting and quantifying most analytes, these patents do not teach how the methods and system can be used to analyze samples containing cells, including red blood cells and/or white blood cells or other cell types. PCT Published Patent Application No. WO 03/008933 describes a test strip for conducting a lateral flow assay for a sample containing whole cells. However, the test strip in WO 03/008933 can be improved to simplify the structure, improve efficiency, reliability, reduce volume dependency and reduce manufacturing cost.

Different strategies have been applied to remove cells, such as red blood cells, from samples, such as blood samples, for detection of analytes, such as infectious disease organisms or antibodies to the infectious disease organisms. However, until now, few strategies have worked well. For example, U.S. Pat. No. 5,766,552 to Doshi et al. discloses the use of a porous material such as an absorbent pad which contains a mixture of both free agglutinating agents and particle-associated agglutinating agents intimately associated with nucleating particles. This filtering system requires about 100 µl of whole blood as shown in FIG. 4 therein.

Human erythrocytes contain on their cell surfaces several transelement proteins that may be suitable targets for making antibodies to red blood cells. For example, Band 3 is associated with the electroneutral exchange of chloride and bicarbonate across the cell element. Band 3 is a 911 amino acid glycoprotein having a 43 kDa amino-terminal cytosolic domain that binds the cytoskeleton, hemoglobin and glycolytic enzymes, and a 52 kDa carboxyl-terminal element domain that mediates anion transport, as described in Wang, D. N. (1994).

Two peptides of Band 3 have been purified, C1 containing Ala893-Val911 and KS4 containing Gly647-Arg656, as described in Fu, G. et al. (2004). The C1 peptide was found to contain protease activity, cleaving glycophorin A (GPA) at Leu118-Ser 19 in a dose-dependent manner, but the KS4 peptide did not cleave GPA under the same conditions.

Human erythrocytes further contain on their cell surface another protein, glycophorin. Glycophorin A (GPA) has been reported to enhance the expression of Band 3 anion transport activity at the cell surface of *Xenopus oocytes*. Young, M. T. and Tanner, M. J. (2003). The authors found that the C-terminal cytoplasmic tail of GPA enhanced trafficking of Band 3 to the cell surface, whereas the extracellular residues 68-70 increased the specific anion transport activity of Band 3.

Up to the present, there is lacking a rapid, effective and efficient quantitative lateral flow assay and system that can be used for determination of analytes in biological samples, such as in a blood sample, in a point-of-care setting, or a lateral flow assay and system that can be used for determination of analytes that are present in a small volume of sample, such as from a finger prick, or a lateral flow assay and system that can be used for determination of analytes that is volume independent, or that would address other problems in the prior art lateral flow assays and systems.

SUMMARY OF THE INVENTION

It is, therefore, one of the objects of the present invention to provide solutions to the problems faced by the prior art lateral flow assays and systems for determination of analytes in biological samples, including but not limited to samples containing cells, such as red blood cells or white blood cells, or other cell types.

It is another one of the objects of the present invention to provide a lateral flow assay and system, including a test strip and/or a cassette for holding the test strip, that can detect one or more analytes in a sample quantitatively.

It is another one of the objects of the present invention to provide a lateral flow assay and system as above that is relatively volume independent as compared to prior art assays or systems.

It is another one of the objects of the present invention to provide a lateral flow assay and system as above that can be performed using samples of small volumes, such as in the range of less than about 100 µl. Alternatively, the sample volume is less than about 90 µl, less than about 80 µl, less than about 70 µl, less than about 60 µl, less than about 50 µl, or is about 40 µl.

It is a further one of the objects of the present invention to provide a lateral flow assay and system as above that is efficient in dissolving the conjugate or detectable agent.

It is yet another one of the objects of the present invention to provide a lateral flow assay and system as above that provides good filtering for cells, such as red blood cells.

In accordance to one of the objects of the invention, there is provided an invention as follows.

In general, one embodiment of the invention comprises a test strip for a lateral flow assay for detection of at least one analyte in a sample containing a fluid comprising:

(1) a first element, wherein the first element comprises a sample filter and the sample filter comprises a first pore size and, optionally, a first agglutinating agent;

(2) optionally, a second element, wherein the second element comprises a first fluid collector and the first fluid collector comprises a second pore size, wherein the second element, if present, is in capillary contact with the first element;

(3) optionally, a third element, wherein the third element comprises a conjugate pad and the conjugate pad, if present, is in capillary contact, directly or indirectly, with the chromatographic strip, and wherein the conjugate pad comprises at least one mobilizable detectable agent, and the at least one mobilizable detectable agent is a first mobilizable detectable agent;

(4) a fourth element, wherein the fourth element comprises a chromatographic strip that comprises a first end and a second end, at least one capture band, at least one control band that optionally comprises a control agent and, optionally, at least one mobilizable detectable agent, wherein the at least one mobilizable detectable agent is a second mobilizable detectable agent, wherein the at least one capture band comprises an immobilized capture agent for capturing the at least one analyte, wherein the chromatographic strip allows lateral flow of fluid from the first end to the second end and/or from the second end to the first end, and wherein the chromatographic strip is in capillary contact with at least one of the first, second or third element, directly or indirectly;

(5) optionally, a fifth element comprising a buffer pad for application of sample, buffer, or reagent, wherein the fifth element, if present, is in capillary contact with the fourth element and optionally comprises a second agglutinating agent;

(6) a sixth element, wherein the sixth element comprises a first absorbent pad, and the first absorbent pad is in capillary contact with the chromatographic strip directly or indirectly;

(7) optionally, a seventh element, wherein the seventh element comprises a second absorbent pad, and the second absorbent pad, if present, is in capillary contact with the sixth element; and (8) optionally, an eighth element, wherein the eighth element comprises a second fluid collector, and the second fluid collector, if present, is in capillary contact with the fourth element and the fifth element, if present; and wherein the test strip is configured to allow detection with or without quantitation of the at least one analyte in the sample, and the sample contains red blood cells.

The test strip can comprise the second element and the ratio of the second pore size to the first pore size can be less than about 20 and is greater than about 1.

In one alternative, the test strip comprises the second element and at least a portion of the first element is situated on top of the second element.

In another alternative, the test strip comprises the second element and the conjugate pad, and the first element is in capillary contact with the conjugate pad through the second element but does not physically touch the conjugate pad.

In still another alternative, the test strip comprises the fifth element, and the fifth element comprises a second agglutinating agent.

In yet another alternative, the first absorbent pad is in capillary contact with the fifth element, directly or indirectly.

Another embodiment of the invention comprises a test strip for a lateral flow assay for detection of at least one analyte in a sample containing a fluid comprising:

(1) a first element comprising a sample filter, wherein the sample filter optionally comprises an agglutinating agent;

(2) a second element comprising a chromatographic strip, wherein the chromatographic strip includes a first end and a second end, at least one capture band that comprises an immobilized capture agent for capturing the at least one analyte, at least one control band and, optionally, a first mobilizable detectable agent, wherein the chromatographic strip supports lateral flow of fluid from the first end to the second end and/or from the second end to the first end, and wherein the chromatographic strip is in capillary contact with the sample filter;

(3) optionally, a third element comprising a conjugate pad, wherein the conjugate pad comprises a second mobilizable detectable agent, and the conjugate pad, if present, is in capillary contact with the chromatographic strip;

(4) a fourth element comprising a buffer pad, wherein the buffer pad is in capillary contact with the conjugate pad or the chromatographic strip;

(5) a fifth element comprising a first absorbent pad;

(6) optionally, a sixth element comprising a second absorbent pad; and (7) optionally, a seventh element comprising a first fluid collector;

wherein the test strip is configured to allow detection with or without quantitation of the at least one analyte in the sample, and the sample contains red blood cells.

Yet another embodiment of the invention comprises a test strip for a lateral flow assay for detection of at least one analyte in a sample comprising:

(1) a chromatographic strip having a first end and a second end, the test strip including a capture band for capturing the analyte;

(2) a fluid-transmitting element in operable contact with the first end of the chromatographic strip, the fluid-transmitting element being selected from the group consisting of a sample pad and a first sample filter, the fluid-transmitted element being located so that fluid applied to the fluid-transmitting element passes through the fluid-transmitting element and is applied to the chromatographic strip;

(3) at least one absorbent pad in operable contact with the fluid-transmitting element;

(4) optionally, a conjugate pad in operable contact with the second end of the chromatographic strip, the conjugate pad including a labeled specific binding partner for the analyte;

(5) a fluid collector in operable contact with either the conjugate pad, if present, or with the second end of the chromatographic strip, if the conjugate pad is not present, so that fluid applied to the fluid collector passes through the fluid collector to the conjugate pad, if present, or to the second end of the chromatographic strip if the conjugate pad is not present;

(6) a second sample filter in operable contact with the fluid collector so that liquid passing through the second sample filter is applied to the fluid collector; and (7) optionally, a backing in contact with one side of the chromatographic strip, the backing being situated so that fluid can pass unimpeded from the fluid-transmitting element in operable contact with the first end of the chromatographic strip and from the fluid collector or conjugate pad in operable contact with the second end of the chromatographic strip into the chromatographic strip.

Yet another embodiment of the invention comprises a test strip for a lateral flow assay for detection of at least one analyte in a sample comprising:

(1) a chromatographic strip having a first end and a second end, the test strip including a capture band for capturing the analyte;

(2) a first sample filter in operable contact with the first end of the chromatographic strip, the first sample filter being located so that fluid applied to the first sample filter passes through the first sample filter and is applied to the chromatographic strip;

(3) at least one absorbent pad in operable contact with at least part of the first sample filter so that the at least one absorbent pad can withdraw fluid from the chromatographic strip at the first end of the chromatographic strip, the fluid being drawn back through the sample filter;

(4) optionally, a conjugate pad in operable contact with the second end of the chromatographic strip, the conjugate pad comprising a mobilizable labeled specific binding partner for the analyte;

(5) a fluid collector in operable contact with either the conjugate pad, if present, or with the second end of the chromatographic strip, if the conjugate pad is not present, so that fluid applied to the fluid collector passes through the fluid collector to the conjugate pad, if present, or to the second end of the chromatographic strip if the conjugate pad is not present;

(6) a second sample filter in operable contact with the fluid collector so that liquid passing through the second sample filter is applied to the fluid collector; and (7) optionally, a backing in contact with one side of the chromatographic strip, the backing being situated so that fluid can pass unimpeded from the first sample filter in operable contact with the first end of the chromatographic strip and from the fluid collector or conjugate pad in operable contact with the second end of the chromatographic strip into the chromatographic strip.

Yet another embodiment of the invention comprises a test strip for a lateral flow assay for detection of at least one analyte in a sample comprising:

(1) a chromatographic strip comprising a first end and a second end, at least one capture band comprising an immobilized capture agent for capturing the at least one analyte, and at least one control band comprising an immobilized control agent;

(2) a conjugate pad, wherein the conjugate pad is in capillary contact with the second end of the chromatograph strip, and wherein the conjugate pad comprises a mobilizable detectable agent that is capable of binding to the at least one analyte or to the capture agent after capturing the analyte;

(3) a sample filter that is adjacent to the conjugate pad on the side closer to the second end, wherein the sample filter optionally comprises an agglutinating agent, and the sample filter is in capillary contact with the chromatographic strip;

(4) optionally a fluid collector that, if present, is situated between the sample filter and the chromatographic strip;

(5) optionally, a buffer pad situated at the first end of the chromatographic strip and is in capillary contact with the chromatographic strip;

(6) a first absorbent pad situated at the first end of the chromatographic strip that is in capillary contact with the chromatographic strip, either directly or indirectly; and (7) optionally, a second absorbent pad that, if present, is in capillary contact with the first absorbent pad; wherein the test strip allows detection with or without quantitation of an analyte in a sample containing whole cells.

A group of embodiments of the present invention is embodiments in which a fluid-impermeable barrier is placed at least partially between any fluid-transmitting element in operable contact with the first end of the chromatographic medium and the chromatographic medium so that fluid passing from the fluid-transmitting element is temporarily prevented from flowing in a direction toward the first end of the chromatographic medium by forcing the fluid to flow under the impermeable barrier to reach the first end of the chromatographic medium. This improves the sensitivity of the assay. The barrier can be present in various arrangements that accomplish this, such as being flush with the first end or being near to the first end.

In general, one embodiment of the invention employing a fluid-impermeable barrier comprises a test strip for a lateral flow assay for detection of at least one analyte in a sample, comprising:

(1) a chromatographic strip comprising a first end and a second end;

(2) at least one capture band situated on the chromatographic strip, wherein the capture band comprises an immobilized capture agent for capturing the at least one analyte;

(3) at least one control band, optionally comprising an immobilized control agent;

(4) a first sample filter in capillary contact with the first end of the chromatographic strip, where the first sample filter optionally comprises an agglutinating agent for agglutinating cells in the sample;

(5) a fluid-impermeable barrier wherein the barrier is in direct physical contact with the first end of the chromatographic strip, and is situated at least partially under the sample filter, whereby fluid flow from the sample filter to the chromatographic strip is substantially slowed by forcing the fluid to flow underneath the impermeable barrier to reach the first end of the strip; and (6) means for providing a mobilizable detectable agent that is capable of binding to the at least one analyte or to the capture agent; and (7) means for absorbing excess fluid; wherein the test strip allows detection with or without quantitation of an analyte in a sample containing whole cells.

In another embodiment of the invention, there is provided a test strip as above, where the means for providing a mobilizable detectable agent comprises a conjugate pad, where the conjugate pad retains the mobilizable detectable agent until fluid is added to the conjugate pad to release the mobilizable detectable agent.

In yet another embodiment, there is provided a test strip as above, further comprising a buffer pad. In one aspect of this invention, the buffer pad is situated at or near the second end of the chromatographic strip and is in direct physical contact with the conjugate pad.

In a further embodiment, there is provided a test strip as one or more of the above, further comprising a first absorbent pad. In one aspect of the invention, the first absorbent pad is situated at or near the first end of the chromatographic strip and is in direct physical contact with the chromatographic strip.

In yet another embodiment of the present invention, there is provided a test strip as above, further comprising a second absorbent pad. In one aspect of the invention, the second absorbent pad is in capillary contact with the first absorbent pad or the chromatographic strip.

In a further embodiment of the invention there is provided a test strip as one or more of the above, further comprising a second sample filter. In one aspect of the invention, the second sample filter optionally comprises an agglutinating agent. In another aspect of the invention, the second sample filter is in capillary contact with the chromatographic strip, and is located at or near the second end of the chromatographic strip.

In a further embodiment of the invention, there is provided a test strip as above, further comprising a fluid collector. In one aspect of the invention, the fluid collector is situated between and is in capillary contact with the second sample filter and the conjugate pad.

In still another embodiment of the invention, there is provided a test strip as one or more of the above, where the fluid collector is situated between and is in direct physical contact with the second sample filter and the chromatographic strip.

In yet another embodiment of the invention, there is provided a test strip as one or more of the above, where the conjugate pad is in capillary contact with the second sample filter and the fluid collector.

In still another embodiment of the invention, there is provided a test strip as one or more of the above, wherein:

(1) each of the first and second sample filters optionally comprises an agglutinating agent, and each of the first and second sample filters is in capillary contact with the chromatographic strip, the first sample filter being located at or near the first end of the chromatographic strip and the second sample filter being located adjacent to the second end of the chromatographic strip;

(2) a fluid collector is situated between the second sample filter and the chromatographic strip, and is in capillary contact with both the second sample filter and the chromatographic strip;

(3) the conjugate pad is situated at the second end of the chromatographic strip and is in capillary contact with the second sample filter and the fluid collector;

(4) the fluid-impermeable barrier is in direct physical contact with the first end of the chromatographic strip and is situated under the first sample filter, where fluid flow from the first sample filter in the direction of the first end of the chromatographic strip is substantially slowed by forcing the fluid to flow underneath the impermeable barrier to reach the first end of the strip;

(5) the first absorber is situated at the first end of the chromatographic strip that, is in direct physical contact with the chromatographic strip, and is located closer to the first end of the chromatographic strip than the first sample filter; and (6) optionally, the second absorber that, if present, is in capillary contact with the first absorbent pad or the chromatographic strip.

In still another embodiment of the present invention, there is provided a test strip as one or more of the above, where:

(1) the fluid collector is situated between the second sample filter and the chromatographic strip, and is in direct physical contact with both the second sample filter and the chromatographic strip;

(2) the conjugate pad is situated at the second end of the chromatographic strip and is in direct physical contact with the second sample filter and indirect contact with the fluid collector;

(3) the fluid-impermeable barrier is in direct physical contact with the first end of the chromatographic strip and the first sample filter, where fluid flow from the first sample filter in the direction of the first end of the chromatographic strip is substantially slowed by forcing the fluid to flow underneath the impermeable barrier to reach the first end of the strip.

Still another embodiment of the present invention is a cassette comprising the test strip of the present invention wherein the cassette is adapted to be read in a device.

Still another embodiment of the present invention is an apparatus for performing an assay for detecting or determining an analyte on a test strip, the apparatus comprising:

(1) at least two bays, each bay holding a cassette according to the present invention;

(2) a sensor that detects addition of liquid to Port-1 and Port-2 of the cassette inserted into each bay;

(3) means for controlling temperature of the cassettes held in the bay; and (4) means for detecting or determining the analyte detected or determined on each test strip of each cassette and reporting each detection or determination of the analyte.

Still another embodiment of the present invention is a method of conducting a lateral flow assay for detection or determination of an analyte in a sample containing a fluid comprising the steps of:

(1) providing a test strip according to the present invention;

(2) applying sample to the sample filter, sufficient for the fluid in the sample to migrate from the sample filter to the capture band and;

(3) mobilizing the detectable agent by adding sample or buffer directly or indirectly to the conjugate pad so that the detectable agent migrates to the capture band; and (4) capturing analyte in the sample, if any, and the mobilizable detectable agent at the capture band to detect or determine the presence of the analyte.

Additional objects, features, or advantages of the present invention will be set forth in part in the figures and description that follows, and in part will be apparent to a person of ordinary skill in the art upon reading the description herein or may be learned by practicing the invention. The objects and advantages of the invention will be realized and attained by means of the elements and combinations particularly pointed out in the Summary of the Invention and the appended claims. Moreover, advantages described in the specification, if not included in the claims, are not per se limitations to the claimed invention.

The inventions illustratively described herein can suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed. Thus, it should be understood that although the present invention has been specifically disclosed by alternative embodiments and optional features, modification and variation of the inventions herein disclosed can be made by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein. In addition, the subject matter of the invention is not to be limited to embodiments described as preferred where alternative embodiments are described.

In addition, where features or aspects of an invention are described in terms of the Markush group, those schooled in the art will recognize that the invention is also thereby described in terms of any individual member or subgroup of members of the Markush group. It is also to be understood that the above description is intended to be illustrative and not restrictive. Many embodiments will be apparent to those in the art upon reviewing the above description. The scope of the invention should therefore, be determined not with reference to the above description, but should instead be determined with reference to the appended claims, along with the full scope of equivalents to which such claims are entitled. The disclosures of all articles and references, including patent publications, are incorporated herein by reference.

BRIEF DESCRIPTION OF THE DRAWINGS

FIG. 13 is a side view of another alternative embodiment of a test strip generally similar to that of FIG. 3, but employing double-sided tape in the first end under sample filter or buffer pad. The double-sided tape can also be applied in a similar pattern to the devices of FIGS. 3, 3a, 3b, 8 and 10, for example.

DETAILED DESCRIPTION OF THE INVENTION

Figure 1:
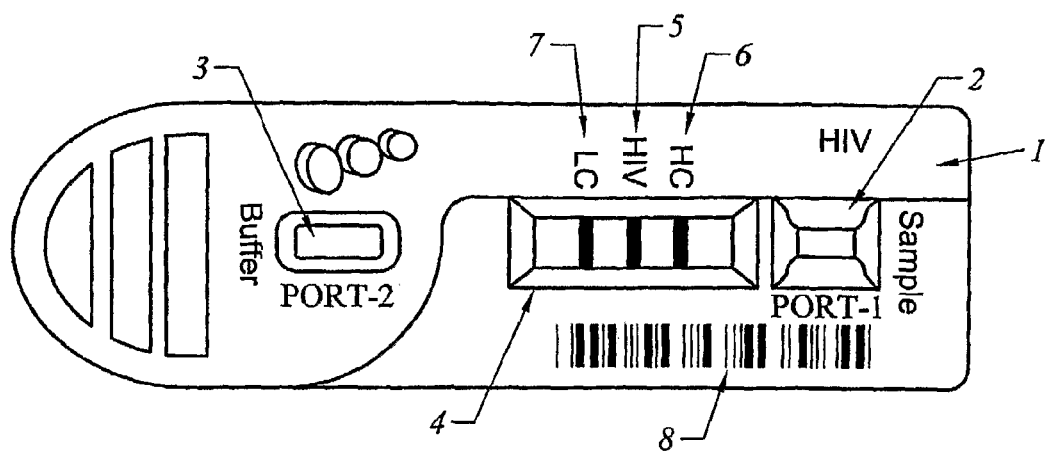
FIG. 1 is a top plan view of an example of a cassette for holding the test strip of the present invention.

The inventors herein have discovered a lateral flow assay method and system including a test strip and/or a cassette for holding the test strip, for determination of the presence and/or quantity of analytes in samples, including but not limited to biological or other samples containing materials including antigens, antibodies, hormones and other secreted proteins, cell surface proteins, transelement proteins, glycoproteins, enzymes, proteins associated with cells and other proteins, proteins associated with pathogens such as bacteria, viruses, and fungi, carbohydrates, drugs, peptides, toxins, nucleic acids, small molecules, and aptamers. This novel assay or system can detect and/or quantitate analytes in small volumes of samples. Generally, the sample volume is less than about 100 µl, or, alternatively, less than about 90 µl, less than about 80 µl, less than about 70 µl, less than about 60 µl, less than about 50 µl, or about 40 µl. This assay or system can also separate cells from fluid in a sample, such as red blood cells or white blood cells or other cell types. This assay or system is substantially volume independent such that, for example, the results are consistent regardless of variation in the volume of red blood cells present in the sample. The assay or system also provides low background noise and is highly efficient.

I. General Principles of Assay Formats Employed in Assay Devices According to the Present Invention In general, assay devices according to the present invention can perform assays such as immunoassays or other specific binding assays in sandwich formats or in an indirect assay format.

A. Sandwich Assay Formats

In general, a sandwich assay format as carried out by assay devices according to the present invention is defined as an assay format in which an analyte is detected by the simultaneous binding of two molecules to it, where both of the molecules binding to the analyte have specific affinity for the analyte. One of the molecules binding to the analyte is labeled and is mobile, while the other of the molecules binding to the analyte is unlabeled and is bound to the chromatographic strip, as described below. A sandwich assay format is also referred to herein as a direct assay format. This format is to be distinguished from an indirect assay, as described in Section (B) below.

For a sandwich assay, if the analyte is an antigen, then both of the molecules binding to the analyte can be an antibody that specifically binds the antigen. If the analyte has multiple copies of the same epitope, such as in a polymer or aggregate, or in a protein that has multiple regions of repetitive amino acid sequence, then both of the molecules binding to the analyte can be the same antibody or antibodies that bind to the same epitope on the analyte. If the analyte does not have multiple copies of the same epitope accessible to antibody binding, then the two molecules binding to the analyte will have to bind to different epitopes. If the analyte is itself an antibody, then one of the molecules binding to the analyte can be an antigen for which the antibody is specific; if multiple binding sites for the antigen are available on the antibody that is the analyte, both of the molecules binding to the analyte can then be the antigen.

B. Indirect Assay Formats

In general, an indirect assay format as carried out by assay devices according to the present invention is defined as an assay format in which the labeled molecule binds the analyte on the basis of a characteristic that distinguishes the analyte from other similar molecules which is that the analyte is specifically bound to another molecule immobilized to the chromatographic strip. For example, if the analyte is an antibody having a particular binding specificity, such as a human anti-HIV antibody, the molecule that is immobilized to the chromatographic strip can be HIV antigen. The labeled molecule can then be labeled anti-human IgG, which will bind all human IgG antibodies regardless of their specificity in binding to a particular antigen. Thus, the only thing that distinguishes the analyte from other human IgG molecules with specificities other than that of binding HIV antigen is that only the anti-HIV antibody will be bound to the chromatographic strip by binding HIV antigen in the capture band on the chromatographic strip. Typically, indirect assays are used to detect antibodies with particular specificities (i.e., binding particular antigens).

II. General Principles Governing Flow Patterns in Assay Formats

A. Unidirectional Flow

As used herein, the term "unidirectional flow" covers all formats in which flow is initiated solely from one end of an assay device according to the present invention. In other words, in formats employing unidirectional flow, fluid is applied only to one end of the device, typically through Port-2, as described below.

B. Bidirectional Flow

In "bidirectional flow," liquid is applied to the test strip sequentially at multiple locations, typically through both Port-1 and Port-2; and the liquid flows through sufficient capillary gradients in each of the directions within the chromatographic strip (the first flow direction and the second flow direction). Various examples of bidirectional flow formats and devices are given below, such as those employing the devices of FIGS. 3 and 4, as well as FIGS. 3A, 3B, 4A, and 4B. Bidirectional flow also encompasses patterns referred to herein as "stop flow" and "reversed flow."

In the "stop flow" format, the liquid that is applied to the test strip at only one location stops flowing at a point located within the chromatographic medium. In the stop flow format, the liquid (sample or buffer) that is added in Port-1 is added in a relatively small volume so that there is not enough liquid to flow through the nitrocellulose element, and flow stops before the flow reaches the labeled reagent (conjugate). The purpose of performing a stop flow assay is to prewet the nitrocellulose element, to block some non-specific protein binding sites, and to ensure that chemicals on the surface of the nitrocellulose element are evenly distributed before labeled reagents flowed into these areas. This is to be contrasted with a "reversed flow" assay format, described further below.

In the "reversed flow" format, the liquid that is applied to the test strip at only one location reverses its flow through the chromatographic medium during the performance of the assay. In a reversed flow assay, a larger volume of liquid is added to Port-1 so that this liquid could flow back. For a reversed flow assay, the cassette is constructed so that when the correct volume of sample is added to Port 1, the liquid moves down the strip toward Port 2 past the control and test zones and then stops and then reverses flow back towards the absorbent pad. Sample is then added to Port 2 and flows up the strip toward the absorbent pad. These operating formats can be arranged by one of ordinary skill in the art by suitable selection of the volume of fluid applied to the test strip and the size and absorptive capacities of absorbing elements of the test strip.

III. Elements Forming Part of Assay Devices

The following describes certain elements that form part of assay devices according to the present invention. Although the elements can be placed in various arrangements, according to the assay format intended and the type of assay to be carried out, in general, the characteristics of the elements defined herein do not change between one arrangement and another. As used herein, the elements described can be in any suitable physical form for the purposes of assay devices according to the present invention, such as, but not limited to, membranes, pads, strips, or other physical forms.

A. Chromatographic Strip

As used in assay devices according to the present invention, the chromatographic strip can be composed of any suitable material that has a high protein binding capability and supports a lateral flow assay. Typically, the chromatographic strip is a hydrophilic element and the protein binding is through noncovalent binding. Although Applicants do not intend to be bound by this theory, current theory of binding of proteins to nitrocellulose states that the initial interaction is electrostatic, but subsequently hydrophobic interactions and hydrogen bonds considerably strengthen the binding. An example of a chromatographic material is the commonly used nitrocellulose element, which has been treated to make it hydrophilic, such as one made by Millipore Corporation (Billerica, Mass.). Another example of a chromatographic element is one made up of particles of a polymer, such as polyethylene, fused together. Such particles can be spherical particles. An example of this type of element is the POREX Lateral-Flo element (POREX Corporation, Fairburn, Ga.). The chromatographic strip is of any size appropriate for the instrument or device used to read the results or for being read visually. For example, for use in conjunction with the device of U.S. Pat. No. 6,136,610, the chromatographic strip is about 5 mm×44 mm. When antigens, such as HIV antigen or HCV antigen, are coated on the chromatographic strip, they are, as one possible alternative, coated in a solution containing trehalose. A suitable concentration of trehalose in the solution is 1.0% (w/w).

When antigens or antibodies are coated onto the chromatographic strip, due to its porous nature, the protein solution distributes itself throughout the depth of the nitrocellulose element. The proteins bind to the pore surfaces. Because of the method of application and the physics of the binding, more protein is bound to the top and center of the line compared to other areas wetted by the solution used to coat the antigens or antibodies onto the chromatographic strip.

The chromatographic strip as used in assay devices according to the present invention includes a capture band, described further below. The chromatographic strip also typically includes one or more control bands, also described further below.

The chromatographic strip (9) of FIGS. 2-13 of the present invention contains at least one capture band for capturing the analyte and at least one control band and, optionally, a second control band. When used in conjunction with the cassette of FIG. 1, the capture band, and the control band or bands can be viewed through the testing window (4). The capture band contains materials that are capable of capturing an analyte in a sample if the analyte is present. For example, if the lateral flow assay is intended to measure hepatitis B virus ("HBV") surface antigen (HBsAg) in a blood sample, the capture band will contain antibody to HBsAg immobilized on the chromatographic strip at the capture band. One of the two controls typically is a high control ("HC") and the other will be a low control ("LC"), as described in further detail below. In one embodiment of the invention, the chromatographic strip (9) of FIGS. 2-13 will additionally contain conjugates or detectable agents at the second end (11) for detecting the captured analyte.

B. Sample Filter

Figure 3:
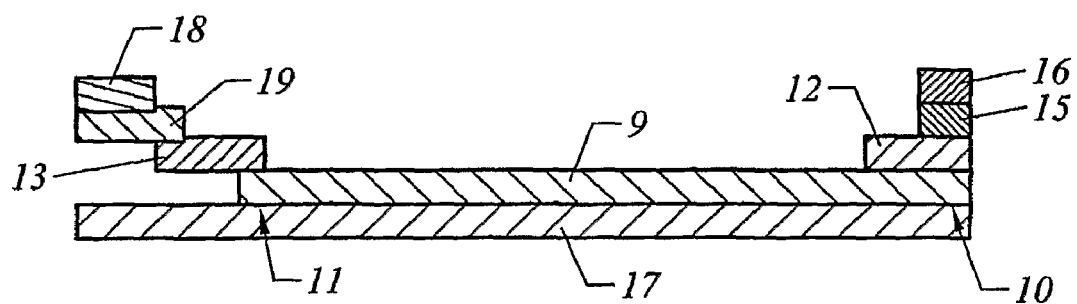
FIG. 3 is a side view of another embodiment of a test strip of the present invention where a sample is applied at Port-2.
Figure 4:
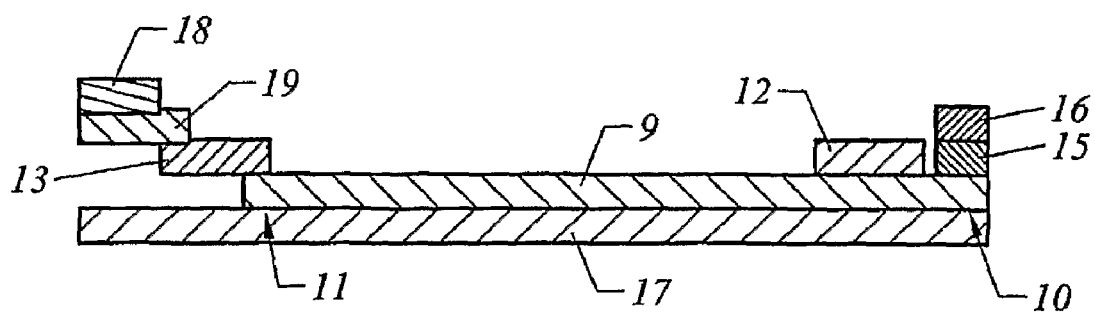
FIG. 4 is a side view of a further embodiment of the test strip of the present invention where a sample can be applied at both Port-1 and Port-2.

Assay devices according to the present invention typically employ a sample filter (in some cases, two sample filters). The location of the sample filter or sample filters can vary, but the sample filter is situated so that fluid present in a sample, when applied onto the sample filter will flow from the sample filter to the chromatographic strip, either directly or indirectly. The sample filter is, in one alternative, a hydrophobic element, or alternatively a hydrophilic element or a synthetic composite of such as typically used in lateral flow assays for sample application. Examples of such sample filters include, but are not limited to hydrophobic filters such as glass fiber filters (Ahlstrom Filtration, Inc. Mount Holly Springs, Pa., USA), composite filters such as Cytosep (Ahlstrom Filtration or Pall Specialty Materials, Port Washington, N.Y.), and hydrophilic filters such as cellulose (Pall Specialty Materials). In one embodiment, a single sample filter is sufficient. In another embodiment, more than a single sample filter may be used. The present sample filter does not require use of any nucleating agent or nucleating particles. However, it may contain an agglutinating agent, such as an antibody or a chemical compound, for example, as described further below. The agglutinating agent may not be necessary when: (1) the assay is run as a bidirectional lateral flow assay when sample is added in Port-1 and only in Port-1 (FIG. 2), and (2) a high concentration of a non-ionic detergent, such as TWEEN 20, is present in the conjugate release buffer for releasing or dissolving the conjugate. In this case, the concentration of the detergent in the conjugate release buffer is at least about 0.1%. The combination of the detergent and conjugate release buffer aids in washing the red blood cells or lysed red blood cells away from the capture and control bands, and decreasing the non-specific binding of analyte to the sample filter. Sample filters in the devices of FIG. 3 and FIG. 4 are constructed similarly. The sample filter optionally contains an agglutinating agent that acts to remove certain materials, such as cells, from a sample. For example, if the sample contains red blood cells, the agglutinating agent may be anti-red blood cell antibodies or may be lectins that agglutinate red blood cells. A sample filter containing such an agglutinating agent or agents is referred to generically as a "whole blood filter."

The size of the sample filter or filters can be as appropriate for the test strip within the parameters specified. For example, for use in conjunction with the device of U.S. Pat. No. 6,136,610, the sample filter is about 5 mm×8 mm when used under port 1 and about 5 mm×13 mm when used under port 2. In one embodiment in which an agglutinating agent is present in the sample filter, the sample filter can be pretreated with a detergent, such as a non-ionic detergent, for example, TWEEN 20, at a concentration of about 0.002%, prior to addition of the agglutinating agent for best results.

The agglutinating agent of the present invention can include an antibody directed to the cells or other materials to be filtered out. For example, if the materials to be filtered out are blood cells, the agglutinating agent of present invention includes an anti-red blood cell antibody and/or an anti-white blood cell antibody. The antibody can be directed to a cell surface antigen. For example, the anti-red blood cell (anti-RBC) antibody includes an anti-red blood cell element antibody such as anti-Band 3 antibody or anti-glycophorin antibody, such as anti-glycophorin A antibody. Such antibodies are commercially available, for example, rabbit anti-human RBC (Buo-shen Biotech, Xia-Men, China) or mouse anti-human RBC(Rui-Tai-En Scientific LLC, Anhui, China), at a concentration appropriate for the assay, such as in the range of about 0.1 mg/ml to about 1 mg/ml, or alternatively 0.2 mg/ml to about 0.8 mg/ml, or alternatively 0.25 mg/ml to about 0.5 mg/ml.

In another embodiment of the present invention, the agglutinating agent is a chemical compound, such as a lectin. Lectins are proteins or glycoproteins that are capable of agglutinating cells and include, for example, concanavalin A, wheat germ agglutinin, and the agglutinins of *Glycine max* and *Phaseolus vulgaris*, abrin, soybean agglutinins and the like, either singly or in combination, as described in Goldstein et al. (1980). Nature 285: 66, and Schnebli, H. P. and Bachi, J. (1975), Reactions of lectins with human erythrocytes. Exot. Cell. Research. 91. Such agglutinins are also commercially available.

C. Sample Pad

In some applications, particularly when the sample does not require the removal of cells or other large particles, a sample pad can replace the sample filter. The term "sample pad" refers to a hydrophobic element, such as a hydrophobic element, that can be used to receive a sample. When the sample is or can be whole blood, the sample pad can contain an agglutinating agent as described above.

The size of the sample pad is suitable for use with the chromatographic strip within the parameters described. For example, for use in conjunction with the device of U.S. Pat. No. 6,136,610, the sample pad is about 5 mm×8 mm when used under port 1 and about 5 mm×13 mm when used under port 2. The sample pad can be optionally pretreated with an anti-erythrocyte antibody or other agglutinating agent, but need not be if buffer is to be applied to Port-1. Alternatively, the sample pad can be hydrophilic, with or without an agglutinin, as described above.

D. Conjugate Pad

The term "conjugate pad" is used to describe an element that is used in many embodiments of assay devices according to the present invention. The conjugate pad is composed of a hydrophobic material, such as glass fiber (Pall Specialty Materials) and contains a conjugate or a detectable agent that can react with an analyte in a sample or with an analyte that is captured on the capture band on the chromatographic strip. The detectable agent includes, for example, antibodies or antigens specific for the analyte that are conjugated to a detectable material such as a colored material, a fluorescent material, or a chemiluminescent material. An example of a colored material is colloidal gold. The conjugate pad herein is of a size suitable for the chromatographic strip within the parameters described. For example, for use in conjunction with the device of U.S. Pat. No. 6,136,610, the conjugate pad is about 5 mm×8.5 mm. The conjugate pads can be preblocked with a buffer solution containing trehalose and casein, although other buffer solutions can alternatively be used for preblocking. For example, the buffer solution can contain from about 2.5% to about 7.5% trehalose, such as about 5% trehalose. For example, the buffer solution contains from about 0.25% casein to about 0.75% casein, such as about 0.5% casein. One suitable buffer solution contains 5% trehalose and 0.5% casein, though other alternatives can be used. The conjugate can be coated on the pads in a solution of 2.5% trehalose and 0.25% casein. The purpose of the trehalose is to stabilize the conjugate when dried on the conjugate pad, not to prevent binding to the conjugate pad or to the nitrocellulose. Prevention of binding can be done with a blocking protein. A suitable blocking protein is 0.5% Hammarsten casein that is base solubilized; alternatively other blocking proteins can be employed. Prevention of binding can also be accomplished by using glass fiber that has been processed with a synthetic polymer binder. Other agents are known which stabilize conjugates when dried on conjugate pads and the invention is not limited to the use of conjugate pads preblocked with trehalose and casein. Such compounds include, but are not limited to, mannitol, in a concentration of from about 5% (w/w) to about 10% (w/w). Mannitol is a 6-carbon cyclic polyalcohol that is not a sugar; such compounds are commonly known as sugar alcohols. Other sugar alcohols that can be used to conjugates when dried on conjugate pads include glycerol, sorbitol, xylitol, erythritol, ribitol, galactitol, and arabitol. Still other compounds are known that can stabilize immobilized antibodies. These include borate buffered solutions of polyethylene glycol. A suitable concentration of borate is from about 1 mM to about 5 mM of borate at pH 9.0. A particularly suitable concentration of borate is 2 mM of borate at pH 9.0. Typically, the molecular weight of the polyethylene glycol is from about 10,000 to about 50,000; preferably, the molecular weight of the polyethylene glycol is about 20,000. Typically, the concentration of the polyethylene glycol is from about 0.05% (w/w) to about 0.25% (w/w). Preferably, the concentration of the polyethylene glycol is about 0.1% (w/w). Therefore, a particularly preferred composition uses 0.1% (w/w) polyethylene glycol of about 20,000 molecular weight. These compounds can also be used to stabilize other proteins, such as HCV antigen, that can be used in test strips according to the present invention.

Use of the conjugate pad is not necessarily required in all embodiments of assay devices according to the present invention. In some alternatives, the conjugate pad is omitted, and the conjugate is applied to the chromatographic strip. These alternatives are described further below.

E. Fluid Collector

The term "fluid collector" is used to describe an element used in some configurations of assay devices according to the present invention. The fluid collector is typically a hydrophobic element, just like the hydrophobic element of the conjugate pad. Unlike the conjugate pad, the fluid collector does not contain any detectable agents and is used as an intermediate element, typically to transmit fluid, directly or indirectly, to the chromatographic strip. The size of the fluid collector is as suitable for the chromatographic strip within the parameters described. For example, for use in conjunction with the device of U.S. Pat. No. 6,136,610, the fluid collector is about 5 mm×13 mm.

F. Capture Band

As described above, the test strip always includes at least one capture band. The term "capture band" as used herein refers to a region or zone on the chromatographic strip that contains at least one analyte binding agent. The analyte binding agent is usually immobilized in a band or zone such that after reaction with a detectable agent, the band or zone produces an observable or measurable result reflecting the presence or amount of analyte present in the sample. The "capture band" may be comprised of more than one capture zone for capturing more than one analyte in the sample, in which event, more than one analyte binding agent may be used. For example, two assay combinations that are considered to be within the scope of the invention are assay combinations that simultaneously detect hepatitis C virus (HCV) and human immunodeficiency virus (HIV), and assay combinations that simultaneously detect Hepatitis B surface antigen (HBsAg) and antibodies to *Treponema pallidum* (TP). Still other combinations are possible and are within the scope of the invention.

G. Control Band

Typically, the chromatographic strip of a device according to the present invention also includes one or more control bands, which contain control agents immobilized in control binding zones. The control agents bind specifically to control binding agents to form a control binding pair, as described in U.S. Pat. No. 6,136,610, incorporated herein by this reference. The present invention typically includes two control bands, although the use of two control bands is not required. The two control bands may be the same or different. A particular advantage to having control binding pairs is that they act as internal controls, that is, the control against which the analyte measurement results may be compared on the individual test strip. The controls may be used to correct for strip to strip variability. One of the controls can be designated a high control ("HC") and the other of the controls can be designated a low control ("LC"). The ratio of HC to LC is typically predetermined as one of the internal quality controls when two controls are used. Additionally, the density of reflection (Dr) of the HC, or, alternatively, of the LC, can be used to determine the RI (relative intensity) of the test band (analyte) by dividing the density of reflection (Dr) of the test band by the Dr of the high control (HC) or low control (LC). The standard curve is made for any quantitative assays by determining the RI of standard reagents with serial concentrations. In qualitative assays, the result is determined by the ratio of the RI of the sample to the cutoff RI or Signal/Cutoff (S/C), where the cutoff is determined by a large number of negative samples. Although, in general, any conventional controls can be used herein, it is generally preferred to use as control compounds that do not exist in the sample or do not immunologically cross-react with compounds that exist in the sample; for example, 2,4-dinitrophenylated bovine serum albumin (BSA-DNP), which can be purchased from Molecular Probes (Eugene, Oreg., cat# A-23018) can be used as the control reagent. The compound 2,4-dinitrophenol (DNP) is a small molecule which does not exist within the human body but acts as a hapten; that is, it is immunogenic when conjugated to a larger molecule such as a protein carrier and injected into an antibody-producing mammal such as a mouse, a rat, a cow, a rabbit, a horse, a sheep, or a goat.

H. Buffer Pad

Some embodiments of assay devices according to the present invention employ a buffer pad. The buffer pad is a hydrophilic element or a synthetic composite, such as a Cytosep element (Ahlstrom Filtration, Inc.). Typically, the buffer pad is accessible in the cassette or other device that holds the assay device for application of reagents, such as at Port-2 in the cassette of FIG. 1. The buffer pad is of a size suitable for the chromatographic strip within the parameters described. For example, for use in conjunction with the device of U.S. Pat. No. 6,136,610, the buffer pad is about 5 mm×13 mm. In some alternatives, the buffer pad can contain an agglutinating agent as described above.

I. Absorbent Pad or Pads

Typically, assay devices according to the present invention include one or more absorbent pads. These absorbent pads serve to direct fluid flow within the device. The size and location of these absorbent pads largely determines the flow pattern, as described above. The absorbent pad is a hydrophilic element that can absorb liquid, such as cellulose (Whatman, Kent, U.K) or a cellulose-glass fiber composite (Whatman, Kent, UK). The absorbent pad herein is of a size suitable for the chromatographic strip within the parameters described. For example, for use in conjunction with the device of U.S. Pat. No. 6,136,610, the absorbent pad is about 5 mm×27 mm.

J. Backing Pad

Some assay devices according to the present invention include a backing pad that serves as a backing for the chromatographic strip. The backing pad can be made of any inert material that is capable of supporting the chromatographic strip, such as a piece of plastic material (G&L Precision Cutting, San Jose, Calif.). The size of the backing pad is suitable for the chromatographic strip within the parameters described. For example, for use in conjunction with the device of U.S. Pat. No. 6,136,610 to Polito et al., the backing pad is about 5 mm×60 mm. However, alternatively, and also within the scope of the invention, the conjugate pad and the sample filter or sample pad or buffer pad at the second end of the strip can also contact the backing when these elements are present.

K. Fluid-Impermeable Barrier

Some embodiments of assay devices according to the present invention incorporate a fluid-impermeable barrier interposed between elements such as a sample filter at or near the first end of the chromatographic strip and the chromatographic strip itself. Other elements can also be affixed to the filter, such as buffer and sample pads, depending on the construction of the test strip. The fluid-impermeable barrier can be, but is not limited to, a double-sided adhesive tape. A suitable double-sided adhesive tape is a polyester tape manufactured by Adhesives Research, but alternative tapes with similar properties can be used. The function of the double-sided adhesive tape is to guide the fluid flow from the sample filter so that it proceeds toward the second end of the chromatographic strip and is delayed from proceeding back toward the first end of the chromatographic strip. Further details on the use of the double-sided adhesive tape are given below.

The components used herein in the Examples, including the absorbent pad, the sample filter, the buffer pad, the chromatographic strip, and the conjugate pad have the properties set forth in Table 1, below, as specified by the manufacturer thereof. However, other alternative components can be used and are known in the art.

IV. Other Definitions Applicable to the Present Invention

For use herein, an "analyte" refers to the material to be detected by use of the lateral flow test strip and method of the present invention. "Analyte" includes but is not limited to: antigens, antibodies, hormones (such as TSH, hCG, LH), drugs, cardiac markers (such as Troponin I, creatine kinase-MB isoforms (CKMB), myoglobin, C-reactive protein (CRP), fatty acid binding protein (FABP), glycogen phosphorylase isoenzyme BB (GPBB), B-type natriuretic peptide (BNP), and NT-pro-BNP), autoimmune disease markers, tumor markers (such as PSA, CEA, α-fetoprotein), proteins associated with a cell ("cell proteins"), secreted proteins, enzymes, cell surface or transelement proteins, glycoproteins and other proteins, proteins or carbohydrates associated with pathogens, such as bacteria, viruses, or fungi, peptides, toxins, nucleic acids, aptamers and carbohydrates. Analytes, as used herein, further includes molecules detectable by specific non-antibody binding proteins such as receptors and nucleic acids detectable by specific Watson-Crick base pairing (hybridization). Other analytes are described further throughout the specification.

An "analyte binding agent" herein is a molecule that specifically binds an analyte in a sample to be analyzed. The "analyte binding agent" may be an antibody or an antigen but is not limited to such. "Analyte binding agent" includes engineered proteins, peptides, haptens and lysates containing heterogeneous mixtures of antigens having analyte binding sites. In one typical, but not exclusive embodiment, the analyte binding agent is either an antibody for binding to an antigen in a sample to be analyzed or is an antigen for binding to an antibody in the sample to be analyzed. If the analyte is a nucleic acid molecule, the analyte binding agent can be a nucleic acid molecule that binds specifically to it such as by Watson-Crick base pairing, or can be a protein that binds a nucleic acid sequence on the basis of sequence-specific interactions. As used herein, the term "specifically binding" or equivalent terminology is defined as binding in which the molecule having specific binding activity, such as, but not limited to, an antibody, binds only to its target and not to another molecule. This binding is controlled by the three-dimensional structures of the molecules involved and is mediated by noncovalent interactions, such as hydrophobic bonds, hydrogen bonds, and salt links.

The term "antigen" as used herein includes infectious agents and other microorganisms or portions thereof, such as bacteria, viruses, capsids, nucleocapsids, or other portions of viruses, fungi, prions, or parasites. The analyte of interest preferably contains an immunogenic portion such that antibodies can be raised against that portion for detection purposes. Bacteria include Gram positive and Gram negative bacteria such as, for example, *Bacillus anthracis, Escherichia coli, Salmonella species, Shigella species, Pasteurella pestis, Helicobacter pylori, Vibrio cholerae, Staphylococcus* species, etc. Viruses include HIV, hepatitis virus A, B, C and D, Herpes simplex virus, cytomegalovirus (CMV), Ebola virus, papilloma virus such as HPV, Rhinoviruses including influenza viruses, SARS virus, and Vaccinia viruses. "Antigen" also includes an immunogenic portion of any compound or infectious agent to which an antibody can be raised. Additionally, the term "antigen" can also include antibodies that are to be detected or macromolecules that can raise antibodies. For example, in testing for human immunodeficiency virus (HIV) or hepatitis C virus (HCV), human anti-HIV antibodies or anti-HCV antibodies are the antigens to be detected, such as by anti-human IgG. In the case of human autoimmune diseases, such as rheumatoid arthritis, Hashimoto's thyroiditis, systemic lupus erythematosus, and other conditions characterized by an abnormal antibody response to autoantigens, the human antibodies against such autoantigens become the antigen.

The term "antibody" as used herein includes polyclonal or monoclonal antibodies or fragments that are sufficient to bind to an antigen or an analyte of interest. The antibody fragments can be, for example, monomeric Fab fragments, monomeric Fab' fragments, or dimeric F(ab)'$_2$ fragments. Also within the scope of the term "antibody" are molecules produced by antibody engineering, such as single-chain antibody molecules (scFv) or humanized or chimeric antibodies produced from monoclonal antibodies by replacement of the constant regions of the heavy and light chains to produce chimeric antibodies or replacement of both the constant regions and the framework portions of the variable regions to produce humanized antibodies. However, in most cases, such modifications are not required to generate an antibody that is suitable for use with the present invention.

The term "conjugate" and "detectable agent" are used interchangeably herein to refer to an antibody or an antigen that is conjugated to a detectable material such as a colored agent, a fluorescent agent or a chemiluminescent agent. In the practice of the present invention, the "conjugate" or "detectable agent" specifically binds the analyte to be determined or the captured analyte immobilized on the capture band. Optionally, the "conjugate" or "detectable agent" produces a measurable quantitative reading at the capture band that reflects the amount of an analyte present at the capture band. As described further below, the direct measurable quantitative density in the capture band does not necessarily reflect the amount of an analyte present at the capture band through binding, but the RI (relative intensity) does reflect the amount of an analyte present at the capture band. The use of RI is discussed further below. Additionally, the use of alternatives for detection are also discussed further below. The conjugate or detectable agent is "mobilizable," which, as used herein, is defined as capable of being resolubilized by an aqueous liquid such as, but not limited to, a sample or a buffer, and then capable of migrating through the test strip.

The term "detectable material" as used herein refers to any material that can be conjugated to an antigen or an antibody and that can be detected, such as at the capture band. The material can be a particle, a colored material, a fluorescent material, a chemiluminescent material, a bioluminescent material, an enzymatic material, or a radioactive material and may include more than one material. Such materials are generally described as labels. If more than one material is used, any combination of the possible materials can be used. For example, if the assay is intended to detect more than one analyte, detectable materials to be used may be fluorescent materials that fluoresce at different wavelengths. The particles can be colloidal gold particles, colloidal sulfur particles, colloidal selenium particles, colloidal barium sulfate particles, colloidal iron sulfate particles, colloidal metal iodate particles, colloidal silver halide particles, colloidal silica particles, colloidal metal (hydrous) oxide particles and the like as described in U.S. Pat. No. 6,136,610, with or without an organic or inorganic coating, protein or peptide molecules, liposomes, or organic polymer latex particles such as polystyrene latex beads. The size of the particles may be related to porosity of the chromatographic strip.

The term "operable contact" is used herein as follows: Two solid components are in operable contact when they are in contact, either directly or indirectly, in such a manner that a liquid can flow from one of the two components to the other substantially uninterruptedly, by capillarity or otherwise. "Direct contact" means the two elements are in physical contact, such as edge-to-edge or front-to-back. "Indirect contact" means the two elements are not in physical contact, but are bridged by one or more conducting means. This bridging by one or more conducting means could be either edge-to-edge or front-to-back. The term "capillary contact," used herein, is equivalent to operable contact. As used herein, in this and other contexts, the term "substantially" is defined as having the property being described to a desired degree for effectuating the specific function being carried out such that deviations from that property are not significant in the operation of the step or device being described.

It is to be understood that both the foregoing general description and the following detailed description are exemplary and explanatory only and are not restrictive of the invention, as claimed. Moreover, it must be understood that the invention is not limited to the particular embodiments described, as such may, of course, vary. Further the terminology used to describe particular embodiments is not intended to be limiting, since the scope of the present invention will be limited only by its claims.

Further, while the present invention may be used independently or in conjunction with any analytical device adapted to read the results manually or automatically, the invention herein is exemplified using the apparatus and cassette of U.S. Pat. No. 6,136,610 and, in one embodiment of the invention, utilizing the bidirectional flow mechanism of U.S. Pat. No. 6,528,323. It is to be understood that the present invention is not limited to use in such apparatus or cassette.

Referring to FIG. 1, FIG. 1 is a top plan view of a cassette (1) that can be used with the test strip of the present invention: the cassette (1) has two ports. Port-1 (2) can be used for application of a sample in a sandwich assay, such as detection of HBsAg; or an indirect bilateral flow assay for detection of an analyte, such as anti-HIV antibody; and Port-2 (3) can be used for application of a sample in a sandwich assay, or a reagent, such as a buffer in an indirect bilateral flow assay. The cassette (1) also contains a testing window (4) for viewing results of the assay. Through the test window (4), the capture band (5) for the analyte to be detected, labeled human anti-HIV in this example, can be observed, together with a first control band (6), labeled HC in this example, and a second control band (7), labeled LC in this example. The cassette (1) can optionally include a bar code (8) for management of assay types, the product expiration date, and adjustment of inter-lots variables.

In the present invention, if the cassette of FIG. 1 is used, Port-1 (2) or Port-2 (3) can each be used for application of sample or reagent, as described in greater detail below.

V. Specific Assay Devices According to the Present Invention and Assays Performable by Such Devices

A. FIG. 2

Figure 2:
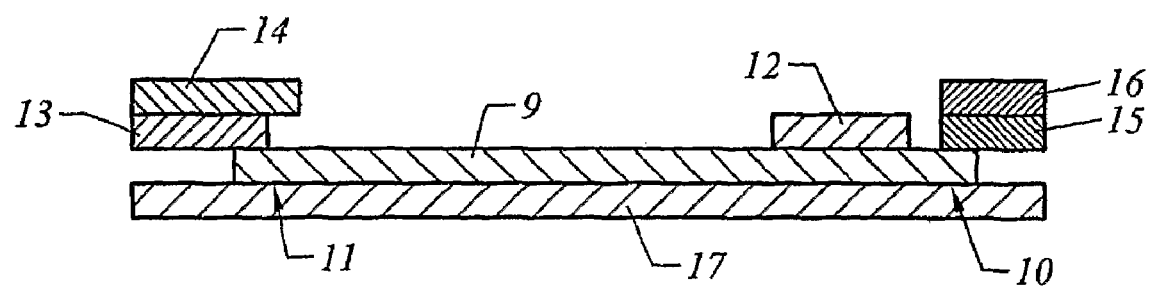
FIG. 2 is a side view of one embodiment of a test strip of the present invention where a sample is applied at Port-1.
Figure 6:
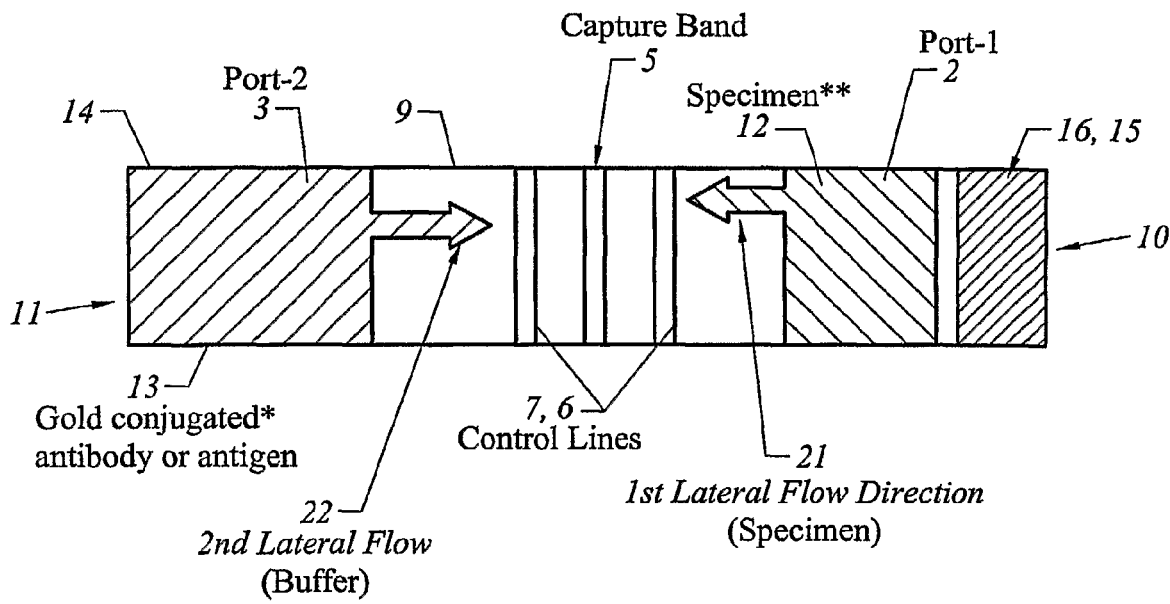
FIG. 6 is a top view of one embodiment of the present test strip showing bidirectional flow of fluid upon application of sample at Port-1 and buffer at Port-2.

Referring to FIG. 2, FIG. 2 is a side view of a test strip for use in one embodiment of the present invention. In this embodiment, shown in FIG. 2, there is a sample filter (12) situated at Port 1 (2 of FIG. 1) at a first end (10) of a chromatographic strip (9), and a buffer pad (14) situated at Port 2 (3 of FIG. 1). The buffer pad (14) sits on top of a conjugate pad (13) which contains at least one mobilizable detectable agent, commonly referred to as a "conjugate," that specifically binds the analyte or an agent that binds the analyte. Such a conjugate may be, for example, an analyte-specific antibody or analyte-specific antigen conjugated to colloidal gold, for example. Optionally, the conjugate pad (13) also contains a second mobilizable detectable agent that specifically binds an immobilized control agent at one or more of the control bands (6, 7), as shown in FIG. 6, for example. For a whole blood assay, the sample filter (12) contains an agglutinating agent to agglutinate the red blood cells in the whole blood sample. A first absorbent pad (15) is situated at the first end (10), adjacent to the sample filter (12) on the side of the sample filter (12) away from the conjugate pad (13) or buffer pad (14). An optional second absorbent pad (16) in capillary contact with the first absorbent pad (15) may be used. The second absorbent pad (16), if present, is situated directly on top of the first absorbent pad or overlaps the first absorbent pad (15). The first absorbent pad (15) is in capillary contact with or overlaps the first end (10) of the chromatographic strip (9). A plastic backing pad (17) can optionally be used to support the chromatographic strip. The chromatographic strip (9) also contains at least one capture band (5) for each analyte to be detected and one or more control bands (6, 7) as shown in FIG. 6, for example. Each capture band (5) contains an immobilized antibody or an immobilized antigen that specifically reacts with the analyte to be detected in the sample. Each control band (6, 7) optionally contains an immobilized antibody or antigen that reacts non-specifically with the sample, or reacts specifically with a control reagent in the conjugate pad (13).

In performing an indirect assay using the format of FIG. 2, a sample containing whole blood is applied to the sample filter (12) at Port 1 (2), as shown in FIG. 6. RBCs are retained in the sample filter (12) while fluid from the sample flows from the sample filter (12) to the chromatographic strip (9) at the first end (10), and from the first end (10) in a first lateral flow direction (21 of FIG. 6) towards the second end (11) ("first fluid flow"). In the course of the first fluid flow, the sample fluid moves past the capture band (5) which contains, for example, HIV antigen or HCV antigen in an HIV or HCV test, respectively, that interacts with the analyte in the sample, such as human anti-HIV antibody or human anti-HCV antibody, respectively. The fluid also moves past the control bands (6, 7) during the course of the first lateral fluid flow (21). Further, the first fluid flow in the first lateral flow direction (21) desirably and apparently ceases flow between the control band closest to the conjugate pad (7) and the conjugate pad (13). The analyte in the sample, if present, is primarily captured at the capture band (5) during the course of fluid flow in the first lateral flow direction (21), forming a first immunocomplex, such as a HIV-human anti-HIV antibody complex, at the capture band (5). A buffer is then applied to the buffer pad (14) to release the conjugate in the conjugate pad (13). In one embodiment, the released conjugate contains at least one and optionally two labeled reagents, one that specifically reacts with the first immunocomplex at capture band (5), for example, a labeled anti-human IgG and, optionally, one that reacts with the control reagent at the control bands (6, 7). The released conjugate migrates from the second end (11) of the chromatographic strip (9) in the second lateral flow direction (22) towards the first end (10). During fluid flow in the second lateral flow direction (22), a detectable complex of labeled control binding reagent and control reagent is formed at the control bands (6 and 7) and a detectable second immunocomplex of labeled anti-human IgG antibody and the first immunocomplex is formed at the capture band (5). The indirect assay therefore allows the first immunocomplex, formed between analyte in the sample and the capture reagent at the capture band (5) during the first fluid flow, to be detected during the second fluid flow.

Notably, when the strip configuration of FIG. 2 is used for determination of analytes in non-whole blood samples, such as serum or plasma samples, the sample filter (12) need not contain an agglutinating agent. This configuration can be used for both sandwich assays and/or indirect assays. In a sandwich assay, for example, such as a HBsAg test, a buffer, if the best performance requires such, can be added to Port 1 and a sample added to Port 2. In the case of a sandwich assay for HBsAg, the serum sample could also be added to both Port 1 and Port 2, or the sample could be added only to Port-2. To carry out these assays, sample is applied to the sample filter (12) at Port 1 (2), as shown in FIG. 6. Fluid will flow from the sample filter (12) to the chromatographic strip (9) at the first end (10) and from the first end (10) in a first lateral flow direction (21 of FIG. 6) toward the second end (11), past the capture band (5) and the control bands (6, 7); the fluid ceases flow (the "Stop Flow" format) before reaching the conjugate pad (13) or optionally, the fluid can flow into the conjugate pad (13) and dissolve the conjugate, if it is desired for improved performance of the assay. Typically, in assays performed with test strips according to the present invention, particularly indirect assays (antibody testing), it is preferred to have a stop flow format, i.e. not causing the liquid to flow through and reach the conjugate, especially for indirect assays (antibody testing) because the antibodies in the sample will interact with the labeled anti-human IgG (or IgM) in conjugate, forming an immunocomplex before the conjugate reaches the capture band. This may cause a false negative result. Therefore, in an indirect assay, the liquid from Port 1 should not reach the conjugate. However, in a sandwich assay, the use of the stop flow format is not required.

Thus, in one embodiment, between the control band (7) and the conjugate pad (13), fluid from the sample ceases flow in the first lateral flow direction (21). In an HbsAg sandwich assay, for example, if the analyte being detected is present in the sample, HBsAg is captured at the capture band (5) which contains, for example, an immobilized human anti-HBsAg antibody ("immobilized capture antibody"). In the course of fluid flow in the first lateral flow direction, a first immunocomplex, such as HBsAg and anti-HBsAg capture antibody complex is formed at the capture band (5). Again, during the course of fluid flow in the second lateral flow direction (22), if there is any unbound analyte remaining in the sample after the first fluid flow, additional first immunocomplex is formed during the second fluid flow.

A second aliquot of the sample is applied to the buffer pad (14) which need not contain an RBC agglutinating agent. Fluid from the sample flows through the conjugate pad (13) and releases the conjugate. The conjugate contains a first labeled mobilizable reagent that reacts with the analyte in the sample, such as labeled human anti-HBsAg antibody conjugated to a detectable agent, for example, colloidal gold. Optionally, the conjugate contains a second labeled mobilizable reagent that reacts with the control reagent at the control bands (6, 7). During fluid flow in the second lateral flow direction (22), a second immunocomplex, such as labeled human anti-HBsAg antibody and HBsAg, forms and migrates from the second end (11) of the chromatographic strip (9) in the second lateral flow direction (22) towards the first end (10) if the analyte is present in the sample. As fluid flow in the second lateral flow direction continues, a detectable complex of labeled control-binding reagent and control reagent is formed at the control bands (6 and 7) and a detectable third immunocomplex containing complexed first and second immunocomplexes is formed at the capture band (5). The bidirectional lateral flow aids in washing contaminants away from the capture and control bands, reducing background noise.

The format of FIG. 2 may be used in an indirect assay for detection of analyte in a serum or plasma sample. In this format, the agglutinating agent may optionally be excluded from the sample filter (12). The analysis is conducted by first adding sample to the sample filter (12) at Port 1 (2) to prewet the chromatographic strip (9). Buffer is then added to Port 2 (3). Fluid from the sample releases the conjugate, for example, from the conjugate pad (13). The analyte in the sample, anti-HIV, for example, if present, reacts with the capture band to form a first antigen-antibody binding pair, i.e., a first immunocomplex during the course of fluid flow in the first lateral flow direction (21). The released conjugate migrates from the second end (11) of the chromatographic strip (9) in a second lateral flow direction (22) towards the first end (10). During fluid flow in the second lateral flow direction, a detectable second immunocomplex of labeled anti-human IgG antibody and the first immunocomplex is formed at the capture band, which can be detected and quantified.

In a variation of the above-mentioned embodiment, not shown, a conjugate pad (13) is not used and mobilizable detectable agents are incorporated into the chromatographic strip (9) at the second end (11). In this embodiment, a buffer pad (14) is situated at Port 2 (3 of FIG. 1), on top of or overlapping with the chromatographic strip (9). The buffer pad (14) may sit on top of the mobilizable detectable agent.

In another variation of the above-mentioned embodiment, not shown, a buffer pad (14) is not used, the conjugate pad (13) is situated on top of and/or overlaps the second end of the chromatographic strip. Buffer can be added directly onto the conjugate pad (13).

In the embodiment as exemplified in FIG. 2, the sample filter (12) is preferably a hydrophobic element, or alternatively a hydrophilic element or a synthetic composite of such type as is typically used in lateral flow assays for sample application.

In the embodiment exemplified in FIG. 2, the buffer pad (14) is accessible in the cassette (1) for application of reagents at Port-2 (3).

B. FIGS. 3 and 4

In yet another embodiment, shown in FIG. 3, the test strip is suitable for performance of a sandwich assay, such as for simultaneous detection of HBV surface Ag (HBsAg) and for detection of antibody to *Treponema pallidum*, causative agent of syphilis. In this format, there is a second sample filter (18), a fluid collector (19), optionally a conjugate pad (13), all situated at the second end (11) of the chromatographic strip (9). There is also a first sample filter (12) and at least one absorbent pad (15) situated at the first end (10) of the chromatographic strip (9). A first absorbent pad (15) is situated on top of the first sample filter (12).

In a variation of the embodiment shown in FIG. 3 (the variation is not shown), a conjugate pad is not used, and the mobilizable detectable agents are incorporated into the chromatographic strip (9) at the second end (11). In this configuration, the fluid collector (19) is directly in capillary contact with the chromatographic strip (9), the fluid collector may be situated entirely on top of the second end (11) of the chromatographic strip (9) or may overlap the chromatographic strip (9).

In another variation of the embodiment of FIG. 3 (the variation is not shown), the first sample filter (12) is replaced with a sample pad for application of a reagent, such as a buffer. The sample pad is composed of an absorbent material which is capable of holding sufficient buffer for running the assay.

FIG. 4 shows a variation in which the first and optionally the second absorbent pad are situated adjacent to the sample filter (12) at the first end (10) of the chromatographic strip (9). The format of FIG. 4 is suitable for performing sandwich assays such as those for prostate specific antigen (PSA) and thyroid stimulating hormone (TSH).

Figure 7:
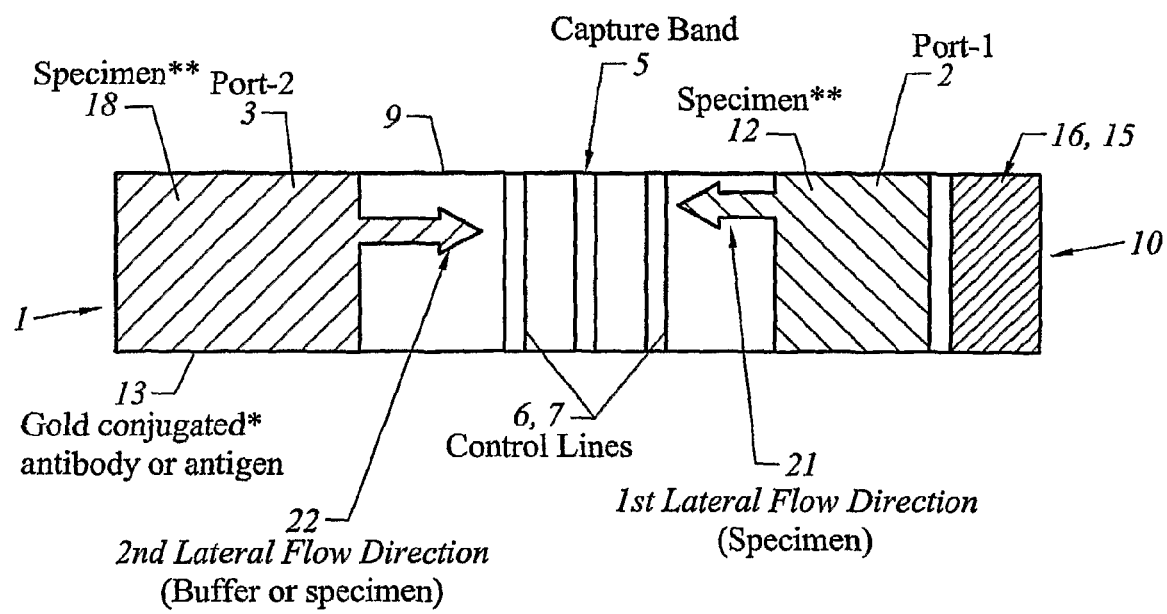
FIG. 7 is a top view of another embodiment of the present test strip showing bidirectional flow of fluid upon application of sample at both Port-1 and Port-2.

In the operation of an assay using the formats of FIG. 3 and FIG. 4, sample containing whole blood is added to both Port 1 (2) and Port 2 (3) of FIG. 1. In this format, both first sample filter (12) and second sample filter (18) are preferably blood filters to filter out red blood cells. FIG. 7 illustrates the operation of a sandwich assay using the embodiment shown in FIG. 4. An aliquot of a sample containing RBC is applied to the first sample filter (12) at the first end (10) of the chromatographic strip (9). Fluid from the sample flows in the first lateral flow direction (21) from the first end (10) to the second end (11), flowing past the capture band (5) and the control bands (6 and 7). The analyte, if present, is captured at the capture band (5), the analyte-antibody forming a first immunocomplex at capture band (5). A second aliquot of the same sample is then applied to the second sample filter (18) at Port 2 (3). Fluid from the second sample filter (18) passes through a fluid collector (19 of FIG. 4) and a conjugate pad (13) to the second end (11), and then from the second end (11) in a second lateral flow direction (22) toward the first end (10), past the capture band (5) and the control bands (6 and 7). The analyte, if present is captured at the capture band (5) by the detection reagent, such as an antibody, the analyte-antibody complex forming a sandwich. In this format, the analyte, for example, HBsAg, applied to Port 2 (3) will first combine with the conjugate from the conjugate pad, for example, labeled anti-HBsAg antibody, such as anti-HBsAg antibody conjugated to colloidal gold, to form an analyte-conjugate complex, which then migrates to the capture zone and reacts with an anti-HBsAg antibody immobilized at the capture zone, which by that time would have also captured HBsAg from analyte applied to Port 1 (2).

In a variation, addition of sample to sample filter (12) at the first end (10) may be omitted and sample can be added directly to the second sample filter (18) at Port 2 (3). In this format, buffer is first added to Port 1 to prewet the test strip, the buffer flowing in a first lateral flow direction (21) from the first end (10) to the second end (11). Then sample is applied to Port 2 (3). Fluid from sample passes through the fluid collector (19) and a conjugate pad (13) to the second end (11) and from the second end (11) in a second lateral flow direction (22) past the capture band (5) and the control bands (6 and 7). The analyte in the sample combines with the conjugate to form a complex, the complex then flows to the capture band and the control bands. The analyte-conjugate complex is captured at the capture band (5), forming a sandwich.

Notably, when the strip configuration of FIG. 3 or FIG. 4 is used for determination of analytes in non-whole blood samples, such as serum or plasma samples, the sample filter (18) in FIG. 3, or the sample filters (12 and 18) in FIG. 4 do not contain an agglutinating agent. This configuration can be used for both sandwich assays and indirect assays.

As used herein, the terms "sample pad" and "sample filter" refer to elements that can be used to receive a sample, such as a sample of blood, serum, or plasma. The term "sample pad" refers to a hydrophilic element, such as a hydrophilic element, that can be used to receive a sample. When the sample is or can be whole blood, the sample pad can contain an agglutinating agent as described above. The term "sample filter" can refer to a generally hydrophobic element, such as a glass fiber filter, that can be similarly used to receive a sample. The sample filter can also contain an agglutinating agent as described above. However, the sample filter can be a hydrophilic element, such as a sample pad, pretreated with an anti-erythrocyte antibody or other agglutinating agent. The term "whole blood filter," as used herein, refers to a sample filter that contains an agglutinating agent. However, when the strip configuration of FIG. 2 is used for determination of analytes in samples other than whole blood samples, such as serum or plasma or other biological fluids, the sample filter (12) need not contain an agglutinating agent. This configuration can be used for both sandwich assays and indirect assays. In a sandwich assay, for example an assay of HBsAg, a sample or a buffer, if the best performance requires such, is applied to the sample filter (12) at Port-1 (2), as shown in FIG. 6. In such a sandwich assay of HBsAg, the sample can be added to both Port-1 and Port-2 or only in Port-2. Fluid will flow from the sample filter (12) to the chromatographic strip (9) at the first end (10) and from the first end (10) in a first lateral flow direction (21 of FIG. 6) toward the second end (11), past the capture band (5) and the control bands (6, 7); the fluid ceases flow (the "Stop Flow" format) before reaching the conjugate pad (13) or optionally, the fluid can flow into the conjugate pad (13) and dissolve the conjugate, if it is desired for improved performance of the assay. In an indirect assay, the Stop Flow format is particularly suitable because antibodies in the sample are precluded from interacting with the labeled anti-human IgM or anti-human IgG in the conjugate, forming an immunocomplex before the conjugate reaches the capture band and thus giving a false negative result.

Figure 3A:
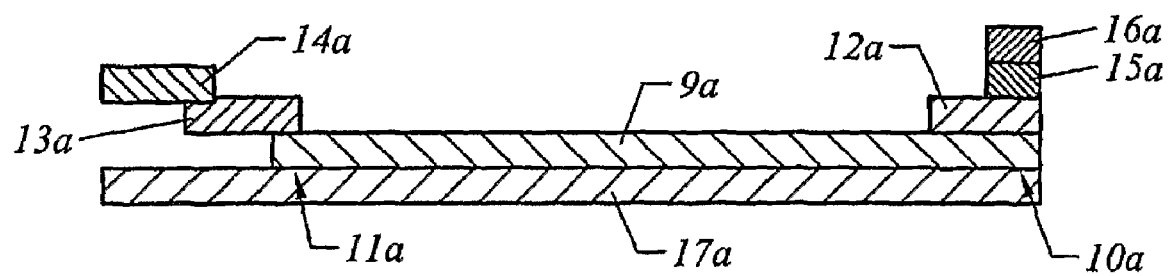
FIG. 3A is a side view of a variation of the device shown in FIG. 3 employing a buffer pad.
Figure 4A:
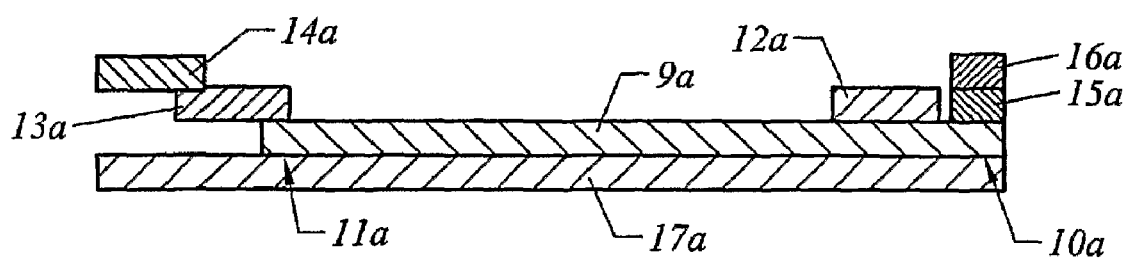
FIG. 4A is a side view of a variation of the device shown in FIG. 4 employing a buffer pad.

In one embodiment of the invention, as shown in FIG. 3A and FIG. 4A, the conjugate pad (13a) is situated at the second end of the chromatographic strip (11a), and a buffer pad (14a) is situated on top of the conjugate pad (13a). In this embodiment, the conjugate pad (13a) overlaps the second end (11a) of the chromatographic strip (9a) by a distance sufficient for fluid to pass from the buffer pad (14a) through the conjugate pad (13a) and onto the chromatographic strip (9a). This distance of overlap may be from about 0.5 mm to about 10 mm, or alternatively from about 1 mm to about 8 mm, from about 2 mm to about 5 mm, or about 2-3 mm.

The buffer pad (14a) may be of any suitable size provided that it can absorb or hold an amount of fluid sufficient to dissolve the detectable agent in the conjugate pad (13a) or in the chromatographic strip (9a) as described below. In one embodiment, the buffer pad is larger than the conjugate pad. In another embodiment, the buffer pad is the same size as the conjugate pad. In yet another embodiment, the buffer pad is smaller than the conjugate pad.

For this alternative of the device as shown in FIG. 3A and FIG. 4A, the first absorbent pad (15a) is situated at the first end (10a) of the chromatographic strip (9a) adjacent to the sample filter (12a) on the side of the sample filter (12a) away from the conjugate pad (13a) or the buffer pad (14a). In the device described in FIG. 3A, the absorbent pad overlaps the sample filter (12a), but in the device described in FIG. 4A it does not. An optional second absorbent pad (16a) is in capillary contact with the first absorbent pad (15a). In one embodiment, the optional second absorbent pad (16a) is situated directly on top of the first absorbent pad (15a). The first absorbent pad (15a) overlaps the first end (10a) of the chromatographic strip (9a) by a distance sufficient to allow capillary flow of fluid from chromatographic strip (9a) to the first absorbent pad (15a). This distance is in a range from about 0.5 mm to about 10 mm, alternatively from about 1 mm to about 8 mm, from about 2 to about 5 mm, or about 4 to 5 mm. Additionally, a third absorbent pad can optionally be used.

A backing pad (17a) can optionally be used to support the chromatographic strip (9a), although certain chromatographic strips are available that already have a backing in place.

Figure 3B:
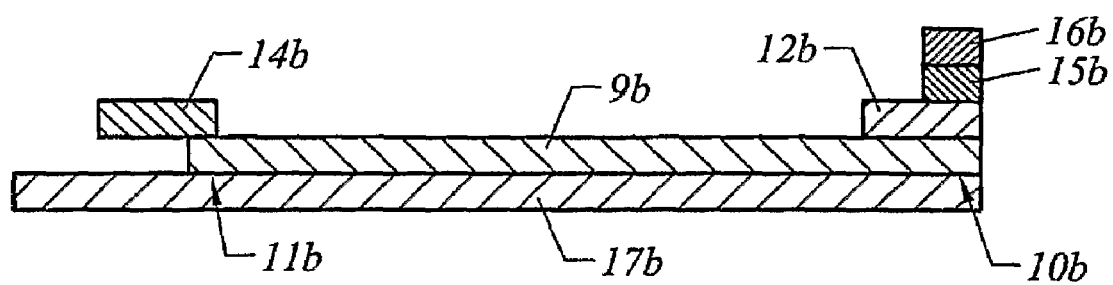
FIG. 3B is a side view of another variation of the device shown in FIG. 3 in which the buffer pad is directly in contact with the chromatographic medium.
Figure 4B:
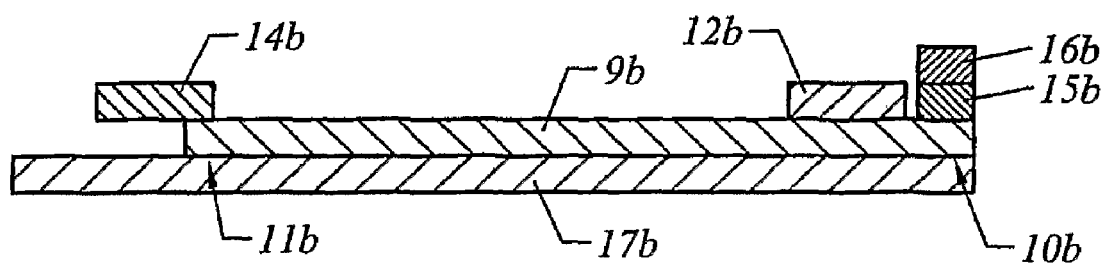
FIG. 4B is a side view of another variation of the device shown in FIG. 4 in which the buffer pad is directly in contact with the chromatographic medium.

In another embodiment of the invention as shown generally in FIG. 3B and FIG. 4B, a conjugate pad is not used, and detectable agents that are usually present in a conjugate pad, when the conjugate pad is used, are incorporated into the second end (11b) of the chromatographic strip (9b). In such an embodiment, a buffer pad (14b) is situated on top of the chromatographic strip (9b). In one alternative, the buffer pad (14b) overlaps the second end (11b) of the chromatographic strip (9b) by a distance sufficient to allow fluid applied on the buffer pad (14b) to flow by capillary action onto the chromatographic strip (9b) to dissolve the detectable agent present at the second end (11b) of the chromatographic strip (9b). In this alternative arrangement for FIG. 3B and FIG. 4B, the buffer pad (14b) may be situated directly on top of the second end (11) of the chromatographic strip (9b), such as on top of the detectable agents in the second end (11b) of the chromatographic strip (9b). Fluid applied onto the buffer pad (14b) in this embodiment can dissolve the detectable agent and move the detectable agent from the second end (11b) of the chromatographic strip (9b) in a second flow direction towards the first end (10b) of the chromatographic strip (9b). If the buffer pad (14b) overlaps the chromatographic strip (9b), the overlap may be in a range from about 0.5 mm to about 10 mm, alternatively from about 1 mm to about 8 mm, from about 2 to about 5 mm, or about 2 to 3 mm.

In one embodiment of the present invention, as shown in FIG. 3, at least one absorbent pad (15) is in capillary contact with the first sample filter (12). Optionally, a second absorbent pad (16) is situated on top of the first absorbent pad (15). The absorbent pads (15, 16), in one embodiment (FIG. 3), are situated on top of the first sample filter (12) but do not obstruct the application of sample or reagent onto the first sample filter (12). A third absorbent pad can optionally be used.

In as yet another embodiment of the present invention, as shown in FIG. 4, the absorbent pads (15, 16) are situated adjacent to the first sample filter (12) at the first end (10) of the chromatographic strip, on the side of the first sample filter (12) that is opposite the sample filter (18). As indicated above, the first sample filter (12) is typically a whole blood filter containing an agglutinating agent. However, as indicated below, when it is intended to apply buffer through Port 1, the first sample filter (12) can be replaced with a sample pad. This can be hydrophilic, as described above, and need not necessarily be pretreated with anti-erythrocyte antibody or agglutinating agent as described above.

Alternatively, when the first sample filter (12) is replaced with a sample pad, the sample pad is a hydrophilic element such as Cytosep (Ahlstrom Filtration, Inc.) in one embodiment of the invention, such as shown in FIG. 3, where the sample pad is available for application of a reagent, such as a buffer, through Port-1 (2) of the cassette (1) of FIG. 1. The sample pad is useful, for example, for application of a buffer to pre-wet the chromatographic strip (9) prior to addition of a sample to the sample filter (18).

In another embodiment of the invention, such as exemplified in FIG. 4, when the first sample filter (12) is replaced with a sample pad, the sample pad can be a hydrophobic element, just like the hydrophobic element of the sample filter (18). In this embodiment, the sample pad may also contain an agglutinin. Alternatively, the sample pad can be hydrophilic, with or without an agglutinin, as described above.

The arrangement of FIG. 4 is particularly suited to the performance of sandwich immunoassays such as those for prostate specific antigen (PSA) or thyroid stimulating hormone (TSH).

Devices according to FIG. 3 or FIG. 4 can be operated in several modes. In one of these modes, sample (whole blood) is added to both Port 1 and Port 2. When whole blood as sample is added to both Port 1 and Port 2, both the first sample filter (12) and the second sample filter (18) are preferably whole blood filters to prevent blood cells, particularly erythrocytes, from entering the chromatographic strip. Alternatively, a buffer can be added to Port 1 and whole blood as sample is added to Port 2. In that alternative, the first sample filter (12) need not be a whole blood filter; that is, it need not contain an agglutinating agent. However, it is generally preferred that both the first sample filter (12) and the second sample filter (18) are whole blood filters, regardless of whether sample or buffer is to be added to Port 1 in the performance of the assay.

In the operation of an assay using the formats of FIG. 3 and FIG. 4, sample containing whole blood is added to both Port 1 (2) and Port 2 (3) of FIG. 1. In this format, both first sample filter (12) and second sample filter (18) are preferably blood filters to filter out RBCs. FIG. 7 illustrates the operation of a sandwich assay using the embodiment shown in FIG. 4. An aliquot of a sample containing RBC is applied to the first sample filter (12) at the first end (10) of the chromatographic strip (9). Fluid from the sample flows in the first lateral flow direction (21) from the first end (10) to the second end (11), flowing past the capture band (5) and the control bands (6, 7). The analyte, if present, is captured at the capture band (5), the analyte-antibody forming a first immunocomplex at the capture band (5). A second aliquot of the same sample is then applied to the second sample filter (18) at Port 2 (3). Fluid from the second sample filter (18) passes through a fluid collector (19 of FIG. 4) and a conjugate pad (13) to the second end of the strip (11), and then from the second end (11) in a second lateral flow direction (22) toward the first end (10), past the capture band (5) and the control bands (6, 7). The analyte, if present is captured at the capture band (5) by the detection reagent, such as an antibody, the analyte-antibody complex forming a sandwich. In this format, the analyte, for example, HBsAg, applied to Port 2 (3) will first combine with the conjugate from the conjugate pad, for example, labeled anti-HBsAg antibody, such as anti-HBsAg antibody conjugated to colloidal gold, to form an analyte-conjugate complex, which then migrates to the capture zone and reacts with an anti-HBsAg antibody immobilized at the capture zone, which by that time would have also captured HBsAg from analyte applied to Port 1 (2).

In a variation of the formats of FIG. 3 and FIG. 4, addition of sample to the sample filter (12) at the first end (10) may be omitted and sample can be added directly to the second sample filter (18) at Port 2 (3). In this format, buffer is first added to Port 1 to prewet the test strip, the buffer flowing in a first lateral flow direction (21) (FIG. 6) from the first end (10) to the second end (11). Then sample is applied to Port 2 (3). Fluid from the sample passes through the fluid collector (19) and a conjugate pad (13) to the second end (11) and from the second end (11) of the strip in a second lateral flow direction (22) past the capture band (5) and the control bands (6, 7). The analyte in the sample combines with the conjugate to form a complex, the complex then flows to the capture band and the control bands. The analyte-conjugate complex is captured at the capture band (5), forming a sandwich.

Notably, when the strip configuration of FIG. 3 or FIG. 4 is used for determination of analytes in non-whole blood samples, such as serum or plasma samples, the sample filter (18) in FIG. 3, or the sample filters (12 and 18) in FIG. 4 do not contain an agglutinating agent. This configuration can be used for both sandwich assays and indirect assays.

In the embodiments as exemplified in FIGS. 3 and 4, the second sample filter (18) is typically a hydrophobic element such as a glass fiber element (Ahlstrom Filtration, Inc.). In one aspect of this embodiment, the second sample filter (18) contains an agglutinating agent. In another aspect of the invention, the hydrophobic element is treated with a detergent, such as a non-ionic detergent, for example, TWEEN 20, at a concentration of about 0.002%, prior to addition of the agglutinating agent. The second sample filter (18) is available for application of a sample through Port-2 (3) of the cassette (1) of FIG. 1.

In another embodiment of the invention, such as exemplified in FIG. 4, when the first sample filter (12) is replaced with a sample pad, the sample pad can be a hydrophobic element, just like the hydrophobic element of the sample filter (18). In this embodiment, the sample pad may also contain an agglutinin. Alternatively, the sample pad can be hydrophilic, with or without an agglutinin, as described above.

C. FIG. 8

Figure 8:
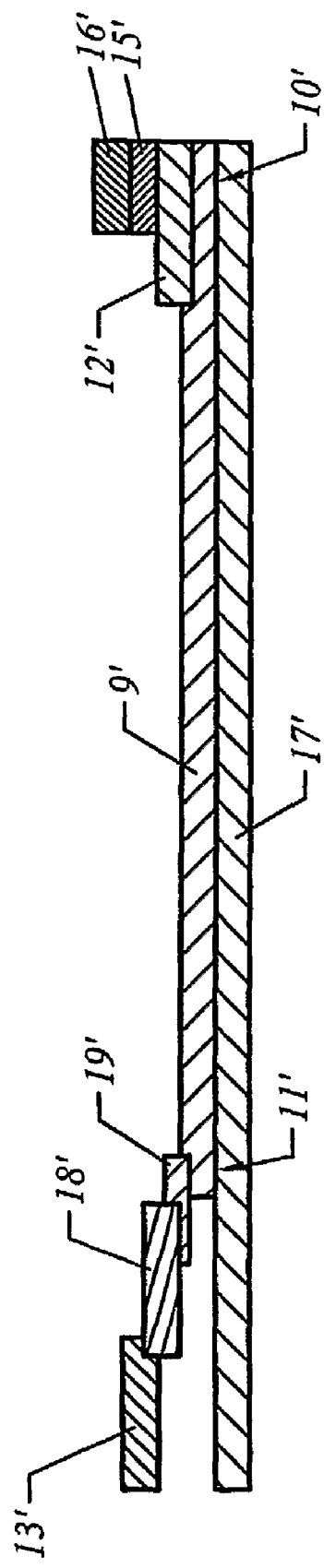
FIG. 8 is a side view of an alternative embodiment of the test strip generally similar to that of FIG. 3 but one in which the sample filter (18') is in contact with the chromatographic medium (11') through liquid collector (19'); so that filtering of the sample occurs after the conjugate is dissolved; or alternatively, the conjugate can be dissolved by adding buffer prior to adding a blood sample, typically through Port-2.

Another embodiment of a test strip according to the present invention is shown generally in FIG. 8. In general, FIG. 8 is a variation of the test strip according to the present invention shown in FIG. 3 but one in which the sample reacts with conjugate before reaching the sample filter, at least for sample applied to the conjugate pad, typically through Port-2. In this embodiment, the chromatographic strip (9') has a first end (10') and a second end (11'), a sample filter (18'), a fluid collector (19'), and a conjugate pad (13'), all situated at the second end (11') of the chromatographic strip (9'), together with a first sample filter (12'), at least one absorbent pad (15'), and optionally a second absorbent pad (16') that is in capillary contact with the first absorbent pad (15'), all situated at the first end (10') of the chromatographic strip (9'). Additionally, a third absorbent pad can optionally be used. The test strip of FIG. 8 has capture and control bands as in FIG. 3 (not shown in FIG. 8). Sample can be applied to the conjugate pad (13') as well as to the first sample filter (12'). The sample filter (18') and the fluid collector (19') can be constructed of the same macroporous material, but this is not required. It is preferred that the sample filter (18') have the same pore size as the conjugate pad (13'), and that the fluid collector (19') have a smaller pore size. The capillary gradient is therefore (19')>(18')>(13') because of the contact with (9'). In operation of the device of FIG. 8 when the device is used to perform a bidirectional assay, sample is applied to both the conjugate pad (13') as well as to the first sample filter (12'); the first sample filter (12') is typically accessed through Port-1 and the conjugate pad (13') is typically accessed through Port-2.

D. FIG. 9

Figure 9:
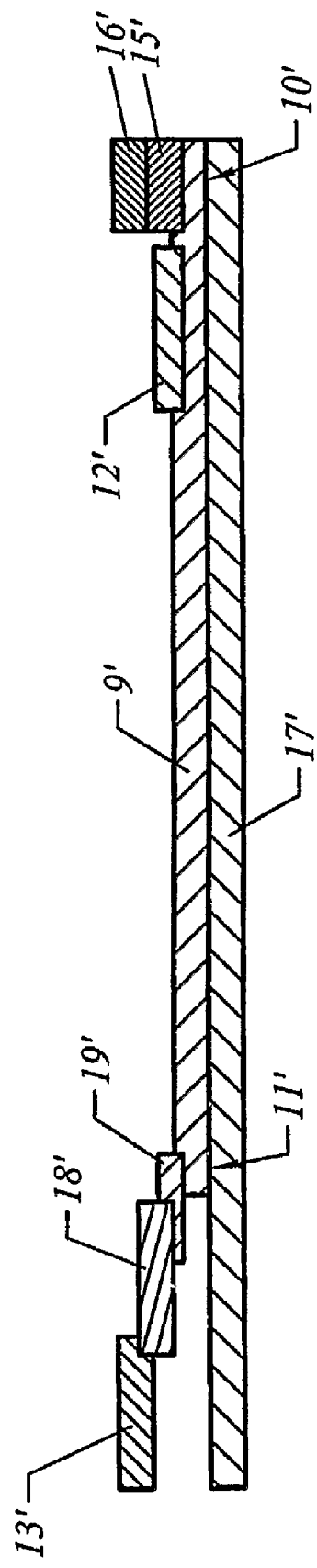
FIG. 9 is a side view of an alternative embodiment of the test strip generally similar to that of FIG. 4 but one in which the sample filter (18') is in contact with the chromatographic medium (11') through liquid collector (19'); so that filtering of the sample occurs after the conjugate is dissolved; or alternatively, the conjugate can be dissolved by adding buffer prior to adding a blood sample, typically through Port-2.

Still another embodiment of a test strip according to the present invention is shown generally in FIG. 9. In general, FIG. 9 is a variation of the test strip according to the present invention shown in FIG. 4 but one in which the sample reacts with conjugate before reaching the sample filter, at least for sample applied to the conjugate pad, typically through Port-2, as shown above for FIG. 8. The test strip of FIG. 9 has capture and control bands as in FIG. 4 (not shown in FIG. 9). The test strip of FIG. 9 is similar to that of FIG. 8 except that the sample pad (12') is in direct contact with the chromatographic strip (9') and is located further away from the first end (10') of the chromatographic strip (9') than are the absorbers (15') and (16'). By contrast, in the test strip of FIG. 8, the absorbers (15') and (16') are stacked atop the sample pad (12') such that the surface of the sample pad (12') is partially covered by the absorbers (15') and (16'). Additionally, a third absorbent pad can optionally be used. Sample can be applied to the conjugate pad (13') as well as to the first sample filter (12'). The sample filter (18') and the fluid collector (19') can be constructed of the same macroporous material, but this is not required. It is preferred that the sample filter (18') have the same pore size as the conjugate pad (13'), and that the fluid collector (19') have a smaller pore size. The capillary gradient is therefore (19')>(18')>(13') because of the contact with (9'). In operation of the device of FIG. 9 when the device is used to perform a bidirectional assay, sample is applied to both the conjugate pad (13') as well as to the first sample filter (12'); the first sample filter (12') is typically accessed through Port-1 and the conjugate pad (13') is typically accessed through Port-2.

E. FIG. 10

Figure 10:
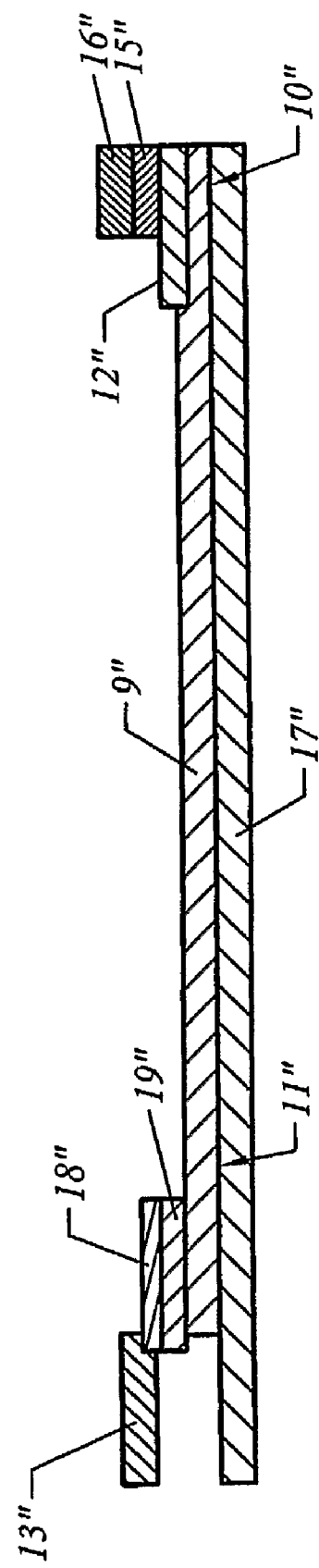
FIG. 10 is a side view of another alternative embodiment of a test strip generally similar to that of FIGS. 3 and 8, but one in which the sample filter (18") is fully on the top of liquid collector (19"), and in contact with the chromatographic medium (11") through liquid collector (19"); so that filtering of the sample occurs after the conjugate is dissolved; or alternatively, the conjugate can be dissolved by adding buffer prior to adding a blood sample, typically through Port-2.

Yet another embodiment of a test strip according to the present invention is shown generally in FIG. 10. In general, FIG. 10 is a variation of the test strip according to the present invention shown in FIG. 3 but one in which, stacked atop the second end of the chromatographic strip, are, in order, a fluid collector, a sample filter, and a conjugate pad. Typically, the fluid collector and the sample filter are in line, and the conjugate pad is offset so that it partially overlaps the sample filter. In this embodiment, the chromatographic strip (9") has a first end (10") and a second end (11"), a sample filter (18"), optionally, a fluid collector (19"), and a conjugate pad (13"), all situated at the second end (11") of the chromatographic strip (9"), together with a buffer pad (12"), at least one absorbent pad (15"), and optionally a second absorbent pad (16") that is in capillary contact with the first absorbent pad (15"), all situated at the first end (10") of the chromatographic strip (9"). Additionally, a third absorbent pad can optionally be used. The test strip of FIG. 10 has capture and control bands as in FIG. 3 (not shown). Sample can be applied to the conjugate pad (13"). The sample filter (18") and the fluid collector (19") can be constructed of the same macroporous material, but this is not required. It is preferred that the sample filter (18") have a pore size smaller than the conjugate pad (13"), and that the fluid collector (19") have a smaller pore size than the sample filter (18"). The capillary gradient is therefore (18")>(19")>(13") because of the contact with (9"). In operation, the following sequence is followed: (1) optionally prewet the chromatographic strip (9") from the buffer pad (12") at the first end; (2) add sample to the conjugate pad, allow the fluid to flow from the conjugate pad onto the sample filter (18"), allow the fluid to flow from the sample filter onto the optional fluid collector (19") or directly onto the chromatographic strip (9") in a direction towards the second end (11"), past the capture and control bands, and allow the analyte to be captured at the capture band.

F. FIG. 11

Figure 11:
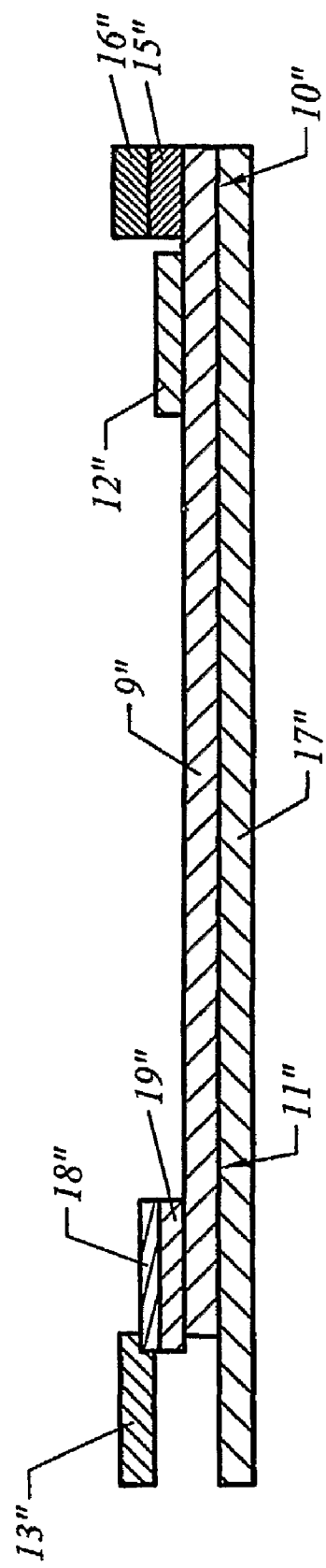
FIG. 11 is a side view of another alternative embodiment of a test strip generally similar to that of FIGS. 4 and 9, but one in which the sample filter (18") is fully on the top of liquid collector (19"), and in contact with the chromatographic medium (11") through liquid collector (19"); so that filtering of the sample occurs after the conjugate is dissolved; or alternatively, the conjugate can be dissolved by adding buffer prior to adding a blood sample, typically through Port-2.

Similarly, FIG. 11 shows an embodiment generally similar to that of FIG. 10 except that the relationship of the buffer pad (12"), the absorbent pads (15", 16") and the first end (10") of the chromatographic strip (9") is as shown in FIG. 4 or FIG. 9. The operation of the device of FIG. 11 is substantially similar to that of FIG. 10.

G. FIG. 12

Figure 12:
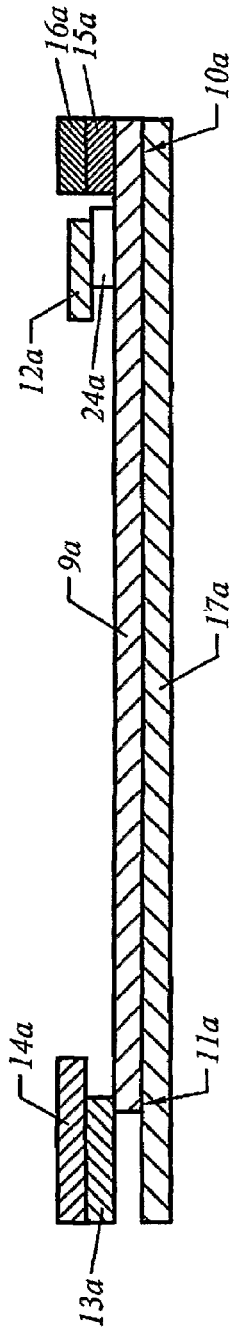
FIG. 12 is a side view of another alternative embodiment of a test strip generally similar to that of FIG. 2, but employing double-sided tape in the first end under sample filter or buffer pad. The double-sided tape can also be applied in a similar pattern to the devices of FIGS. 4, 4a, 4b, 9 and 11, for example.

FIG. 12 shows an embodiment generally similar to that of FIG. 4 except that a double-sided adhesive tape (24a) is interposed between the sample filter (12a) and the chromatographic strip (9a). The double-sided adhesive tape (24a) is intended to control the flow from the sample filter (12a) and to insure that flow from the sample filter (12a) proceeds toward the second end (11a) of the chromatographic strip (9a) and is temporarily delayed from proceeding toward the first end (10a) of the chromatographic strip (9a). In the device of FIG. 12, the chromatographic strip (9a) has a first end (10a) and a second end (11a), a buffer pad (14a), and a conjugate pad (13a), all situated at the second end (11a) of the chromatographic strip (9a), together with a sample filter (12a), at least one absorbent pad (15a), and optionally a second absorbent pad (16a) that is in capillary contact with the first absorbent pad (15a), all situated at the first end (10a) of the chromatographic strip (9a). Additionally, a third absorbent pad can optionally be used. The test strip of FIG. 12 has capture and control bands as in FIG. 3 (not shown). The sample can be applied to the sample filter (12a). The chromatographic strip (9a) can be backed with a backing (17a).

In the device of FIG. 12, sample applied to the sample filter (12a) enters the chromatographic strip (9a) and flows toward the second end (11a) of the chromatographic strip (9a). This is the first direction of flow in a bidirectional assay as described above. The adhesive tape (24a) ensures that sample flowing from the sample filter (12a) does not flow toward the first end (10a) of the chromatographic strip (9a) until a substantial amount of fluid has flowed toward the second end. In the second direction of flow in the bidirectional assay, buffer is applied to the buffer pad (14a). The buffer then flows through the conjugate pad (13a) to resolubilize the conjugate, which then flows through the chromatographic strip (9a) from the second end (11a) to the first end (10a), the flow being driven by the absorbers (15a, 16a).

Other alternatives of devices according to FIG. 12 are possible. For example, instead of sample, buffer can be applied to the first end (10a) of the chromatographic strip (9a). In that alternative, sample is applied to the second end (11a) of the chromatographic strip (9a); the conjugate pad (13a) is located so that it receives fluid from a sample filter replacing the buffer pad (14a) as described above. In other alternatives, the conjugate can be can be added separately such as in a buffer, or can be located near the second end (11a) of the chromatographic strip (9a) itself. In this alternative, in which the sample is applied to the second end (11a) of the chromatographic strip (9a), the sample filter (12a) is typically replaced with a buffer pad.

The double-sided tape (24a) can be completely situated under the sample filter (12a) or can, alternatively, be extended in the direction of the first end (10a) of the chromatographic strip (9a). When the double-sided tape (24a) is completely situated under the sample filter (12a), its typical surface dimensions are 5 mm×5 mm; its typical thickness is about 0.001 inch (0.0025 cm). When the double-sided tape (24a) is extended in the direction of the first end (10a) of the chromatographic strip (9a), its typical surface dimensions are 5 mm×7.5 mm or 5 mm×10 mm (for whole blood assays); its typical thickness is about 0.001 inch (0.0025 cm). A suitable material for the double-sided tape (24a) is polyester; a suitable polyester is manufactured by Adhesives Research, with the adhesive layers as described below; alternative materials are manufactured by other adhesives producers. The double-sided tape (24a) is coated with an adhesive on both sides. A particularly suitable adhesive is an inert, non-migratory acrylic adhesive. Other synthetic or natural materials could be used for the tape if they did not absorb the liquid. Any adhesive employed should lack any chemical or biochemical activity that would cause interaction with any component of the sample or the buffer. The thickness of the adhesive layer on each side is typically about 0.001 inch (0.0025 cm)

A first example of the dimensions of a device constructed according to FIG. 12 is as follows. These dimensions are particularly suitable for a device intended for the assay of an analyte in serum or plasma. The dimensions of the double-sided tape (24a) are 5 mm wide (the width of the strip)×5 mm long. The Port-1 buffer pad (12a) in FIG. 12 (5×7.5 mm) extends 3.5 mm past the end of the double-sided tape (24a) toward the second end (11a) of the chromatographic strip (9a). Toward the first end (10a) of the chromatographic strip (9a), the double-sided tape extends past the end of the Port-1 buffer pad (12a) by 1 mm. This ensures that liquid cannot flow from the Port-1 buffer pad (12a) over the chromatographic strip (9a) into the absorbent pads (15a, 16a) but must flow under the tape to reach the absorbent pads.

A second example of the dimensions of a device constructed according to FIG. 12 is as follows. These dimensions are particularly suitable for a device intended for the assay of an analyte using a whole blood sample. This device has a similar construction, but the Port-1 sample pad (12a) is 5×10 mm, so the double-sided tape (24a) is 5 mm wide×10 mm long. The Port-1 sample pad (12a) extends 2 mm past the end of the double sided tape (24a) toward the second end (11a) of the chromatographic strip (9a). Toward the first end (10a) of the chromatographic strip (9a), the double-sided tape (24a) extends past the end of the Port-1 sample pad (12a) by 2 mm.

The double-sided tape as used in the device of FIG. 12 can also be used in the devices of FIGS. 2, 4, 9, and 11, for example, in the same alternative orientations as in the device of FIG. 12.

Accordingly, yet another aspect of the invention is a test strip for a lateral flow assay for detection of at least one analyte in a sample, comprising:

(1) a chromatographic strip comprising a first end and a second end, at least one capture band comprising an immobilized capture agent for capturing the at least one analyte, and at least one control band comprising an immobilized control agent;

(2) a conjugate pad, wherein the conjugate pad is in capillary contact with the second end of the chromatographic strip, and wherein the conjugate pad comprises a mobilizable detectable agent that is capable of binding to the at least one analyte or to the capture agent after capturing the analyte;

(3) a fluid-impermeable barrier in direct contact with the first end of the chromatographic strip;

(4) a sample filter, wherein the sample filter is in capillary contact with the first end of the chromatographic strip and is in direct contact with the fluid-impermeable barrier such that flow from the sample filter in the direction of the first end of the chromatographic strip is substantially delayed, and wherein the sample filter optionally comprises an agglutinating agent;

(5) optionally, a buffer pad situated at the second end of the chromatographic strip that is in direct contact with the conjugate pad;

(6) a first absorber situated at the first end of the chromatographic strip that is in direct contact with the chromatographic strip; and (7) optionally, a second absorber that, if present, is in direct contact with the first absorber; wherein the test strip allows detection with or without quantitation of an analyte in a sample containing whole cells.

Accordingly, yet another aspect of the invention is a test strip for a lateral flow assay for detection of at least one analyte in a sample, comprising:

(1) a chromatographic strip comprising a first end and a second end, at least one capture band comprising an immobilized capture agent for capturing the at least one analyte, and at least one control band comprising an immobilized control agent;

(2) a conjugate pad, wherein the conjugate pad is in direct capillary contact with the second end of the chromatographic strip, and wherein the conjugate pad comprises a mobilizable detectable agent that is capable of binding to the at least one analyte or to the capture agent after capturing the analyte;

(3) first and second sample filters, wherein each of the first and second sample filters optionally comprises an agglutinating agent, and each of the first and second sample filters is in capillary contact with the chromatographic strip, the first sample filter being located at or near the first end of the chromatographic strip and the second sample filter being located adjacent to the second end of the chromatographic strip;

(4) a fluid collector that is situated between the second sample filter and the conjugate pad such that it is in direct contact with both the second sample filter and the conjugate pad;

(5) a fluid-impermeable barrier in direct contact with the first end of the chromatographic strip and that is in direct contact with the first sample filter such that flow from the first sample filter in the direction of the first end of the chromatographic strip is substantially delayed;

(6) a first absorber situated at the first end of the chromatographic strip that is in direct contact with the chromatographic strip, the first absorber being located closer to the first end of the chromatographic strip than the first sample filter; and (7) optionally, a second absorber that, if present, is in direct contact with the first absorber; wherein the test strip allows detection with or without quantitation of an analyte in a sample containing whole cells.

Accordingly, still another aspect of the invention is a test strip for a lateral flow assay for detection of at least one analyte in a sample, comprising:

(1) a chromatographic strip comprising a first end and a second end, at least one capture band comprising an immobilized capture agent for capturing the at least one analyte, and at least one control band comprising an immobilized control agent;

(2) first and second sample filters, wherein each of the first and second sample filters optionally comprises an agglutinating agent, and each of the first and second sample filters is in capillary contact with the chromatographic strip, the first sample filter being located at or near the first end of the chromatographic strip and the second sample filter being located adjacent to the second end of the chromatographic strip;

(3) a fluid collector that is situated between the second sample filter and the chromatographic strip such that it is in direct contact with both the second sample filter and the chromatographic strip;

(4) a conjugate pad situated at the second end of the chromatographic strip and that is in direct contact with the second sample filter and indirect contact with the fluid collector, and wherein the conjugate pad comprises a mobilizable detectable agent that is capable of binding to the at least one analyte or to the capture agent after capturing the analyte;

(5) a fluid-impermeable barrier in direct contact with the first end of the chromatographic strip and that is in direct contact with the first sample filter such that flow from the first sample filter in the direction of the first end of the chromatographic strip is substantially delayed;

(6) a first absorber situated at the first end of the chromatographic strip that is in direct contact with the chromatographic strip, the first absorber being located closer to the first end of the chromatographic strip than the first sample filter; and (7) optionally, a second absorber that, if present, is in direct contact with the first absorber; wherein the test strip allows detection with or without quantitation of an analyte in a sample containing whole cells.

In this particular arrangement, each of the conjugate pad, second sample filter, and fluid collector can be offset so that the conjugate pad partially overlaps the second sample filter and the second sample filter partially overlaps the fluid collector, as shown in FIG. 9. Alternatively, the conjugate pad can partially overlap the second sample filter, while the second sample filter substantially completely overlaps the fluid collector, as shown in FIG. 11. Other arrangements are possible.

H. FIG. 13

FIG. 13 shows an embodiment generally similar to that of FIG. 3 except that a double-sided adhesive tape (24b) is interposed between the sample filter (12b) and the chromatographic strip (9b). The double-sided adhesive tape (24b) is intended to control the flow from the sample filter (12b) and to insure that flow from the sample filter (12b) proceeds toward the second end (11b) of the chromatographic strip (9b) and is delayed from proceeding toward the first end (10b) of the chromatographic strip (9b). In the device of FIG. 13, the chromatographic strip (9b) has a first end (rob) and a second end (11b), a conjugate pad (13b), a second sample filter (18b), and a fluid collector (19b), all situated at the second end (11b) of the chromatographic strip (9b), together with a first sample filter (12b), at least one absorbent pad (15b), and optionally a second absorbent pad (16b) that is in capillary contact with the first absorbent pad (15b), all situated at the first end (10b) of the chromatographic strip (9b). Additionally, a third absorbent pad can optionally be used. The test strip of FIG. 13 has capture and control bands as in FIG. 3 (not shown). Sample can be applied to the first sample filter (12b) and/or to the second sample filter (18b). The chromatographic strip (9b) can be backed with a backing (17b).

In the device of FIG. 13, sample applied to the first sample filter (12b) enters the chromatographic strip (9b) and flows toward the second end (11b) of the chromatographic strip (9b). This is the first direction of flow in a bidirectional assay as described above. The adhesive tape (24b) ensures that sample flowing from the first sample filter (12b) does not flow toward the first end (10b) of the chromatographic strip (9b). In the second direction of flow in the bidirectional assay, sample is applied to the conjugate pad (13b). The sample then flows through the second sample filter (18b) and the fluid collector (19b) to reach the chromatographic strip (9b), flowing from the second end (11b) to the first end (10b), the flow being driven by the absorbers (15b, 16b).

Other alternatives of devices according to FIG. 13 are possible. For example, instead of sample, buffer can be applied to the second end (11b) of the chromatographic strip (9b). In that alternative, sample is applied to the first end (10b) of the chromatographic strip (9b). However, it is generally preferred to apply sample to the second end (11b) of the chromatographic strip (9b), rather than buffer, as, in most applications, this increases the sensitivity. That is because if sample is applied only to Port-1, i.e., to the first end (10b) of the chromatographic strip (9b), the volume of sample flowing past the capture and control bands from Port-1 is only about $1/100$ of the volume of sample flowing past the capture and control bands from Port-2. Thus if buffer is added to Port-2 instead of sample, then the effective sample size decreases by a factor of about 100, and therefore the sensitivity diminishes by the same factor. In another alternative, the conjugate can be located within the sample filter in resolubilizable form, can be added separately such as in a buffer, or can be located near the second end (11b) of the chromatographic strip (9b) itself.

The double-sided tape (24b) can be completely situated under the first sample filter (12b) or can, alternatively, be extended in the direction of the first end (10b) of the chromatographic strip (9b). When the double-sided tape (24b) is completely situated under the first sample filter (12b), its typical surface dimensions are 5 mm×5 mm; its typical thickness is about 0.001 inch (0.0025 cm). When the double-sided tape is extended in the direction of the first end (10b) of the chromatographic strip (9b), its typical surface dimensions are 5 mm×7.5 mm or 5 mm×10 mm as described above. A suitable material for the double-sided tape (24b) is polyester; a suitable polyester is manufactured by Adhesives Research, with the adhesive layers as described below; alternative materials are manufactured by other adhesives manufacturers. The double-sided tape (24b) is coated with an adhesive on both sides. A particularly suitable adhesive is an inert, non-migratory acrylic adhesive. The thickness of the adhesive layer on each side is typically about 0.001 inch (0.0025 cm).

The double-sided tape as used in the device of FIG. 13 can also be used in the devices of FIGS. 3, 3A, 3B, 8, and 10, for example.

Accordingly, another aspect of the invention is a test strip for a lateral flow assay for detection of at least one analyte in a sample, comprising:

(1) a chromatographic strip comprising a first end and a second end, at least one capture band comprising an immobilized capture agent for capturing the at least one analyte, and at least one control band comprising an immobilized control agent;

(2) a conjugate pad, wherein the conjugate pad is in direct capillary contact with the second end of the chromatographic strip, and wherein the conjugate pad comprises a mobilizable detectable agent that is capable of binding to the at least one analyte or to the capture agent after capturing the analyte;

(3) first and second sample filters, wherein each of the first and second sample filters optionally comprises an agglutinating agent, and each of the first and second sample filters is in capillary contact with the chromatographic strip, the first sample filter being located at or near the first end of the chromatographic strip and the second sample filter being located adjacent to the second end of the chromatographic strip;

(4) a fluid collector that is situated between the second sample filter and the conjugate pad such that it is in direct contact with both the second sample filter and the conjugate pad;

(5) a fluid-impermeable barrier in direct contact with the first end of the chromatographic strip and that is in direct contact with the first sample filter such that flow from the first sample filter in the direction of the first end of the chromatographic strip is substantially delayed;

(6) a first absorber situated at the first end of the chromatographic strip that is in direct contact with the first sample filter and in indirect contact with the chromatographic strip; and (7) optionally, a second absorber that, if present, is in direct contact with the first absorber; wherein the test strip allows detection with or without quantitation of an analyte in a sample containing whole cells.

Yet another embodiment of a test device according to the present invention is a test strip for a lateral flow assay for detection of at least one analyte in a sample, comprising:

(1) a chromatographic strip comprising a first end and a second end, at least one capture band comprising an immobilized capture agent for capturing the at least one analyte, and at least one control band comprising an immobilized control agent;

(2) first and second sample filters, wherein each of the first and second sample filters optionally comprises an agglutinating agent, and each of the first and second sample filters is in capillary contact with the chromatographic strip, the first sample filter being located at or near the first end of the chromatographic strip and the second sample filter being located adjacent to the second end of the chromatographic strip;

(3) a fluid collector that is situated between the second sample filter and the chromatographic strip that it is in direct contact with both the second sample filter and the chromatographic strip;

(4) a conjugate pad situated at the second end of the chromatographic strip and that is in direct contact with the second sample filter and indirect contact with the fluid collector, and wherein the conjugate pad comprises a mobilizable detectable agent that is capable of binding to the at least one analyte or to the capture agent after capturing the analyte;

(5) a fluid-impermeable barrier in direct contact with the first end of the chromatographic strip and that is in direct contact with the first sample filter such that flow from the first sample filter in the direction of the first end of the chromatographic strip is substantially delayed;

(6) a first absorber situated at the first end of the chromatographic strip that is in direct contact with the first sample filter and in indirect contact with the chromatographic strip; and (7) optionally, a second absorber that, if present, is in direct contact with the first absorber; wherein the test strip allows detection with or without quantitation of an analyte in a sample containing whole cells.

In this particular arrangement, each of the conjugate pad, second sample filter, and fluid collector can be offset so that the conjugate pad partially overlaps the second sample filter and the second sample filter partially overlaps the fluid collector, as shown in FIG. 8. Alternatively, the conjugate pad can partially overlap the second sample filter, while the second sample filter substantially completely overlaps the fluid collector, as shown in FIG. 10. Other arrangements are possible.

I. Specific Embodiments of FIGS. 14-19

Figure 14:
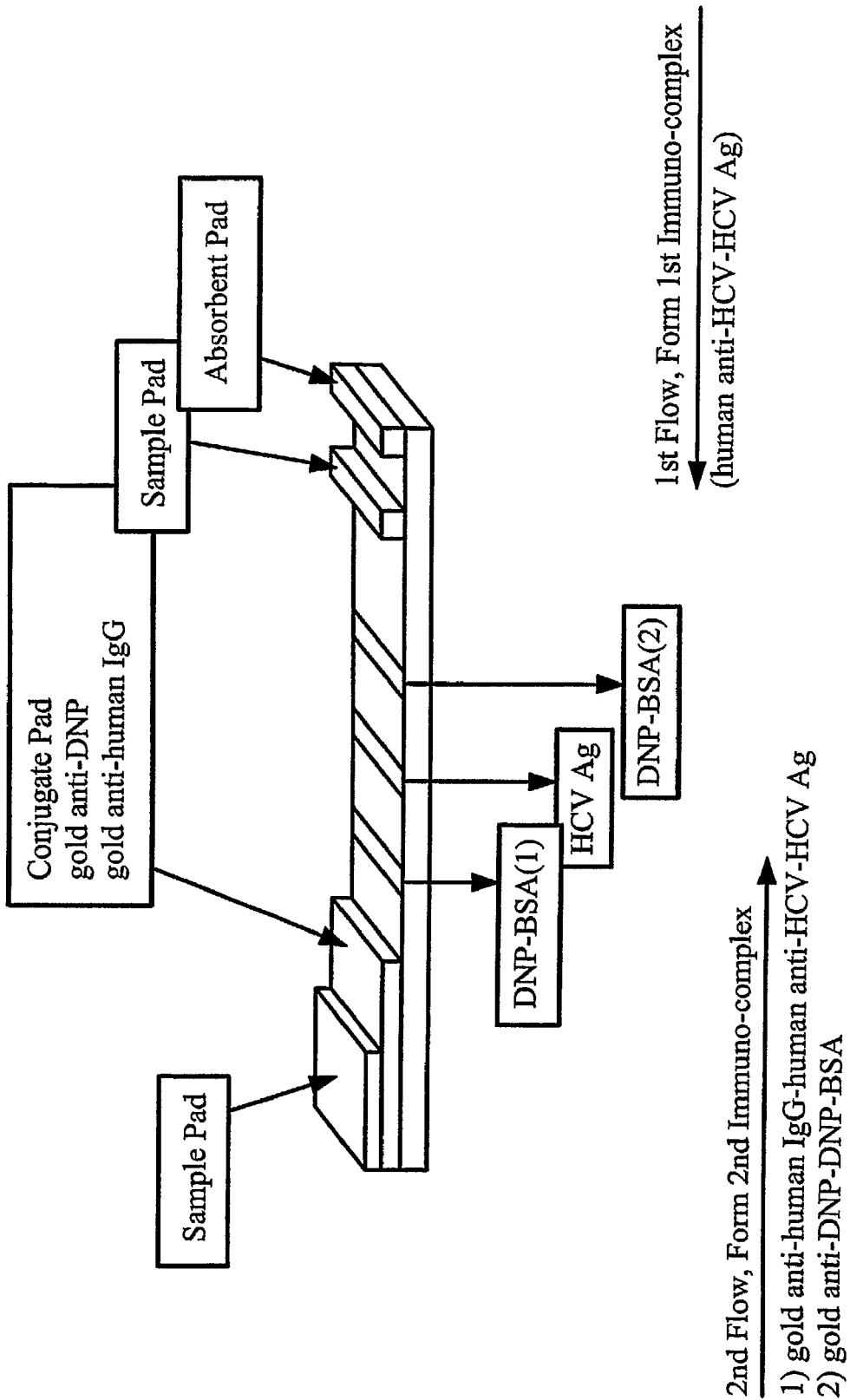
FIG. 14 is a detailed side view of an embodiment of a test strip capable of performing an indirect assay for human hepatitis C virus (HCV) using gold anti-DNP antibody and DNP-BSA as a control system.
Figure 15:
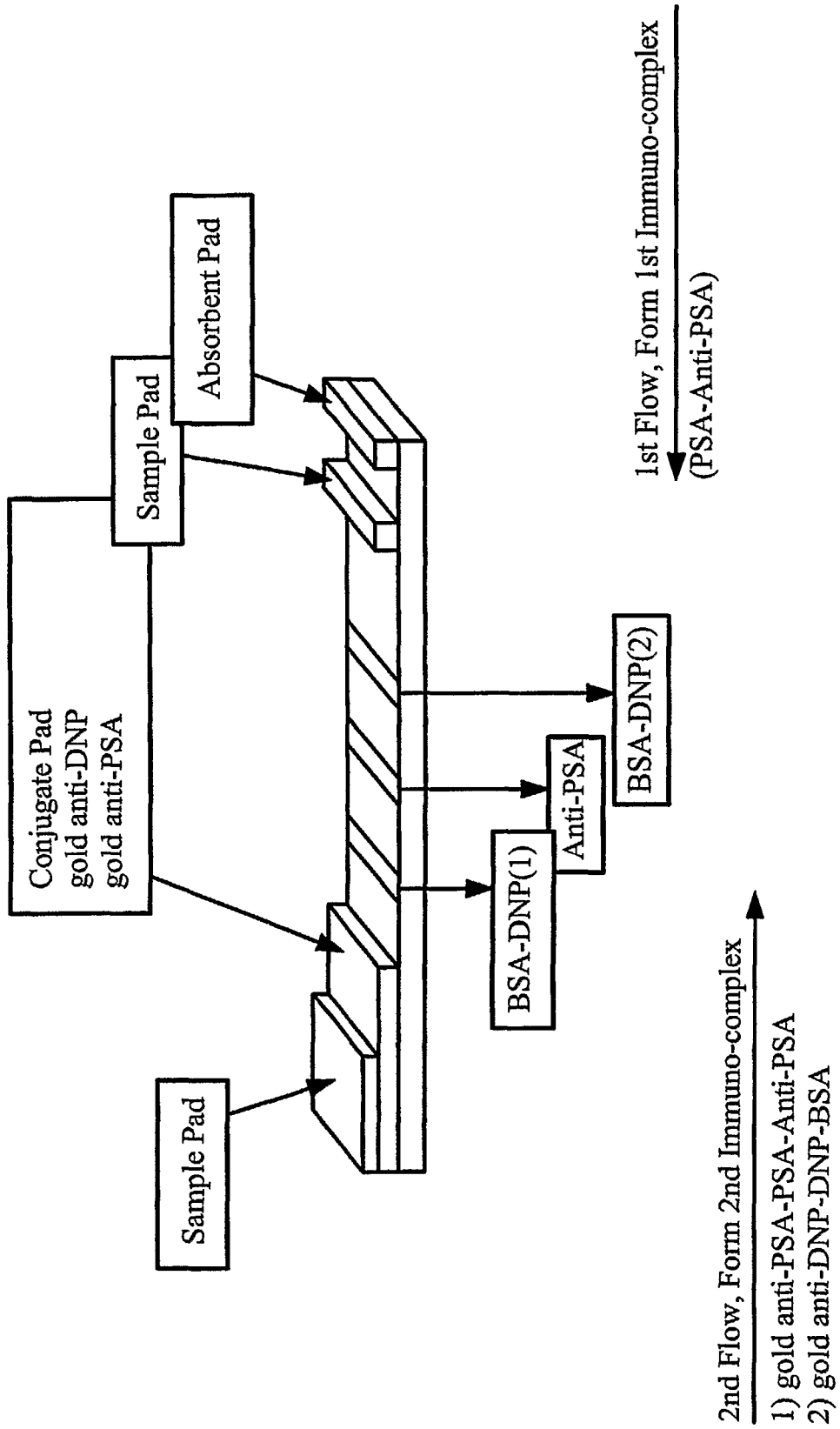
FIG. 15 is a detailed side view of an embodiment of a test strip capable of performing a sandwich assay for prostate specific antigen (PSA) using gold anti-DNP antibody and DNP-BSA as a control system.
Figure 16:
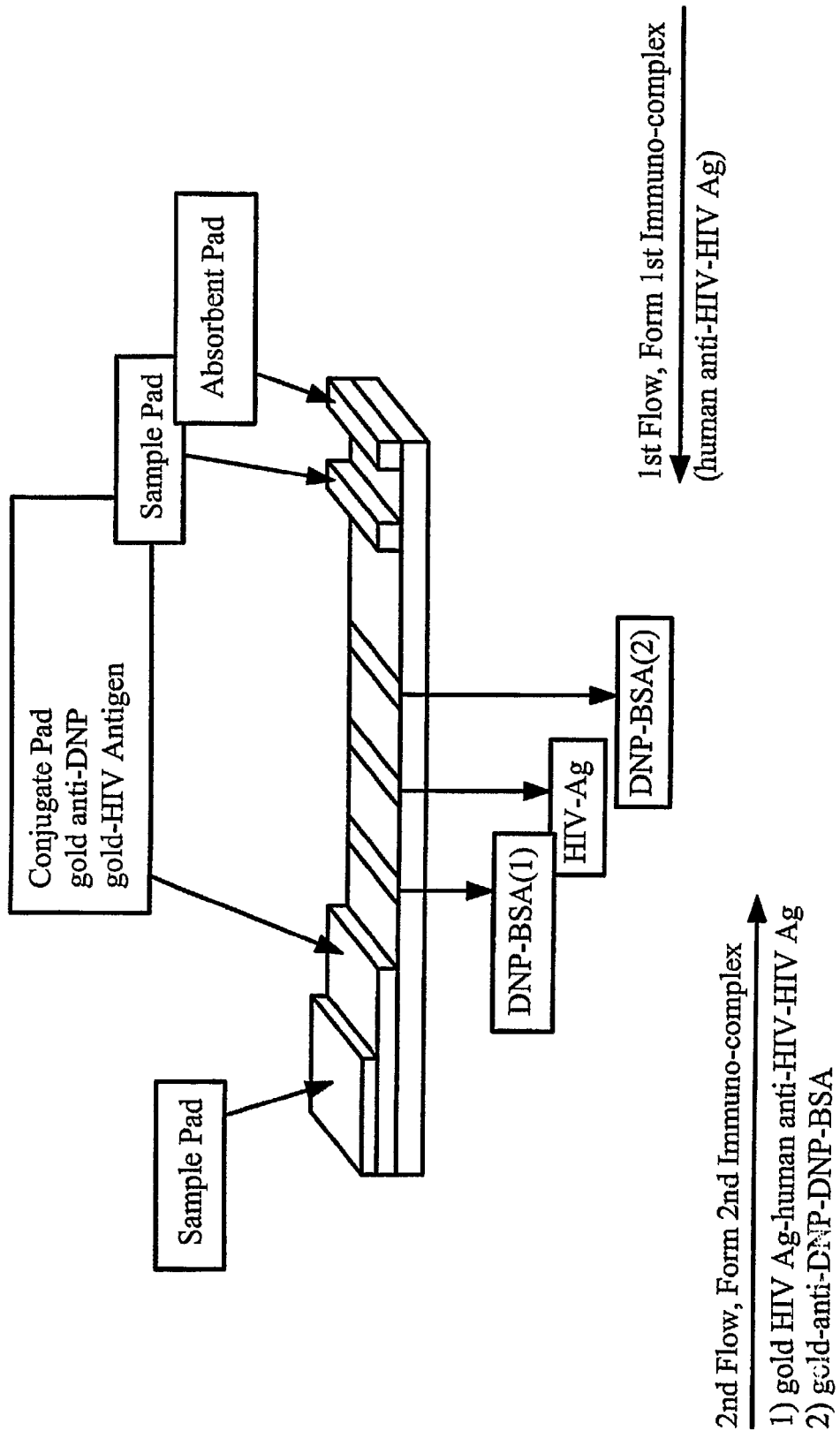
FIG. 16 is a detailed side view of an embodiment of a test strip capable of performing a sandwich assay for antibody specific for human HIV using gold anti-DNP antibody and DNP-BSA as a control system.
Figure 17:
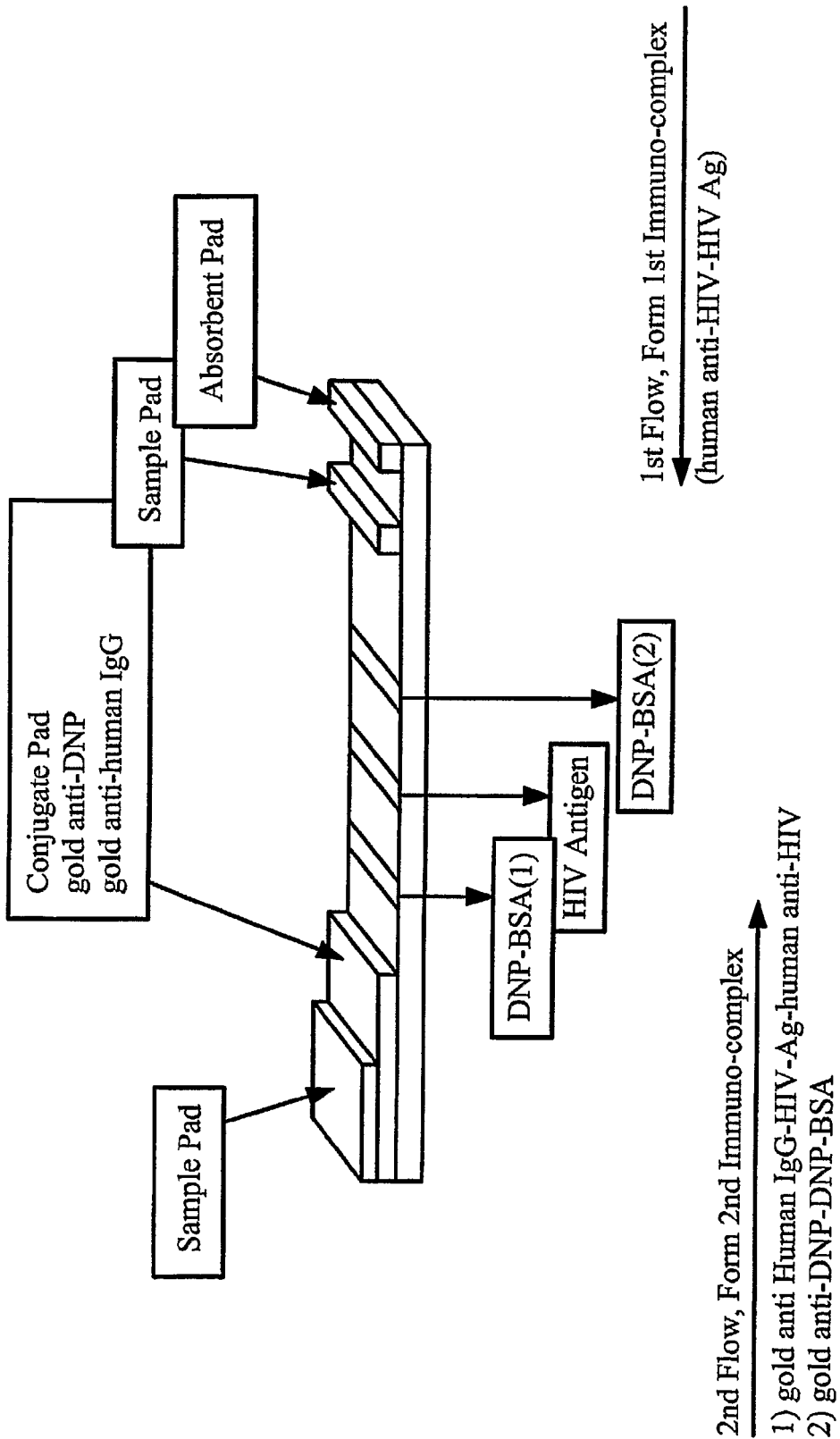
FIG. 17 is a detailed side view of an embodiment of a test strip capable of performing an indirect assay for antibody specific for human HIV using gold anti-DNP antibody and DNP-BSA as a control system.
Figure 18:
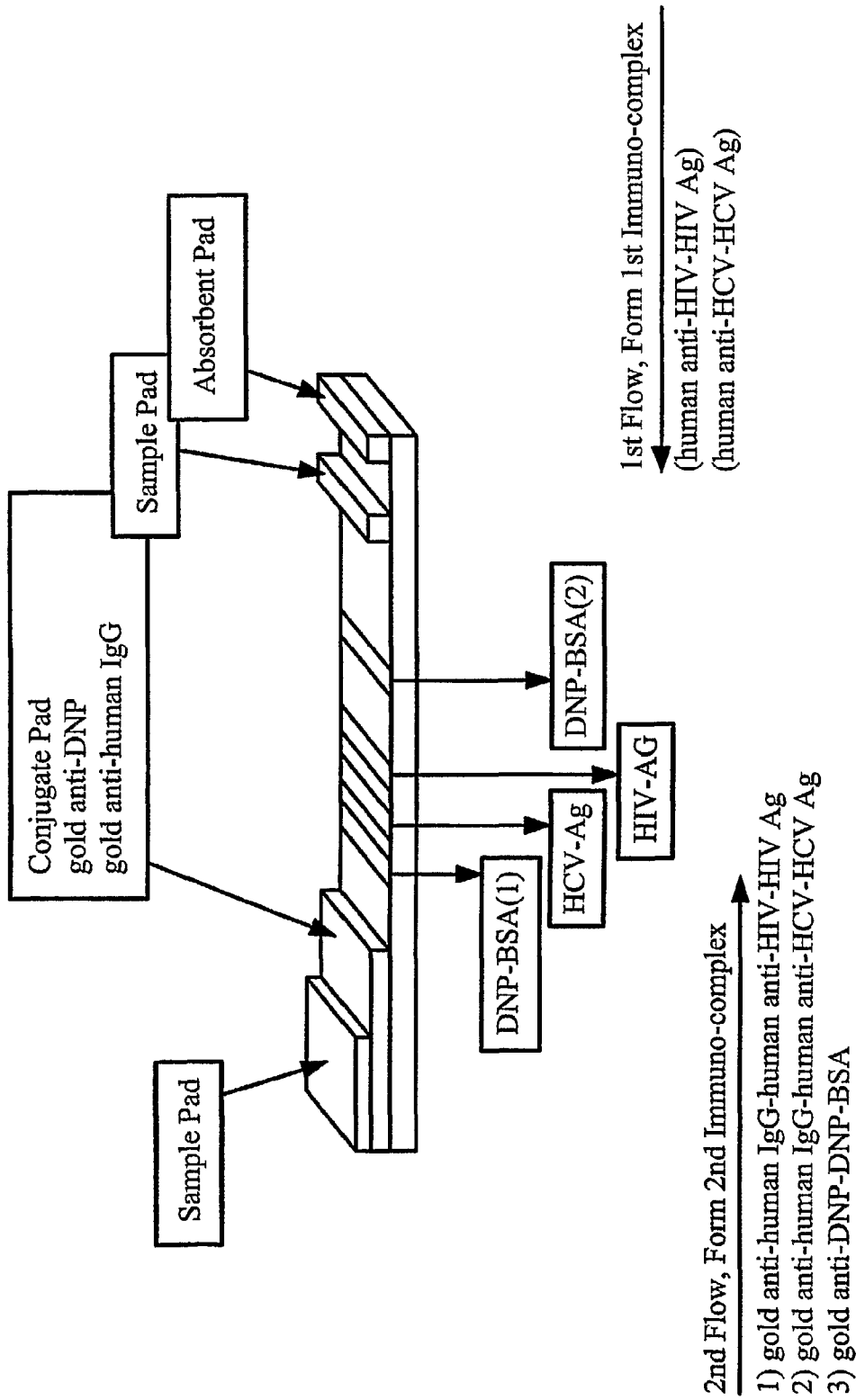
FIG. 18 is a detailed side view of an embodiment of a test strip capable of performing an indirect assay for antibody specific for human HIV and for antibody specific for HCV using gold anti-DNP antibody and DNP-BSA as a control system.
Figure 19:
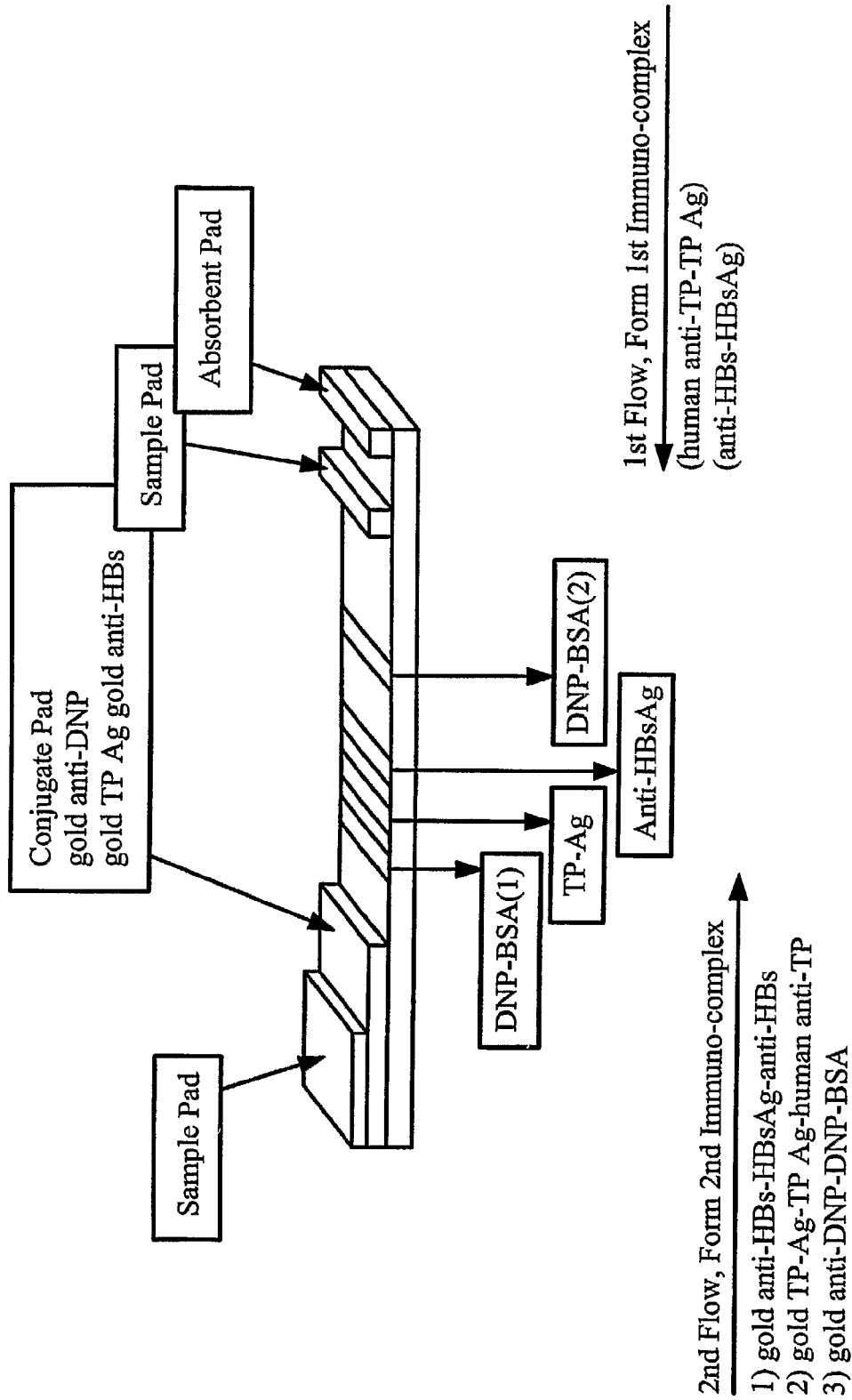
FIG. 19 is a detailed side view of an embodiment of a test strip capable of performing a sandwich assay for hepatitis B surface antigen (HBsAg) and for antibodies to *Treponema pallidum* using gold anti-DNP antibody and DNP-BSA as a control system.

Specific embodiments of test strips according to the present invention are illustrated in FIGS. 14-19. The devices of FIGS. 14-19 all use gold anti-DNP antibody and DNP-BSA as a control and operate in a bidirectional mode. FIG. 14 is a detailed side view of an embodiment of a test strip capable of performing an indirect assay for human hepatitis C virus (HCV). FIG. 15 is a detailed side view of an embodiment of a test strip capable of performing a sandwich assay for prostate specific antigen (PSA). FIG. 16 is a detailed side view of an embodiment of a test strip capable of performing a sandwich assay for antibody specific for human HIV. FIG. 17 is a detailed side view of an embodiment of a test strip capable of performing an indirect assay for antibody specific for human HIV. FIG. 18 is a detailed side view of an embodiment of a test strip capable of performing an indirect assay for antibody specific for human HIV and for antibody specific for HCV in the same sample. FIG. 19 is a detailed side view of an embodiment of a test strip capable of performing a sandwich assay for hepatitis B surface antigen (HBsAg) and for antibody to *Treponema pallidum* in the same sample.

I. Other General Embodiments

Accordingly, another embodiment of a test strip according to the present invention generally is a test strip for a lateral flow assay for detection of at least one analyte in a sample, comprising:

(1) a chromatographic strip comprising a first end and a second end, at least one capture band comprising an immobilized capture agent for capturing the at least one analyte, and at least one control band comprising an immobilized control agent;

(2) a conjugate pad, wherein the conjugate pad is in capillary contact with the second end of the chromatograph strip, and wherein the conjugate pad comprises a mobilizable detectable agent that is capable of binding to the at least one analyte or to the capture agent after capturing the analyte;

(3) a sample filter that is adjacent to the conjugate pad on the side closer to the second end, wherein the sample filter optionally comprises an agglutinating agent, and the sample filter is in capillary contact with the chromatographic strip;

(4) optionally a fluid collector that, if present, is situated between the sample filter and the chromatographic strip;

(5) optionally, a buffer pad situated at the first end of the chromatographic strip and is in capillary contact with the chromatographic strip;

(6) a first absorbent pad situated at the first end of the chromatographic strip that is in capillary contact with the chromatographic strip, either directly or indirectly; and (7) optionally, a second absorbent pad that, if present, is in capillary contact with the first absorbent pad; wherein the test strip allows detection with or without quantitation of an analyte in a sample containing whole cells.

Still more generally, another embodiment of a test strip according to the present invention is a test strip for a lateral flow assay for detection of at least one analyte in a sample, comprising:

(1) a chromatographic strip comprising a first end and a second end, at least one capture band comprising an immobilized capture agent for capturing the at least one analyte, and at least one control band comprising an immobilized control agent;

(2) a sample filter in capillary contact with the first end of the chromatographic strip;

(3) a fluid-impermeable barrier in direct contact with the first end of the chromatographic strip and that is in direct contact with the sample filter such that flow from the sample filter in the direction of the first end of the chromatographic strip is substantially delayed; and (4) means for providing a mobilizable detectable agent that is capable of binding to the at least one analyte or to the capture agent after capturing the analyte to the chromatographic strip such that the mobilizable detectable agent migrates through the chromatographic strip and contacts sample that has passed through the sample filter and also has migrated through the chromatographic strip;

wherein the test strip allows detection with or without quantitation of an analyte in a sample containing whole cells.

The materials assembled for the present invention and the arrangements of the components of the test strip confer a unique advantage to the present invention, enabling the use of small volume of samples, efficient filtering of cells including red blood cells, efficient dissolution of the detectable agents and the achievement of consistent results in determination of presence and quantity of analytes.

While the present invention provides advantages such as the efficient separation of red blood cells from the fluid in a sample and lack of dependency on cell volume, the present invention can also be used for determination and quantitation of one or more analytes in samples in which no cells are present or in which the cells present are not red blood cells. Hence, the samples to be tested include serum, plasma and whole blood.

VI. Interaction Between the Test Strip and Cassette

Test strips according to the present invention are typically intended for use with a cassette, such as that of FIG. 1, and are typically dimensioned to fit within the cassette of FIG. 1, so that the openings of the cassette of FIG. 1 can be used to apply reagents to the test strip, and so that the cassette of FIG. 1 can be placed with the test strip within it in a reader to obtain qualitative or quantitative results. However, test strips according to the present invention are not limited to use with a cassette, such as that of FIG. 1; other arrangements for application of reagents and for reading the results are possible and are within the scope of the invention.

Figure 5:
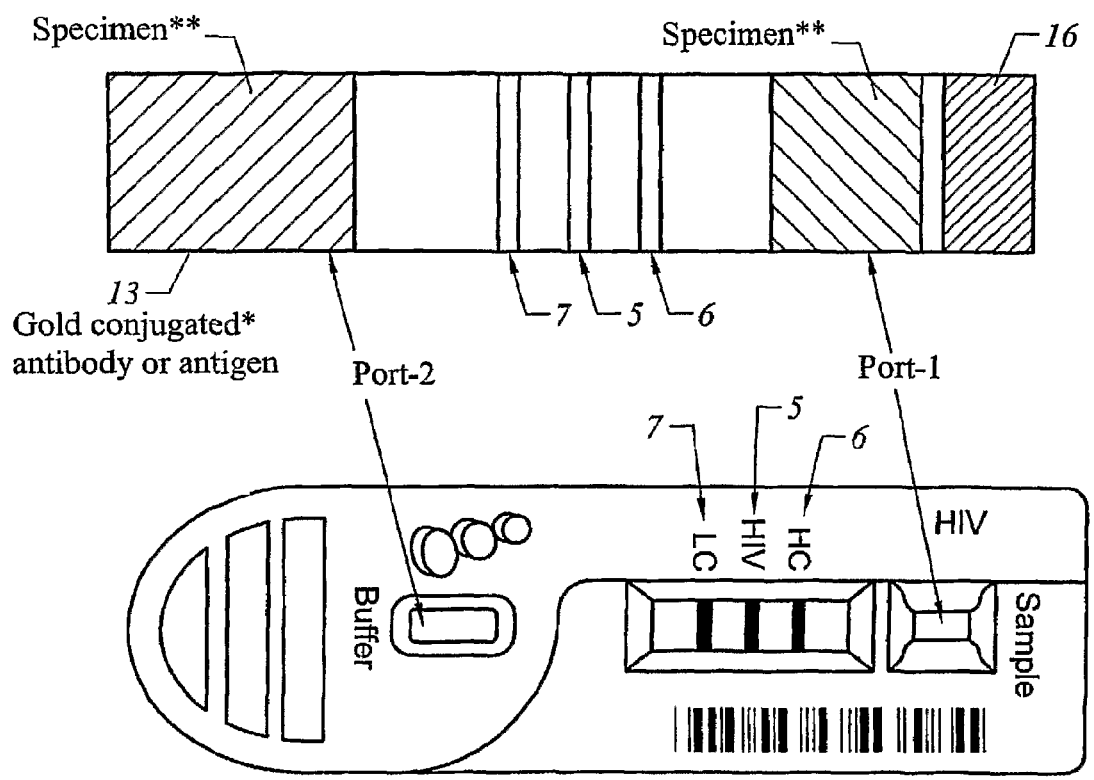
FIG. 5 is a top view of one embodiment of the test strip of the present invention and a top plan view of a cassette that may be used with the test strip, showing correspondence between the test strip and portions of the test strip that are visible in the cassette.

Referring to FIG. 5, FIG. 5 shows the correspondence between the top plan view of the test strip of the present invention and the cassette, such as that of FIG. 1, that may be used therewith. In this embodiment, the detectable agents may be incorporated into the chromatographic strip at the second end or may be present in a conjugate pad. When this strip configuration is used for a sandwich assay, a sample to be analyzed may be added to both Port-1 (2) and Port-2 (3); or alternatively, a sample may be added to Port-2 (3), but a reagent such as a buffer instead of a sample may be added to Port-1 (2). When it is used for an indirect assay, a sample may be added to Port-1 (2); a buffer may be added to Port-2 (3).

An example of a device that can be used to produce results from a test strip according to the present invention inserted into a cassette, as is shown in FIG. 5, is the device described in U.S. Pat. No. 6,136,610 to Polito et al., incorporated herein by this reference, and more particularly in FIGS. 1, 2, 3, 4, 5, 6, 7, 7A, and 8 of U.S. Pat. No. 6,136,610. This device is particularly suitable for detection of an analyte by measuring reflectance intensity (Density of Reflection or Dr) and by converting that measurement into Relative Intensity (RI). The device can comprise means for controlling the timing of the assay and a heating element for heating the test strip, as well as means for storing and communicating the results in digital form. The device can determine a baseline and correct for irregularities that might be present in the test strip. Although the device of U.S. Pat. No. 6,136,610 to Polito et al. is particularly suitable for measurement of analyte concentration by reflectance intensity, the device can be adapted for other measurements, such as fluorescence, radiation, or magnetic flux. For example, the optical sensors used in the device of U.S. Pat. No. 6,136,610 Polito et al. can be replaced with other types of sensors. The sensor codes can communicate in other modes other than through bar codes read by a bar code reader, such as RFID tags. Other modifications to the device of U.S. Pat. No. 6,136,610 can be made; for example, the communication outlet can include a connection to the internet by way of a dial-up modem connection or a broadband connection, as is known in the art. In another example, information that may be provided to the computer system can include parameters that reconfigure the assay tables of the memory resources and that are provided through a replacement memory chip such as an insertable memory chip, flash memory, memory stick, or other memory device. Still other variations are possible.

In another embodiment of the invention, the cassette or other receptacle containing a test strip according to the present invention can be inserted into an apparatus that can perform multiple tests simultaneously, such as 2 tests, 3 tests, 4 tests, 5 tests, 6 tests, or more. The apparatus can have multiple bays for insertion of multiple cassettes or other receptacles for performance of multiple tests. The apparatus can also include multiple sensors for automatically detecting addition of liquid such as a sample or a buffer to both Port-1 and Port-2 of the cassette. As used herein, the term "sensor" is defined broadly to include any device that can detect the addition of liquid to Port-1 and Port-2. The apparatus further includes means for controlling temperature of the cassettes held in the bay. This can be done by any conventional means of controlling temperature, such as a thermostat. This can include, for example, a camera or a spectral receptor, and is not limited to a device that detects the addition of liquid to Port-1 and Port-2 by a change in an electrical property such as conductance or capacitance. In one alternative, the apparatus can have different types of detection modules so that one could run tests with colloidal gold labels, chemiluminescent labels and fluorescent labels on the same instrument. Although this apparatus has been described in terms of an apparatus having multiple bays, an apparatus with a single bay and having the other features described is also part of the present invention and can also be used with test strips according to the present invention.

Accordingly, another embodiment of the present invention is an apparatus for performing an assay for detecting or determining an analyte on a test strip, the apparatus comprising:

(1) at least two bays, each bay holding a cassette according to the present invention;

(2) a sensor that detects addition of liquid to Port-1 and Port-2 of the cassette inserted into each bay;

(3) means for controlling temperature of the cassettes held in the bay; and (4) means for detecting or determining the analyte detected or determined on each test strip of each cassette and reporting each detection or determination of the analyte.

Still another embodiment of the present invention is an apparatus for performing an assay for detecting or determining an analyte on a test strip, the apparatus comprising:

(1) a bay holding a cassette according to the present invention;

(2) a sensor that detects addition of liquid to Port-1 and Port-2 of the cassette inserted into the bay;

(3) means for controlling temperature of the cassettes held in the bay; and (4) means for detecting or determining the analyte detected or determined on each test strip of the cassette and reporting each detection or determination of the analyte.

VII. Details of Assays Carried Out by Test Strips According to the Present Invention The method of conducting an indirect lateral flow assay using the test strip of the present invention can be illustrated by referring to FIG. 6. FIG. 6 shows the top plan view of one embodiment of the present invention, showing bidirectional lateral flow of sample and reagents in an assay, such as in the embodiment of FIG. 2. In this embodiment, a sample is applied onto a sample filter (12). Fluid from the sample filter (12) migrates to the chromatographic strip (9) at the first end (10) and flows in a first flow direction (21) past the capture band (5) and the control bands (6, 7) towards the second end (11) of the chromatographic strip (9). Between the control band (7) and the conjugate pad (13), fluid from the sample ceases flow in the first flow direction (21); if there is sufficient fluid remaining after the first flow, after the second liquid is applied onto Port-2 (3), the fluid remaining from the first flow will reverse and flow in the second flow direction (22) back towards the first end (10) of the chromatographic strip (9). The analyte in the sample, if present, is captured primarily at the capture band (5) during the course of the fluid flow in the first flow direction (21), and secondarily during the course of fluid flow in the second flow direction (22). The bidirectional lateral flow prewets the chromatography strip, so that the chemicals on its surface can be dissolved and distributed evenly before labeled reagents flow into this area; it also aids in washing contaminants away from the capture and control bands, reducing background noise in the assay. A reagent, such as a buffer or conjugate release buffer suitable for the assay, is applied to the buffer pad (14) in Port-2, in an amount sufficient to dissolve or release the conjugate. A particularly suitable conjugate release buffer is 1×PBS containing 0.1% Tween 20, 0.01% casein, 0.3% SDS, 0.2 mM EDTA and 0.1% sodium azide. The released conjugate migrates from the second end (11) of the chromatographic strip (9) in a second flow direction (22) towards the first end (10) of the chromatographic strip (9) and interacts with the analyte at the capture band (5). The conjugate is made relevant to the analyte to be tested. For example, for detection of human antibodies in a human blood sample, the conjugate can be an anti-human IgG, (or IgM when testing for human IgM), such as, but not limited to, goat anti-human IgG, rabbit anti-human IgG, or murine anti-human IgG conjugated to colloidal gold.

In the absence of an agglutinin in the sample filter (12) in the conduct of a bidirectional lateral flow assay, red blood cells present in a sample may leak onto the chromatographic strip (9) creating high background noise and therefore a reduced signal-to-noise ratio. The inventors herein have discovered that this background problem may be reduced significantly if a detergent, such as a non-ionic detergent, for example, TWEEN 20, is present in the conjugate release buffer, at a relatively high concentration, for example, at least about 0.1%. The combination of the detergent and conjugate release buffer aids in washing the red blood cells or lysed red blood cells away from the capture and control bands, and decreasing the non-specific binding of analyte to sample filter.

If an agglutinin is used in the sample filter (12), such as an anti-red blood cell antibody, to remove red blood cells, then the sample filter (12) is pretreated with a detergent, such as a non-ionic detergent, such as TWEEN 20. A low concentration of the detergent is used for this purpose, such as, for example, about 0.002%. The application of non-ionic detergent aids in changing the hydrophobic surface of the sample filter to slightly hydrophilic, so that the agglutinin could bind to the sample filter more tightly.

FIG. 7 illustrates the conduct of a sandwich assay of an embodiment of the present invention as shown in FIG. 4. An aliquot of a sample such as one containing red blood cells is applied to the first sample filter (12) at the first end (10) of the chromatographic strip (9). Fluid from this aliquot flows in the first flow direction (21) from the first end (10) of the chromatographic strip (9) towards the second end (11), flowing past the capture band (5) and the control bands (6, 7). The analyte, if present, is captured at the capture band (5). A second aliquot of the same sample is then applied to the second sample filter (18) at Port-2 (3) the second end (11) of the chromatographic strip (9). Fluid in the second sample filter (18) passes through a fluid collector (not shown) and a conjugate pad (13) to the second end (11) of the chromatographic strip (9), which then flows in the second flow direction (22) from the second end of the strip towards the first, flowing past the capture band (5) and control bands (6, 7). The analyte, if present, is also captured at the capture band (5), where the analyte and the detection reagent form a sandwich.

Alternatively, initial addition of sample to the sample pad at the first end (10) of the chromatographic strip (9) may be omitted and instead sample added directly to the second sample filter (18) at Port-2 (3) at the second end (11) of the chromatographic strip (9). Fluid in the sample filter (18) passes through a fluid collector (not shown) and a conjugate pad (13) to the second end (11) of the chromatographic strip (9), which then flows in the second flow direction from the second end of the strip towards the first, flowing past the capture band (5) and control bands (6, 7). The analyte, if present, is also captured at the capture band (5), where the analyte together with the detection reagent at the capture band form a sandwich. Typically, in this mode of operation, buffer is added to the first sample filter (12) so that the buffer flows in the first flow direction from the first end of the strip toward the second to prewet the strip.

Similar sequences of operation can be carried out with the device shown in FIG. 3.

As indicated above, test strips according to the present invention can be used to detect multiple analytes in a single assay. For example, if the sample contains two analytes, the chromatographic strip can then comprise two separate capture bands, each capture band comprising an immobilized capture agent that is specific for capturing one analyte but not the other. Alternatively, if the sample contains three analytes and the chromatographic strip can then comprise three separate capture bands, each capture band comprising an immobilized capture agent that is specific for capturing one analyte but not the other two. Those of ordinary skill in the art can select appropriate capture agents for combinations of analytes desired to be assayed in a single assay according to the nature of the analytes and the specificities of the capture agents, such as antibodies, for them.

The amount of analyte captured at the capture band can be quantitated as described in U.S. Pat. No. 6,136,610. However, other methods of quantitation are possible. Test strips according to the present invention can also be used for qualitative or semiquantitative determinations.

The components used herein in the Examples including the absorbent pad, the sample filter, the buffer pad, the chromatographic strip, and the conjugate pad have the properties set forth in Table 1, as specified by the manufacturer thereof. However, other alternative components can be used and are known in the art.

VIII. Analytes, Detecting Reagents and Buffers

A. Analytes

Suitable analytes include, but are not limited to antigens, antibodies, hormones, drugs, cell proteins, DNAs, cardiac markers, tumor or cancer markers, autoimmune disease markers, or any macromolecule that could raise antibodies. When the analyte is an antigen, the antigen can be an antigen associated with an infectious agent. The infectious agent can be a virus, a bacterium, a fungus, or a prion. When the infectious agent is a virus, the virus can be selected from the group consisting of HIV, hepatitis virus A, B, C, and D, herpes simplex virus, cytomegalovirus, papilloma virus, Ebola virus, SARS virus, Rhinovirus, and Vaccinia virus, but is not limited to those viruses. When the infectious agent is a bacterium, the bacterium can be a Gram-positive bacterium or a Gram-negative bacterium. The bacterium can be selected from the group consisting of *Bacillus anthracis, Escherichia coli, Helicobacter pylori, Neisseria gonorrheae, Salmonella* species, and *Shigella* species, but is not limited to those bacteria. When the infectious agent is a fungus, the fungus can be a *Mycosporum* species or an *Aspergillus* species, but is not limited to those fungi.

When the analyte is a hormone, typically it is selected from the group consisting of hCG, thyroxin, TSH, glucagons, insulin, relaxin, prolactin, luteinizing hormone, melanotropin, somatotropin, follicle-stimulating hormone, gastrin, bradykinin, vasopressin, and other releasing factors; however, other hormones of physiological or pathological interest can be the analyte.

When the analyte is a cancer or tumor marker, typically it is selected from the group consisting of prostate specific antigen (PSA), carcinoembryonic antigen (CEA), and α-fetoprotein; however, other cancer or tumor markers can be the analyte.

When the analyte is a cardiac marker, the cardiac marker is typically selected from the group consisting of Troponin-1, Troponin T, Creatine kinase-MB isoforms (CK-MB), myoglobin, C-reactive protein (CRP), fatty acid binding protein (FABP), glycogen phosphorylase isoenzyme BB (GPBB), B-type natriuretic peptide (BNP) and NT-pro-BNP; however, the analyte can be another cardiac marker.

Still other analytes can be assayed by test strips and methods according to the present invention. For example, tissue-specific cell surface markers can be assayed. Separation of cell populations based on these markers has been performed using lectins (Reisner and Sharon, Trends in Biochem Sci (TIBS) 29, 1980), blood leukocyte surface glycoproteins (Gahmberg and Anderssen, NYAS (1978) 312, in Fibroblast Surface Proteins eds. Vahery, Ruslahti and Mosher), estrogen steroid receptors (Thompson, Cancer Treatment Reports (1978) 63(2) 180, erythrocyte insulin receptors (Bhathena et al, Horm Metab Res (1981) 13:179), or multiple markers as in the case of lymphocytes. Further separation of subpopulations is possible based on markers identified with specific cell functions as in the case of the T lymphocytes (Reinberg and Schlossman, N Eng J Med (1980) 303:1153).

Similarly, tissue-shared cell surface markers can be assayed. Some cell surface markers are present on multiple cell types. An example of these are the Major Histocompatibility Complex Human Lymphocyte Antigen (HLA) system, LETS protein, p glycoprotein (Kartner et al, Science (1983) 221:1285) and transferrin receptors (Omary et al, Nature (London) (1980) 286:888).

Other analytes include viral-associated cell surface markers. Cell element antigens can also result from viral infection. The mumps H—N glycoprotein detectable by RIA, immunofluorescence and hemagglutination inhibition represents a viral marker on infected cells (Sever et al, Infect & Immun (1982) 35(1):179). Similarly, markers resulting from Herpes Simplex 1 and 2 infection are recognizable on the host cell surface by immunofluorescence (Stewart and Herrmann, "Herpes Simplex Virus" in Manual of Clinical Immunology, 2nd edition, edited by N. R. Rose and H. Friedman, American Society for Microbiology, Washington, D.C., 1980).

Still other analytes include tumor-specific cell surface markers. Neoplastic and oncogenic transformation results in the alteration of the cell phenotype as expressed in cell surface proteins. This can be observed as variations in the presence of antigens normally expressed on the cell surface, appearance of "altered self antigens," appearance of embryonic cell surface antigens and the presence of tumor specific molecules. Felsted et al (Canc Res (1983) 43:2754) have described cell element changes during the differentiation of promyelocytic leukemia cells. Neoplastic transformation induced changes in cell phenotype are presented in a review by Poste (in Cancer Invasion and Metastasis: Biologic Mechanisms and Therapy edited by S. B. Day et al, Raven Press, New York, 1977). Similar review articles describe phenotypes of leukemic cells (Greaves et al in Proc of International Symposium on Human Lymphocyte Differentiation: Its Application to Cancer, edited by Seron and Rosenfeld, North Holland Publishing, Amsterdam, 1978), B Lymphocytes (Thorsky et al, IBID), and Acute Lymphocytic Leukemia Cells (Greaves et al, Science 234, 1986). The identification of tumor specific antigens or markers and their association with tumors of specific tissue types permits clearer diagnosis and subsequent monitoring during therapy. A number of tumor surface proteins have been identified. Several examples include: a mutated rat gene p21 tumor lymphocyte protein (Bos et al, Nature (London) (1985) 315:726, and Clark et al, PNAS (USA) (1985) 82:5280); an Acute Lymphocyte Leukemia (ALL) Associated antigen GP 100 Phi (Greaves et al, Blood (1983) 61:628); Human T cell Leukemia Associated Antigen (HTLA) (Seon et al, J of Immunol (1981) 127(6):2580); a Human Lung Tumor Associated Antigen (Braatz et al, J Nat Cancer Inst (1978) 61 (4):1035), an estrogen 24,000 MW Human breast cancer marker (Adams et al, Cancer Res (1983) 43:4297); a Human Leiomyosarcoma antigen (Deng et al, Lancet, Feb. 21, 1981, p. 403); and a Human Mammary carcinoma antigen (Schlom et al, PNAS (1980) 77 (11):6841). Further concerning tumor markers, the concept of "altered self antigens" proposed by Edelman, Science (1976) 197:218 describes the presence of modified cell surface antigens normally indigenous to a cell type which are altered due to neoplastic transformation. These aberrant cells are viewed by the immune surveillance system as abnormal and they are capable of eliciting an immune response (Burnet, Brit Med J (1957) 1:179, and Nature (1970) 226:123). The reappearance of embryonic antigens has also been observed following the neoplastic transformation of cells. Carcinoembryonic antigen (CEA), Fetal Embryonic antigen (FEA) and Tumor Specific Transplantation Antigens (TSTA) have been useful in the serodiagnostic detection of carcinomas and sarcomas (Mitchison, "Immune Surveillance" in B and T Cells in Immune Recognition edited by F. Loors and G. E. Roelants, Wiley and Sons, New York, 1977).

Other analytes include lipoproteins, enzymes, immunoglobulins, lymphokines, cytokines, and drugs, including any drug to which antibodies can be prepared through the process of haptenization. In haptenization, a molecule that is too small to elicit antibody formation when injected by itself into an antibody-forming animal can be coupled to a larger carrier molecule, such as a protein molecule such as keyhole limpet hemocyanin, and injected in that form to form antibodies.

Other protein analytes include transcortin, erythropoietin, transferrin, various globulins, thyroxin-binding globulin, the immunoglobulins of various subclasses A, G, D, E, and M, various complement factors, blood clotting factors such as fibrinogen, Factor VII, tissue thromboplastin, and thrombin.

Still other analytes include drugs, both therapeutic drugs and drugs of abuse or having a potential for abuse. Many drugs that can serve as analytes are disclosed in U.S. Pat. No. 3,996,345 to Ullman et al., incorporated herein by this reference. These drugs include, but are not limited to, alkaloids and metabolites of alkaloids, including morphine, cocaine, mescaline, and lysergic acid, as well as synthetic opiates. Still other drugs include methadone, meperidine, amphetamine, methamphetamine, glutethimide, diphenylhydantoin, and drugs which come within the category of benzdiazocycloheptanes, phenothiazines and barbiturates. Still other drugs include epinephrine, ephedrine, L-dopa, and norepinephrine. Still other drugs include the tranquilizer Meprobamate, Tergitol and succinimides, such as Ethoxsumide. Still other drugs include tetrahydrocannabinol, cannabinol, and derivatives thereof, primarily compounds derived from marijuana, synthetic modifications and metabolites thereof. Still other drugs include steroids such as estrogens, gestogens, androgens, adrenocortical hormones, bile acids, cardiotonic glycoids, aglycones, saponins, and sapogenins. Typically, small molecules such as steroids, alkaloids, and peptides require haptenization as discussed above for the production of antibodies.

Although the foregoing discussion has focused on substances that can be determined by antigen-antibody interactions as analytes, the use of the term "analyte" is not to be taken to limit the scope of substances that can be assayed with devices and methods according to the present invention to substances that can be determined by antigen-antibody interactions. For example, for analytes for which a specific binding protein of sufficiently great specificity exists, either the antibody that is immobilized to the chromatographic strip or the antibody that is labeled with the conjugate can be replaced with a suitable specific binding protein. These include, but are not limited to, intrinsic factor protein as a member of a specific binding pair for the determination of Vitamin $B_{12}$, the use of folate-binding protein to determine folic acid, the use of a lectin as a member of a specific binding pair for the determination of a carbohydrate, or the use of a cytokine, lymphokine, or growth factor receptor such as interleukin-1 receptor to determine the corresponding cytokine, lymphokine, or growth factor.

Additionally, the term "analyte" can encompass nucleic acids such as DNA or RNA as long as suitable specific binding macromolecules exist for these nucleic acids. These suitable specific binding macromolecules can be proteins that bind to nucleic acids in a sequence-specific manner, or can be nucleic acid molecules or nucleic acid molecule analogues that bind to the sequence to be detected according to the Watson-Crick base pairing rules. If the nucleic acid to be detected is of sufficient length, the nucleic acid to be detected can hybridize at one sequence within the nucleic acid molecule to an immobilized complementary nucleic acid, and can then hybridize at another sequence within the nucleic acid molecule with a labeled nucleic acid, a process generally referred to as "sandwich hybridization," and described in greater detail in, for example, U.S. Pat. No. 6,825,331 to Manoharan et al., incorporated herein by this reference.

B. Detecting Reagents

Suitable detecting reagents have been described above. In general, the detectable agent includes, for example, antibodies or antigens specific for the analyte that are conjugated to a detectable material such as a colored material, a fluorescent material, or a chemiluminescent material. An example of a colored material is colloidal gold. Other colloidal metal labels or colloidal non-metal labels can also be used. The label can be a particle, a colored material, a fluorescent label, a chemiluminescent label, a redox label such as ferrocyanide, a radioactive label, a radiofrequency label, an enzymatic label, or a bioluminescent label, and may include more than one material. If more than one material is used, any combination of the possible materials can be used. For example, if the assay is intended to detect more than one analyte, detectable materials to be used may be fluorescent materials that fluoresce at different wavelengths. The particles can be colloidal gold particles, colloidal sulfur particles, colloidal selenium particles, colloidal barium sulfate particles, colloidal iron sulfate particles, colloidal metal sulfide particles, colloidal lead selenide particles, colloidal cadmium selenide particles, colloidal metal iodate particles, colloidal metal phosphate particles, colloidal metal ferrite particles, colloidal silver halide particles, colloidal silica particles, colloidal metal (hydrous) oxide particles and the like as described in U.S. Pat. No. 6,136,610, with or without an organic or inorganic coating, protein or peptide molecules, liposomes, or organic polymer latex particles such as polystyrene latex beads. The size of the particles may be related to the porosity of the chromatographic strip; in one alternative, the particles are sufficiently small to be transported along the element by capillary action of fluid. Still other labels known in the art can be used. For example, labels suitable for use in devices and methods according to the present invention can include, but are not limited to, luminescent labels; colorimetric labels, such as dyes; fluorescent labels; chemical labels, such as electroactive agents (e.g., ferrocyanide); enzymes; radioactive labels; or radiofrequency labels. In one embodiment that uses labels other than colloidal metallic or non-metallic particles, the labels are fluorescent labels such as quantum dot conjugates. Quantum dot conjugates are described, for example, in U.S. Pat. No. 6,855,551 to Bawendi et al., incorporated herein by this reference. The number of particles present in the test strip may vary, depending on the size and composition of the particles, the composition of the test strip and element strip, and the level of sensitivity of the assay.

Colloidal gold may be made by any conventional means, such as the methods outlined in G. Frens, 1973 Nature Physical Science, 241:20 (1973). Alternative methods may be described in U.S. Pat. Nos. 5,578,577; 5,141,850; 4,775,636; 4,853,335; 4,859,612; 5,079,172; 5,202,267; 5,514,602; 5,616,467; and 5,681,775, all of which are incorporated herein by this reference.

The selection of particle size may influence such factors as stability of bulk sol reagent and its conjugates, efficiency and completeness of release of particles from the test strip, speed and completeness of the reaction. Also, particle surface area may influence steric hindrance between bound moieties.

Also coupled to the detection agent may be an analyte non-specific agent. This agent is selected for its ability to bind to substances other than the analyte of interest. For example, if the analyte of interest is an antibody to *H. pylori*, then the analyte non-specific agent may be an antibody to an antigen not found, or rarely found, in the antibody to *H. pylori*. This binding may be specific for a substance other than the analyte of interest or non-specific for such a substance.

The analyte non-specific agent can be antibodies, more preferably rabbit IgG. The antibodies can be monoclonal antibodies or polyclonal antibodies. The term "antibody", as used herein, also refers to antibody fragments that are sufficient to bind to the analyte of interest. Alternatively, molecules such as engineered proteins having non-specific binding sites non-specific for the analyte of interest, can also be used. In another embodiment, a receptor that non-specifically binds to ligands other than the analyte of interest can be used, and vice versa. Finally, the analyte non-specific agent may be an antigen, another organic molecule, or a hapten conjugated to a protein non-specific for the analyte of interest. Descriptions of other suitable analyte non-specific agents may be found in U.S. Pat. No. 5,096,837, and include IgG, BSA, other albumins, casein, globulin, and immunoglobulin.

The analyte non-specific agent can comprise a control binding agent. Control binding agents are selected so as to bind specifically to molecules other than molecules that specifically bind to the analyte of interest. In this way, these control binding agents can bind in control binding zones, as discussed below. Substances useful as control binding agents include those substances described above as useful as first analyte binding agents. In a preferable embodiment, the control binding agent comprises rabbit anti-dinitrophenol (anti-DNP) antibody. Additional beneficial characteristics of control binding agents include, but are not limited to stability in bulk, non-specificity for analyte of interest, reproducibility and predictability of performance in test, molecular size, and avidity of binding to the control agent.

C. Buffers

When the sample is applied to Port-1 in the performance of a bidirectional assay and a buffer is applied to Port-2 for flow in the second direction, a suitable buffer is one that is compatible in pH and ionic strength with the sample and any reagents added to the sample. The buffer should not interact with any analytes or other macromolecules in the sample. Suitable buffers include, but are not limited to, phosphate buffered saline, Ringer's solution, Hank's solution, and buffered solutions buffered with (tris)hydroxymethylaminomethane (Tris™). A suitable buffer is 1×PBS containing 0.1% Tween 20, 0.01% casein, 0.3% SDS, 0.2 mM EDTA and 0.1% sodium azide; other alternative buffers can be used. The same types of buffers can be used when the buffer is applied to Port-1 to prewet the chromatographic strip and a sample is applied to Port-2.

for the presence of particular analytes, it is particularly suited for assays in which red blood cells are present in the testing fluid and where only a small sample volume, such as a finger prick, is available for testing.

EXAMPLES

The examples, which are intended to be purely exemplary of the invention and should, therefore, not be considered to limit the invention in any way, also describe and detail aspects and embodiments of the invention discussed above. The examples are not intended to represent that the experiments below are all or the only experiments performed. Efforts have been made to ensure accuracy with respect to numbers used (e.g., amounts, sizes, etc.) but some experimental errors and deviations should be accounted for.

TABLE 1

Summary of Element Selection in Port-2

| Top Layer | Chemical Nature | Hydrophobic/ Hydrophilic | Pore Size (μm) | Flow Rate (ml/min) | Capillary rise (mm/min) | Lower Layer | Ability to filter red blood cells (Yes/No) |
|---|---|---|---|---|---|---|---|
| #111 | Cellulose | Hydrophilic | 1 | 130 | 51 | Conjugate Pad | No |
| #141 | Glass fiber | Hydrophobic | 3 | 350 | 79 | Conjugate Pad | No |
| #142 | Glass fiber | Hydrophobic | 6 | 300 | 55 | Conjugate Pad | Yes |
| #1660 | CytoSep | Hydrophilic | 3 | 100 | 52 | Conjugate Pad | No |
| #1661 | CytoSep | Hydrophilic | 5 | 260 | 41 | Conjugate Pad | No |
| #1662 | CytoSep | Hydrophilic | 3 | 35 | 46 | Conjugate Pad | No |
| #1663 | CytoSep | Hydrophilic | 2 | 35 | 46 | Conjugate Pad | No |
| #319 | CytoSep | Hydrophilic | 19 | 375 | 54 | Conjugate Pad | No |
| Conjugate Pad | Glass fiber | Hydrophobic | 42 | 250 | 46 | Conjugate Pad | No |

INDUSTRIAL APPLICABILITY

The present invention may be advantageously employed in diagnostic settings including point of care settings, such as in a doctor's office or clinic or in a battlefield, for determining presence and quantity of analytes present in samples that may or may not contain cells, such as red blood cells, white blood cells and other cell types. The materials and methods of the present invention are useful, for example, in the detection of disease agents or antibodies thereto, including HIV, HAV, HBV, HCV, HSV, HPV, CMV, SARS virus, vaccinia virus, as well as other molecules, including, for example, deoxypyrodinoline (a bone resorption marker), human serum albumin, drugs of abuse, protein markers such as prostate specific antigen ("PSA"), kidney disease proteins such as lactate dehydrogenase, N-acetyl-β-D-glucosamine, pregnancy or fertility associated hormones such as chorionic gonadotropin ("hCG") and markers of urinary tract infection. The determination of blood borne analytes, such as therapeutic drugs, hormones, cancer markers such as PSA, cardiac markers (Troponin 1, Troponin T, CKMB and α-fetoprotein) is particularly suited to the present invention. In addition, the sample may be whole blood. Thus, although the devices and methods of the present invention are suitable for assaying various body fluids, including urine, saliva, sweat or mucus While the present invention has been described with reference to the specific embodiments thereof, it should be understood by those skilled in the art that various changes may be made and equivalents may be substituted without departing from the true spirit and scope of the invention. In addition, many modifications can be made to adapt a particular situation, material, composition of matter, process, process step or steps, to the objective, spirit or scope of the present invention. All such modifications are intended to be within the scope of the claims of the present invention.

To discover the best materials and conditions for conducting lateral flow assays for determination or quantitation of analytes in samples containing cells, such as whole blood samples containing red blood cells ("RBCs"), including determining the element or combination of elements for filtering cells and fluid, such as plasma, in a sample, the following experiments were conducted using the instrument ("ReLIA") and cassettes as described in U.S. Pat. No. 6,136,610 and U.S. Pat. No. 6,528,323, and as modified herein.

Example 1

Filtering Capability of Elements in Absence of Agglutinins

The test strip as shown in FIG. 2 was constructed with different elements as the sample filter. The filtering elements tested were all obtained from Ahlstrom Filtration, Inc. (USA) and include: cellulose absorbent grade 111, glass fibers grade #141 and grade #142, Cytosep grades 1660, 1661, 1662 and 1663. A sample containing whole blood was applied in Port-1 as shown in FIG. 1. The migration speed of plasma on the nitrocellulose chromatographic strip was observed. Results were obtained as set forth in Table 2.

A rabbit anti-human red blood cell antibody solution was prepared by adding 9.0825 g of Trizma Base (final concentration of 6.055 g/L), 1.7625 ml of HCl (final concentration of 1.7625 ml/L) and 1.8 g of EDTA.$Na_2$ (final concentration of 1.2 g/L) to 1.35 liters of deionized water. The mixture was stirred slowly until the chemical reagents were dissolved completely, about an hour. The solution was kept at room

TABLE 2

Blood Filtering Element Without Anti-hRBC

| Element | Sample | Volume μl | RBC Leaking | Migrate mm/min | Background | Time of RBC appearance on NC |
|---|---|---|---|---|---|---|
| Grade 111 Cellulose | Whole Blood | 100 | Yes | ≦16 | Red | 8 min |
|  |  | 100 | Yes | ≦16 | Red | 8 min |
|  |  | 100 | Yes | ≦16 | Red | 8 min |
|  |  | 100 | Yes | ≦16 | Red | 8 min |
|  |  | 100 | Yes | ≦16 | Red | 8 min |
| Grade 141 Glass Fiber | Whole Blood | 100 | Yes | ≦16 | Red | 3 min |
|  |  | 100 | Yes | ≦16 | Red | 3 min |
|  |  | 100 | Yes | ≦16 | Red | 3 min |
|  |  | 100 | Yes | ≦16 | Red | 3 min |
|  |  | 100 | Yes | ≦16 | Red | 3 min |
| Grade 142 Glass Fiber | Whole Blood | 100 | Yes | ≦16 | Red | 2 min |
|  |  | 100 | Yes | ≦16 | Red | 2 min |
|  |  | 100 | Yes | ≦16 | Red | 2 min |
|  |  | 100 | Yes | ≦16 | Red | 2 min |
|  |  | 100 | Yes | ≦16 | Red | 2 min |
| Grade 1660 Cytosep | Whole Blood | 100 | Yes | ≦16 | Red | 2 min |
|  |  | 100 | Yes | ≦16 | Red | 2 min |
|  |  | 100 | Yes | ≦16 | Red | 2 min |
|  |  | 100 | Yes | ≦16 | Red | 2 min |
|  |  | 100 | Yes | ≦16 | Red | 2 min |
| Grade 1661 Cytosep | Whole Blood | 100 | Yes | ≦16 | Red | 3 min |
|  |  | 100 | Yes | ≦16 | Red | 3 min |
|  |  | 100 | Yes | ≦16 | Red | 3 min |
|  |  | 100 | Yes | ≦16 | Red | 3 min |
|  |  | 100 | Yes | ≦16 | Red | 3 min |
| Grade 1662 Cytosep | Whole Blood | 100 | Yes | ≦16 | Red | 4 min |
|  |  | 100 | Yes | ≦16 | Red | 4 min |
|  |  | 100 | Yes | ≦16 | Red | 4 min |
|  |  | 100 | Yes | ≦16 | Red | 4 min |
|  |  | 100 | Yes | ≦16 | Red | 4 min |
| Grade 1663 Cytosep | Whole Blood | 100 | Yes | <16 | Red | 10 min (sticky) |
|  |  | 100 | Yes | <16 | Red | 10 min (sticky) |
|  |  | 100 | Yes | <16 | Red | 10 min (sticky) |
|  |  | 100 | Yes | <16 | Red | 10 min (sticky) |
|  |  | 100 | Yes | <16 | Red | 10 min (sticky) |

Example 2

Blood Filtering Capability of Elements Pre-Treated with Anti-RBC

A ten percent (10%) TWEEN 20 solution was prepared by adding 1 g of TWEEN 20 to 9 ml of deionized water, mixing the solution, and storing the solution for about a week at room temperature.

temperature for 4 hours or overnight at 4° C. The pH of the solution was adjusted to pH 8.5±0.1 by adding HCl. Rabbit anti-human red blood cell antibody (anti-hRBC) was added to the solution to a final concentration of about 0.25 mg/ml. About 0.3 ml of 10% Tween-20 solution was added to the anti-hRBC to a final concentration of 0.002%. The final solution was stored at 4° C. for 24 hr. Different elements to be tested for use as sample filters were treated with the rabbit anti-hRBC and tested for their ability to filter fresh human whole blood samples applied to Port-1 in the configuration as exemplified in FIG. 2. Results are recorded in Tables 3A and 3B.

TABLE 3A

Blood Filtering Element Pretreated With Anti-hRBC

| Element | Anti-RBC mg/ml | Specimen | Volume μl | RBC leaking | Migrate mm/min | Background | Time of RBC shown on NC |
|---|---|---|---|---|---|---|---|
| Grade 111 | 0.25 | Whole Blood | 100 | No | ≦16 | Clean | After 1 h |
|  |  |  | 100 | No | ≦16 | Clean | After 1 h |
|  |  |  | 100 | No | ≦16 | Clean | After 1 h |
|  |  |  | 100 | No | ≦16 | Clean | After 1 h |
|  |  |  | 100 | No | ≦16 | Clean | After 1 h |
| Grade 141 | 0.25 | Whole Blood | 100 | No | ≦16 | Clean | After 1 h |
|  |  |  | 100 | No | ≦16 | Clean | After 1 h |
|  |  |  | 100 | No | ≦16 | Clean | After 1 h |
|  |  |  | 100 | No | ≦16 | Clean | After 1 h |
|  |  |  | 100 | No | ≦16 | Clean | After 1 h |
| Grade 142 | 0.25 | Whole Blood | 100 | No | ≦16 | Clean | After 1 h |
|  |  |  | 100 | No | ≦16 | Clean | After 1 h |
|  |  |  | 100 | No | ≦16 | Clean | After 1 h |
|  |  |  | 100 | No | ≦16 | Clean | After 1 h |
|  |  |  | 100 | No | ≦16 | Clean | After 1 h |
| Grade 1660 | 0.25 | Whole Blood | 100 | No | ≦16 | Clean | After 1 h |
|  |  |  | 100 | No | ≦16 | Clean | After 1 h |
|  |  |  | 100 | No | ≦16 | Clean | After 1 h |
|  |  |  | 100 | No | ≦16 | Clean | After 1 h |
|  |  |  | 100 | No | ≦16 | Clean | After 1 h |
| Grade 1661 | 0.25 | Whole Blood | 100 | No | ≦16 | Clean | After 1 h |
|  |  |  | 100 | No | ≦16 | Clean | After 1 h |
|  |  |  | 100 | No | ≦16 | Clean | After 1 h |
|  |  |  | 100 | No | ≦16 | Clean | After 1 h |
|  |  |  | 100 | No | ≦16 | Clean | After 1 h |
| Grade 1662 | 0.25 | Whole Blood | 100 | No | ≦16 | Clean | After 1 h |
|  |  |  | 100 | No | ≦16 | Clean | After 1 h |
|  |  |  | 100 | No | ≦16 | Clean | After 1 h |
|  |  |  | 100 | No | ≦16 | Clean | After 1 h |
|  |  |  | 100 | No | ≦16 | Clean | After 1 h |
| Grade 1663 | 0.25 | Whole Blood | 100 | — | — | no filtering | — |
|  |  |  | 100 | — | — | no filtering | — |
|  |  |  | 100 | — | — | no filtering | — |
|  |  |  | 100 | — | — | no filtering | — |
|  |  |  | 100 | — | — | no filtering | — |

TABLE 3B

| Element | Anti-RBC | Sample | RBC Leaking | Testing Time min | HC Dr | LC Dr | TEST Dr | RI = TEST Dr/LC Dr | S/CO | Time for RBC Leaking |
|---|---|---|---|---|---|---|---|---|---|---|
| #142 | No | HIV (+) | Yes | 30 | — | — | — |  | — | 2 min |
|  | No | Blood | Yes | 30 | — | — | — |  | — | 2 min |
|  | No | 50 μl | Yes | 30 | — | — | — |  | — | 2 min |
|  | No |  | Yes | 30 | — | — | — |  | — | 2 min |
|  | No |  | Yes | 30 | — | — | — |  | — | 2 min |
| Buffer Pad | Yes |  | Some | 30 | — | — | — |  | — | 3 min |
|  | Yes |  | Some | 30 | — | — | — |  | — | 3 min |
|  | Yes |  | Some | 30 | — | — | — |  | — | 3 min |
|  | Yes |  | Some | 30 | — | — | — |  | — | 3 min |
|  | Yes |  | Some | 30 | — | — | — |  | — | 3 min |
| #142 | Yes |  | No | 30 | 0.2713 | 0.2116 | 0.182 | 0.8601 | 8.603 | After 1 h |
|  | Yes |  | No | 30 | 0.1422 | 0.1715 | 0.1761 | 1.0268 | 10.2693 | After 1 h |
|  | Yes |  | No | 30 | 0.1981 | 0.1921 | 0.2282 | 1.1879 | 11.8776 | After 1 h |
|  | Yes |  | No | 30 | 0.2037 | 0.1843 | 0.1899 | 1.0304 | 10.3033 | After 1 h |
|  | Yes |  | No | 30 | 0.2287 | 0.1899 | 0.1846 | 0.9721 | 9.723 | After 1 h |

The results show that different elements could be used for filtering red blood cells when used in conjunction with an agglutinin, such as anti-RBC antibody, and that a sample size of 50 μl is sufficient for testing.

Example 3

Comparison Between Using Whole Blood Versus Using Plasma

The test strip as in Example 2 was prepared and whole blood or plasma was added to the sample filter in Port-1 and the results were compared, as shown in Table 4.

TABLE 4

Comparison of Testing Results Between Whole Blood and Plasma

| Element | Anti-hRBC Mg/ml | Sample | Volume | RBC Leaking | Time min | HC Dr | LC Dr | TEST Dr | RI = TEST Dr/LC Dr | S/CO | Result |
|---|---|---|---|---|---|---|---|---|---|---|---|
| #142 | 0.25 | HIV (−) | 50 μl | No | 30 min | 0.1777 | 0.0862 | 0 | 0 | 0 | (−) |
| | 0.25 | Blood | 50 μl | No | 30 min | 0.2268 | 0.0967 | 0 | 0 | 0 | (−) |
| | 0.25 | | 50 μl | No | 30 min | 0.073 | 0.1083 | 0 | 0 | 0 | (−) |
| | 0.25 | | 50 μl | No | 30 min | 0.183 | 0.0728 | 0 | 0 | 0 | (−) |
| | 0.25 | | 50 μl | No | 30 min | 0.3277 | 0.109 | 0 | 0 | 0 | (−) |
| #142 | 0.25 | HIV (−) | 50 μl | No | 15 min | 0.4033 | 0.1926 | 0 | 0 | 0 | (−) |
| | 0.25 | Plasma | 50 μl | No | 15 min | 0.3587 | 0.1945 | 0 | 0 | 0 | (−) |
| | 0.25 | | 50 μl | No | 15 min | 0.36 | 0.1919 | 0 | 0 | 0 | (−) |
| | 0.25 | | 50 μl | No | 15 min | 0.3822 | 0.1955 | 0 | 0 | 0 | (−) |
| | 0.25 | | 50 μl | No | 15 min | 0.3759 | 0.1964 | 0 | 0 | 0 | (−) |
| #142 | 0.25 | HIV (+) | 50 μl | No | 30 min | 0.1213 | 0.1781 | 0.2014 | 1.1308 | 11.311 | (+) |
| | 0.25 | Blood | 50 μl | No | 30 min | 0.1419 | 0.1441 | 0.2181 | 1.5135 | 15.1325 | (+) |
| | 0.25 | | 50 μl | No | 30 min | 0.1781 | 0.1408 | 0.2153 | 1.5291 | 15.2911 | (+) |
| | 0.25 | | 50 μl | No | 30 min | 0.074 | 0.075 | 0.1032 | 1.3760 | 13.7626 | (+) |
| | 0.25 | | 50 μl | No | 30 min | 0.1653 | 0.1605 | 0.2142 | 1.3346 | 13.3458 | (+) |
| #142 | 0.25 | HIV (+) | 50 μl | No | 15 min | 0.2755 | 0.1423 | 0.2011 | 1.4132 | 14.13 | (+) |
| | 0.25 | Plasma | 50 μl | No | 15 min | 0.3628 | 0.18 | 0.2344 | 1.3022 | 13.0244 | (+) |
| | 0.25 | | 50 μl | No | 15 min | 0.3084 | 0.1451 | 0.2005 | 1.3818 | 13.8166 | (+) |
| | 0.25 | | 50 μl | No | 15 min | 0.3149 | 0.1468 | 0.1862 | 1.2684 | 12.6852 | (+) |
| | 0.25 | | 50 μl | No | 15 min | 0.3425 | 0.1647 | 0.2164 | 1.3139 | 13.139 | (+) |

The results show that either plasma or whole blood could be used with the test strip of the present invention, both giving substantially consistent quantifiable results.

Example 4

Comparison of Different Elements as Sample Filters for Sample Application at Port-2

In this Example, the test strip as shown in FIG. 2 was constructed, but the buffer pad of FIG. 2 was substituted with one or two sample filters chosen from among the following elements: Cytosep Grade 1661 ("1661"), Cytosep Grade 1660 ("1660"), glass fiber grade #142 ("#142"), glass fiber grade #141 ("#141"), and cellulose grade 111 ("111") from Ahlstrom Filtration, Inc. These sample filters were tested for their ability to filter red blood cells. A conjugate pad (Millipore Corp.) and nitrocellulose element (Millipore Corp.) were used as shown in FIG. 2. A specified amount of blood sample was applied to Port-2. Results shown in Table 5 demonstrated that Cytosep 1661, glass fibers #141 and #142 were able to filter the sample and allow plasma to migrate to the nitrocellulose element, with glass fibers #141 and #142 yielding the shortest filtering time.

TABLE 5

Comparison of Different Elements Used Singly as a Sample Filter

| Element Model | Sample Volume (μl) | Time for Plasma to filter out (sec) | Time for RBC to leak out (sec) | Plasma Migration Speed (mm/min) | RBC remained on filter after 30 min |
|---|---|---|---|---|---|
| 1661 | 200 | 240 | 290 | 1.8 | Yes |
| 1660 | 200 | — | — | — | |
| 141 | 200 | 90 | 280 | 16.8 | Yes |

TABLE 5-continued

Comparison of Different Elements Used Singly as a Sample Filter

| Element Model | Sample Volume (μl) | Time for Plasma to filter out (sec) | Time for RBC to leak out (sec) | Plasma Migration Speed (mm/min) | RBC remained on filter after 30 min |
|---|---|---|---|---|---|
| 142 | 200 | 98 | 395 | 16.1 | |
| 111 | 200 | — | — | — | Yes |

"—" means no plasma filtered and migrated to the Nitrocellulose element.

TABLE 6

Comparison of Different Elements Used in a Bilayer for Filtering Sample

| Element Model | Sample Volume (μl) | Time for Plasma to filter out (sec) | Time for RBC to leak out (sec) | Plasma Migration Speed (mm/min) |
|---|---|---|---|---|
| 142 + 142 | 200 | 457 | 582 | 5.87 |
| 141 + 141 | 200 | 135 | 1015 | 1.95 |

TABLE 6-continued

Comparison of Different Elements Used in a Bilayer for Filtering Sample

| Element Model | Sample Volume (μl) | Time for Plasma to filter out (sec) | Time for RBC to leak out (sec) | Plasma Migration Speed (mm/min) |
|---|---|---|---|---|
| 141 + 142 | 200 | 113 | 238 | 2.93 |
| 142 + 141 | 200 | 640 | 686 | 2.26 |
| 141 + 1661 | 200 | 111 | 236 | 5.74 |
| 142 + 1660 | 200 | 247 | 409 | 3.41 |
| 142 + 1661 | 200 | 112 | 253 | 2.83 |
| 141 + 1660 | 200 | 440 | 582 | 5.71 |

Results shown in Table 6 demonstrated that all combinations of elements tested allowed plasma to filter out of the combination sample filter at varying speeds.

Example 5

Test of Glass Fibers Grade #141 and Grade #142 as Sample Filters for Sample Application at Port-2

In this Example, the test strip of FIG. 2 was constructed except that the buffer pad shown in FIG. 2 was substituted with a sample filter for application of sample. The sample filter used in this experiment was a single glass fiber element, grade #141 or grade #142, that was previously treated with 0.5 mg/ml rabbit anti-human red blood cells (An-kang Biotech, China) ("anti-hRBC") or mouse anti-hRBC (indicated by an asterisk, *). Also, a conjugate pad ("CP") was tested in conjunction with the glass fiber elements. The CP was either previously treated or not treated with 0.5 mg/ml rabbit anti-human red blood cells ("anti-hRBC") or mouse anti-hRBC. A nitrocellulose ("NC") element was used as previously described. A specified amount of whole blood (200 μl) was applied to the sample filter at Port-2. Results are shown in Table 7.

The results demonstrated that all the elements tested, whether a single CP or combinations of #141 or #142 with CP, whether pre-treated with anti-RBC or not, were capable of causing plasma to filter out onto the NC element. The time course for the plasma to migrate to the NC ranged from about 124 seconds for the #141*+CP* combination, to 126 seconds for the #142*+CP* combination, to 130 seconds for the #141*+CP combination, to 140 seconds for the #142*+CP combination. Plasma filtered out of the CP element alone in about 138 seconds. The best combination of filtration and migration rate was with the combination of #142*+CP*.

For CP alone, RBCs leaked out of the CP relatively quickly, in about 159 seconds, and were very apparent on the NC element 30 min. after start of experiment. In contrast, no RBC leakage was apparent macroscopically during the course of the experiment for the #142*+CP* combination, and no RBC were macroscopically apparent on the NC element at the 30 min. time point. In comparison, the #141*+CP* combination was slightly less effective, with RBC leaking out in about 1350 seconds (22.5 min.) and a few RBCs were macroscopically apparent on the NC element at the 30 min. time point.

Further in comparison, the #142*+CP combination was also less effective, when CP had not been pretreated with anti-RBC. With this combination, RBC started leaking out of these filters at about 1150 seconds (19.2 min.) and some RBC were seen on the NC element at the 30 min. time point after start of experiment. For the #141*+CP combination, RBCs were observed to leak out at 680 seconds (11.3 min.) and some RBCs were observed on the NC element. The plasma migration speed for all elements tested in this experiment was greater than 16 mm/min.

TABLE 7

Comparison of Combination of Elements in Filtering RBC

| Element Model | Sample Volume (μl) | Time for Plasma to filter out (sec) | Time for RBC to leak out (sec) | Plasma Migration Speed (mm/min) | RBC showed on NC after 30 min |
|---|---|---|---|---|---|
| 142* + CP | 200 | 140 | 1150 | >16 | Some |
| 142* + CP* | 200 | 126 | — | >16 | No |
| 141* + CP | 200 | 130 | 680 | >16 | Some |
| 141* + CP* | 200 | 124 | 1350 | >16 | few |
| CP only | 200 | 138 | 159 | >16 | Completely leaking |

*means pretreated with 0.5 mg/ml rabbit anti-hRBC (mouse anti-hRBC)

"—" means no RBC leaking out to testing window within 30 min after blood sample applied.

The results in Examples 1-5 show that the pore size of a single element alone was not predictive of whether a element would function well as a sample filter for the analyses herein when sample was applied at Port-2. Of the elements tested, cellulose 111 has the smallest pore size of 1 μm (see Table 1) and was able to keep RBCs from leaking out (Table 5). However, as shown in Table 5, plasma was unable to filter out of the element as well. The CytoSep 1660 element and the glass fiber element #141 both have a pore size of 3 μm (see Table 1), yet plasma filtered out of glass fiber element #141 but not CytoSep 1660 element. The difference here is that the glass fiber element is hydrophobic and the CytoSep 1660 was less hydrophobic and more hydrophilic.

Similarly, consistent with the premise that pore size alone is not indicative of how well a element functions as a sample filter, the pore size of glass fiber element #141 was 3 μm, smaller than the pore size of glass fiber element #142, which was 6 μm, yet plasma filtered out of the smaller-pore-size element #141 more quickly, i.e., in 90 seconds compared to 98 seconds for the larger-pore-size element #142 (Table 5). RBCs leaked out of the #141 element faster than for the #142 element, i.e., 280 seconds versus 395 seconds. Plasma migration rate was faster for the #141 element (16.8 mm/min.) than the #142 element (16.1 mm/min.).

The use of two sample filters without anti-RBC instead of one generally slowed down the plasma migration speed for the glass fiber elements from about 16 mm/min (Table 5) to a range of about 1.95 to about 5.87 mm/min (Table 6). RBCs still leaked out of these bi-layered filters (Table 6). For the combination of #141+#141, it took 1015 seconds (16.9 min.) for the RBCs to leak out onto the NC elements and 135 seconds (2.3 min.) for the plasma to filter out (Table 6). For the #142+#141 combination, where the #142 element is on top of the #141 element, RBCs leaked out in 686 seconds (11.4 min.) but it took plasma a much longer time to filter out 640 seconds (10.7 min.) (Table 6). For the combination of #141+#142, where the #141 element is on top of the #142 element, plasma filtered out more quickly in 113 seconds (1.9 min.), but RBC leaked out more quickly as well in 238 seconds (about 4 min.) (Table 6).

When anti-RBC antibodies were used with any of the sample filter elements tested (Table 3A and 3B), all elements tested exhibited good RBC filtering capability in that no apparent RBC leakage took place within a 30 min. window. Background noise on the NC element was low. Plasma migration speed was less than 16 mm/min. For CytoSep 1663, no plasma filtering was apparent. Quantitative analysis of blood containing anti-HIV was possible with glass fiber element #142 pretreated with anti-RBC (Table 3A and 3B). Table 3B also shows that a sample size of 50 μl is sufficient to obtain quantitative results from the assay.

The combination of #141*+CP (Table 7), where #141 was pre-treated with anti-RBC antibody, worked better in filtering out RBC than untreated #141 alone (Table 5). Similarly #142*+CP worked better in filtering out RBC than untreated #142 alone. Both anti-RBC treated #141 and #142 worked better in filtering RBC when used with anti-RBC treated CP. In this experiment, 142*+CP* was most efficient in filtering RBC and plasma.

Example 6

Test of Efficiency of Plasma and RBC Filtering in Presence of Anti-Coagulants in the Blood Sample Glass fiber element #142 was used as the sample filter in this experiment. Element #142 was pretreated with 0.25 mg/ml of rabbit anti-human RBC as previously described. This element was then pretreated with anti-coagulants (disodium EDTA: 1.5 mg/ml, trisodium citrate: 3.5 mg/ml or Heparin, sodium: 0.1 mg/ml) or not prior to use. The blood sample was also pretreated with anti-coagulants (disodium EDTA: 1.5 mg/ml, trisodium citrate: 3.5 mg/ml or Heparin, sodium: 0.1 mg/ml) or not prior to application onto the sample filter. Blood sample was applied onto sample filter in Port-2 as described above. Results are set forth in Tables 8 and 9.

TABLE 8

Efficiency of Plasma Filtration In Absence of Anticoagulant on #142

| | Whole Blood Volume | | | | | | | | |
|---|---|---|---|---|---|---|---|---|---|
| | 50 μl | | | 75 μl | | | 150 μl | | |
| #142 without Anticoagulant | RBC leaking | Plasma Migrate mm/min | RBC remained | RBC leaking | Plasma Migrate mm/min | RBC remained | RBC leaking | Plasma Migrate mm/min | RBC remained |
| Blood without anticoagulant | No | ≦16 | Few | No | >16 | Some | No | >16 | More |
| Blood with EDTANa$_2$ added | No | ≦16 | Few | No | >16 | Some | No | >16 | More |
| Blood with Citra-Na added | No | ≦16 | Few | No | >16 | Some | No | >16 | More |
| Blood with Heparin Sodium added | No | ≦16 | Few | No | >16 | Some | No | >16 | More |

TABLE 9

Efficiency Plasma Filtration In the Presence of Anticoagulants on #142

| #142 | Whole Blood Volume | | | | | | | | |
|---|---|---|---|---|---|---|---|---|---|
| Pretreated | 50 μl | | | 75 μl | | | 150 μl | | |
| with anticoagulant reagents | RBC leaking | Plasma Migrate mm/min | RBC remained | RBC leaking | Plasma Migrate mm/min | RBC remained | RBC leaking | Plasma Migrate mm/min | RBC remained |
| Blood without anticoagulant | No | ≦16 | Few | No | >16 | Some | No | >16 | More |
| Blood with EDTANa$_2$ added | No | ≦16 | Few | No | >16 | Some | No | >16 | More |
| Blood with Citra-Na added | No | ≦16 | Few | No | >16 | Some | No | >16 | More |
| Blood with Heparin Sodium added | No | ≦16 | Few | No | >16 | Some | No | >16 | More |

The results show that anti-coagulants did not affect the plasma filtering efficiency when applied either on the sample filter or in the blood sample in a bilateral flow assay.

Example 7

Effect of RBC Volume on a Quantitative Assay

To determine whether RBC volume affects the accuracy of quantitative testing in lateral stop-flow assays, the following experiments were conducted. Whole blood that was positive for hepatitis B surface antigen ("HBsAg") with a tested hematocrit of 44% was aliquoted to 1 ml/tube. The RBC volume in these aliquots was taken as 100%. The RBC volume was then increased or decreased up to 40% through removal or addition of plasma from the same blood sample after spinning the blood sample at 800×g for 15 min. Glass fiber element #142 was pretreated with 0.5 mg/ml of mouse anti-human RBC and used as the sample filter at Port-2 in a HBsAg test cassette. The lateral flow assay was conducted by application of sample to the sample filter in Port-2. The lateral flow assay was conducted as before. In this configuration, a fluid collector was placed under the sample filter in a test strip as shown in FIG. 3, where the fluid collector comprises a glass fiber element like the conjugate pad, but without the colloidal gold labeled antigen or antibody of the conjugate pad. Results are shown in Table 10.

TABLE 10

Effect of RBC Volume on a Quantitative HBsAg Assay

| | Sample Volume (μl) | Migration Speed (mm/min) | HBsAg Concentration (ng/ml) | Average 1 (ng/ml) | Average 2 (ng/ml) | Standard Deviation | CV |
|---|---|---|---|---|---|---|---|
| Normal = 100% | 200 | >16 | 18.7 | 18.475 | 17.36 | 0.72 | 4.1% |
| Normal = 100% | 200 | >16 | 19.4 | | | | |
| Normal = 100% | 200 | >16 | 18.6 | | | | |
| Normal = 100% | 200 | >16 | 17.2 | | | | |
| Testing CV | | | 4.99% | | | | |
| 10% Higher | 200 | >16 | 16.7 | 16.925 | | | |
| 10% Higher | 200 | >16 | 16.5 | | | | |
| 10% Higher | 200 | >16 | 19.3 | | | | |
| 10% Higher | 200 | >16 | 15.2 | | | | |
| Testing CV | | | 10.1% | | | | |
| 20% Higher | 200 | ≧16 | 18.2 | 16.9 | | | |
| 20% Higher | 200 | ≧16 | 16.7 | | | | |
| 20% Higher | 200 | ≧16 | 15.4 | | | | |
| 20% Higher | 200 | ≧16 | 17.3 | | | | |
| Testing CV | | | 7.0% | | | | |
| 30% Higher | 200 | <16 | 15.8 | 17.3 | | | |
| 30% Higher | 200 | <16 | 15.6 | | | | |
| 30% Higher | 200 | <16 | 20.8 | | | | |
| 30% Higher | 200 | <16 | 17.1 | | | | |
| Testing CV | | | 13.9% | | | | |
| 10% Lower | 200 | >16 | 16.8 | 16.15 | | | |
| 10% Lower | 200 | >16 | 16 | | | | |
| 10% Lower | 200 | >16 | 16.2 | | | | |
| 10% Lower | 200 | >16 | 15.6 | | | | |
| Testing CV | | | 3.1% | | | | |
| 20% Lower | 200 | >16 | 17.3 | 16.98 | | | |
| 20% Lower | 200 | >16 | 18.6 | | | | |
| 20% Lower | 200 | >16 | 16.1 | | | | |
| 20% Lower | 200 | >16 | 15.9 | | | | |
| Testing CV | | | 7.3% | | | | |
| 30% Lower | 200 | >16 | 16.7 | 17.9 | | | |
| 30% Lower | 200 | >16 | 19 | | | | |
| 30% Lower | 200 | >16 | 18.2 | | | | |
| 30% Lower | 200 | >16 | 17.7 | | | | |
| Testing CV | | | 5.4% | | | | |
| 40% Lower | 200 | >16 | 18.5 | 17.48 | | | |
| 40% Lower | 200 | >16 | 17.6 | | | | |
| 40% Lower | 200 | >16 | 16.4 | | | | |
| 40% Lower | 200 | >16 | 17.4 | | | | |
| Testing CV | | | 5.0% | | | | |
| Plasma | 200 | >16 | 19.3 | 18.1 | | | |
| Plasma | 200 | >16 | 17.6 | | | | |
| Plasma | 200 | >16 | 18.7 | | | | |
| Plasma | 200 | >16 | 16.8 | | | | |
| Testing CV | | | 6.2% | | | | |

The HBsAg concentration for a specified plasma volume was determined in 4 independent assays and averaged to produce Average 1. The average HBsAg concentration for each of the various plasma volumes tested were then averaged to produce Average 2. The observed coefficient of variation ("CV") was less than 5% demonstrating that there was little difference between the results at the different red cell volumes.

Similarly, whole blood sample from a thyroid stimulating hormone ("TSH") abnormal patient, having a TSH concentration of 28 μIU/ml as tested by radioimmunoassay, and a hematocrit of 44% was aliquoted to 1 ml/tube. This RBC volume was taken as 100%. The RBC volume was increased or decreased up to 40% through removing or adding plasma from the same blood sample after spinning the blood sample at 800×g for 15 min. Glass fiber element #142 was pretreated with 0.5 mg/ml of mouse anti-human RBC and was used as the sample filter at both Port-1 and Port-2 in a TSH test cassette. Blood sample was applied first to Port-1 and then to Port-2 in the volumes specified in Table 11. In this example, one sample was run in four different cassettes and a fluid collector was placed under the sample filter in a test strip as shown in FIG. 3, where the fluid collector comprises a glass fiber element like the conjugate pad, but without the colloidal gold labeled antigen or antibody of the conjugate pad.

TABLE 11

Effect of RBC Volume in Quantitative TSH Assay

| Sample | Vol. In Port-1 (μl) | Vol. in Port-2 (μl) | Test Time (min) | HC Dr | LC Dr | TEST Dr | RI = TEST Dr/LC Dr | Conc. (μIU/ml) | Average 1 (μIU/ml) | Average 2 (μIU/ml) | Standard Deviation | CV |
|---|---|---|---|---|---|---|---|---|---|---|---|---|
| Normal | 50 | 150 | 30 | 0.3679 | 0.4733 | 0.3456 | 0.7302 | 29.66 | 28.09 | 28.5758 | 2.1258 | 7.44% |
|  |  |  |  | 0.4209 | 0.4736 | 0.3368 | 0.7111 | 28.29 |  |  |  |  |
|  |  |  |  | 0.4367 | 0.5451 | 0.4117 | 0.7553 | 31.56 |  |  |  |  |
|  |  |  |  | 0.4582 | 0.5414 | 0.3797 | 0.7013 | 27.6 |  |  |  |  |
|  |  |  |  | 0.3017 | 0.4605 | 0.2929 | 0.6360 | 23.34 |  |  |  |  |
| 10% Higher | 50 | 150 | 30 | 0.316 | 0.5106 | 0.3958 | 0.7752 | 33.13 | 28.858 |  |  |  |
|  |  |  |  | 0.3918 | 0.6377 | 0.4369 | 0.6851 | 26.49 |  |  |  |  |
|  |  |  |  | 0.3019 | 0.4654 | 0.3739 | 0.8034 | 35.49 |  |  |  |  |
|  |  |  |  | 0.3851 | 0.6016 | 0.3954 | 0.6572 | 24.66 |  |  |  |  |
|  |  |  |  | 0.3654 | 0.5234 | 0.3428 | 0.6549 | 24.52 |  |  |  |  |
| 20% Higher | 50 | 150 | 30 | 0.2492 | 0.4968 | 0.3521 | 0.7087 | 28.12 | 33.096 |  |  |  |
|  |  |  |  | 0.1325 | 0.4081 | 0.3378 | 0.8277 | 37.64 |  |  |  |  |
|  |  |  |  | 0.4036 | 0.4981 | 0.3921 | 0.7872 | 34.12 |  |  |  |  |
|  |  |  |  | 0.2374 | 0.4832 | 0.3663 | 0.7581 | 31.77 |  |  |  |  |
|  |  |  |  | 0.3286 | 0.4739 | 0.3714 | 0.7837 | 33.83 |  |  |  |  |
| 30% Higher | 50 | 150 | 30 | 0.285 | 0.5246 | 0.3487 | 0.6647 | 25.14 | 25.976 |  |  |  |
|  |  |  |  | 0.3095 | 0.5654 | 0.3776 | 0.6678 | 25.35 |  |  |  |  |
|  |  |  |  | 0.387 | 0.5638 | 0.3756 | 0.6662 | 25.24 |  |  |  |  |
|  |  |  |  | 0.3331 | 0.5218 | 0.3613 | 0.6924 | 26.99 |  |  |  |  |
|  |  |  |  | 0.4314 | 0.4937 | 0.3431 | 0.6950 | 27.16 |  |  |  |  |
| 10% Lower | 50 | 150 | 30 | 0.4032 | 0.58 | 0.4178 | 0.7203 | 28.95 | 30.118 |  |  |  |
|  |  |  |  | 0.4378 | 0.4639 | 0.3431 | 0.7396 | 30.37 |  |  |  |  |
|  |  |  |  | 0.4119 | 0.534 | 0.406 | 0.7603 | 31.95 |  |  |  |  |
|  |  |  |  | 0.3408 | 0.5217 | 0.3823 | 0.7328 | 29.86 |  |  |  |  |
|  |  |  |  | 0.403 | 0.5726 | 0.4165 | 0.7274 | 29.46 |  |  |  |  |
| 20% Lower | 50 | 150 | 30 | 0.2859 | 0.4134 | 0.5012 | 1.2124 | 28.8 | 27.944 |  |  |  |
|  |  |  |  | 0.3542 | 0.3538 | 0.5372 | 1.5184 | 28.03 |  |  |  |  |
|  |  |  |  | 0.1217 | 0.4228 | 0.5584 | 1.3207 | 26.65 |  |  |  |  |
|  |  |  |  | 0.3955 | 0.3661 | 0.5727 | 1.5643 | 26.31 |  |  |  |  |
|  |  |  |  | 0.1942 | 0.3896 | 0.4754 | 1.2202 | 29.93 |  |  |  |  |
| 30% Lower | 50 | 150 | 30 | 0.4156 | 0.531 | 0.3725 | 0.7015 | 27.62 | 28.176 |  |  |  |
|  |  |  |  | 0.4138 | 0.5416 | 0.3874 | 0.7153 | 28.58 |  |  |  |  |
|  |  |  |  | 0.4028 | 0.5107 | 0.3742 | 0.7327 | 29.85 |  |  |  |  |
|  |  |  |  | 0.3895 | 0.5227 | 0.3686 | 0.7052 | 27.87 |  |  |  |  |
|  |  |  |  | 0.3955 | 0.5437 | 0.3763 | 0.6921 | 26.96 |  |  |  |  |
| 40% Lower | 50 | 150 | 30 | 0.3898 | 0.5024 | 0.3631 | 0.7227 | 29.12 | 28.732 |  |  |  |
|  |  |  |  | 0.4023 | 0.5343 | 0.412 | 0.7711 | 32.81 |  |  |  |  |
|  |  |  |  | 0.369 | 0.5512 | 0.3706 | 0.6724 | 25.64 |  |  |  |  |
|  |  |  |  | 0.3775 | 0.4997 | 0.3581 | 0.7166 | 28.68 |  |  |  |  |
|  |  |  |  | 0.4182 | 0.5448 | 0.3806 | 0.6986 | 27.41 |  |  |  |  |
| Plasma | 50 | 150 | 30 | 0.4 | 0.4439 | 0.3034 | 0.6835 | 26.39 | 26.192 |  |  |  |
|  |  |  |  | 0.361 | 0.4208 | 0.2795 | 0.6642 | 25.12 |  |  |  |  |
|  |  |  |  | 0.3539 | 0.4248 | 0.2846 | 0.6700 | 25.49 |  |  |  |  |
|  |  |  |  | 0.4089 | 0.4244 | 0.3018 | 0.7111 | 28.29 |  |  |  |  |
|  |  |  |  | 0.3799 | 0.448 | 0.3014 | 0.6728 | 25.67 |  |  |  |  |

The TSH concentration for a specified plasma volume was determined in 5 independent assays and averaged to produce Average 1. The average TSH concentration for each of the various plasma volumes tested was then averaged to produce Average 2. The observed coefficient of variation ("CV") was less than 8% demonstrating that there was little difference between the TSH results at the different red cell volumes.

The above results show that the present assay, in the sandwich format, using samples containing fluid and cells, is volume independent.

Example 8

Effect of Red Blood Cell Volume in Qualitative Assay

To determine whether presence of RBC affects the accuracy of qualitative testing in lateral bidirectional flow assay, the following experiment was conducted. HIV-positive whole blood with a tested RBC hematocrit of 45.3% was aliquoted to 1 ml/tube. This RBC volume was taken as 100%. The RBC volume was increased or decreased by removing or adding plasma from the same blood sample after spinning the blood sample at 800×g for 15 min. Glass fiber element #142 was pretreated with 0.25 mg/ml of rabbit anti-hRBC and used as a sample filter at Port-1 in a HIV test cassette. Results are recorded in Table 12.

by the average of a large quantity of negative samples. The cutoff represents the background in an HIV test when a whole blood sample is applied to a 142 element pretreated with anti-hRBC at Port-1 in a Bi-directional flow assay. The test band is measured as RI (Relative Intensity or ratio of the test band Dr to the HC or LC Dr), which acts to cancel variables between cassettes of the same lot. This provides higher reproducibility as the effect of variables on both control bands and the test band are balanced by RI.

Example 9

Effect of Gold Conjugate Coating Methods on Accuracy of Assay

To determine the effect of different coating methods for coating conjugates on the conjugate pad, the following experiment was conducted using conjugate pads coated with gold-labeled anti-human IgG or gold labeled anti-HBsAg using a rinse coating procedure or a Biojet coating method. Glass fiber element #142 pretreated with 0.25 mg/ml of rabbit anti-hRBC was used as the sample filter. Gold-labeled anti-human IgG or anti-HBsAg coated on a glass conjugate pad (Pall Specialty Materials) by Bio-jet or rinse methods. The experiment was conducted using HIV positive whole blood in a HIV test cassette and HBsAg positive whole blood in an

TABLE 12

Effect of Red Blood Cell Volume in an HIV Assay

| RBC Vol. | Test Time | HC Dr | LC Dr | TEST Dr | RI = TEST Dr/LC Dr | S/CO | AVE | AVE 2 | SD | CV |
|---|---|---|---|---|---|---|---|---|---|---|
| Normal = 100% | 30 min | 0.2341 | 0.1272 | 0.2059 | 1.6187 | 16.18 | 19.69 | 20.0019 | 1.8855 | 9.43% |
| Normal = 100% | 30 min | 0.2066 | 0.0941 | 0.2123 | 2.2561 | 22.57 | | | | |
| Normal = 100% | 30 min | 0.2824 | 0.0942 | 0.1914 | 2.0318 | 20.32 | | | | |
| 10% higher | 30 min | 0.3702 | 0.1324 | 0.2564 | 1.9366 | 19.36 | 19.61 | | | |
| 10% higher | 30 min | 0.225 | 0.1193 | 0.2241 | 1.8785 | 18.78 | | | | |
| 10% higher | 30 min | 0.0961 | 0.1044 | 0.216 | 2.0690 | 20.69 | | | | |
| 20% higher | 30 min | 0.0503 | 0.1144 | 0.1752 | 1.5315 | 15.32 | 17.9233 | | | |
| 20% higher | 30 min | 0.0753 | 0.136 | 0.2474 | 1.8191 | 18.19 | | | | |
| 20% higher | 30 min | 0.0747 | 0.1107 | 0.2243 | 2.0262 | 20.26 | | | | |
| 30% higher | 30 min | 0.1036 | 0.1056 | 0.2463 | 2.3324 | 23.32 | 17.3633 | | | |
| 30% higher | 30 min | 0.2257 | 0.1545 | 0.2548 | 1.6492 | 16.49 | | | | |
| 30% higher | 30 min | 0.2486 | 0.1975 | 0.2425 | 1.2278 | 12.28 | | | | |
| 10% lower | 30 min | 0.2859 | 0.0954 | 0.2555 | 2.6782 | 26.78 | 22.8267 | | | |
| 10% lower | 30 min | 0.1217 | 0.12 | 0.3136 | 2.6133 | 26.13 | | | | |
| 10% lower | 30 min | 0.3955 | 0.1297 | 0.202 | 1.5574 | 15.57 | | | | |
| 20% lower | 30 min | 0.3806 | 0.1136 | 0.254 | 2.2359 | 22.36 | 18.7033 | | | |
| 20% lower | 30 min | 0.2666 | 0.1149 | 0.1925 | 1.6754 | 16.75 | | | | |
| 20% lower | 30 min | 0.3167 | 0.1075 | 0.1828 | 1.7005 | 17 | | | | |
| 30% lower | 30 min | 0.3931 | 0.1031 | 0.2531 | 2.4549 | 24.55 | 20.2467 | | | |
| 30% lower | 30 min | 0.4278 | 0.1615 | 0.2365 | 1.4644 | 14.64 | | | | |
| 30% lower | 30 min | 0.1701 | 0.1014 | 0.2185 | 2.1548 | 21.55 | | | | |
| 40% lower | 30 min | 0.2957 | 0.0805 | 0.2067 | 2.5677 | 25.67 | 21.3167 | | | |
| 40% lower | 30 min | 0.3816 | 0.1069 | 0.188 | 1.7587 | 17.59 | | | | |
| 40% lower | 30 min | 0.3317 | 0.0905 | 0.1873 | 2.0696 | 20.69 | | | | |
| Plasma | 15 min | 0.3661 | 0.0844 | 0.1688 | 2.0000 | 20 | 22.3367 | | | |
| Plasma | 15 min | 0.2843 | 0.0741 | 0.1689 | 2.2794 | 22.79 | | | | |
| Plasma | 15 min | 0.3869 | 0.0898 | 0.2175 | 2.4220 | 24.22 | | | | |

The results reported for HC, LC and TC are density of reflectance (Dr). The results show that there was no obvious effect of the presence of RBC on the S/CO (S means signal; CO means cutoff). In any non-quantitative, i.e., qualitative assay, S/CO>1 means positive because the CO is determined HBsAg test cassette. Blood sample was applied on the sample filter at Port-2 for the HBsAg assay (as described in Example 7 above) and on the sample filter at port 1 for the HIV assay (as described in Example 3 above) and the assays were conducted as before. Results are shown in Tables 13 and 14.

TABLE 13

HIV Test (Conjugate coated by Bio-jet or Rinse)

| Coated | Sample | Volume | Background | HC Dr | LC Dr | TEST Dr | RI = TEST Dr/LC Dr | S/CO | AV S/CO |
|---|---|---|---|---|---|---|---|---|---|
| Rinse | HIV (+) | 50 μl | Clean | 0.1564 | 0.1785 | 0.1736 | 0.9725 | 9.7255 | Average |
| Rinse | Blood | 50 μl | Clean | 0.1458 | 0.1793 | 0.1806 | 1.0073 | 10.0725 | 9.614 |
| Rinse | | 50 μl | Clean | 0.1135 | 0.2106 | 0.2094 | 0.9943 | 9.943 | Standard |
| Rinse | | 50 μl | Clean | 0.1356 | 0.1883 | 0.1683 | 0.8938 | 8.9379 | Deviation |
| Rinse | | 50 μl | Clean | 0.1079 | 0.1872 | 0.1758 | 0.9391 | 9.391 | 0.457 |
| | | | | | | | | | CV 4.76% |
| Jet | | 50 μl | Clean | 0.1456 | 0.2281 | 0.2107 | 0.9237 | 9.2372 | Average |
| Jet | | 50 μl | Clean | 0.1175 | 0.1758 | 0.1658 | 0.9431 | 9.4312 | 9.456 |
| Jet | | 50 μl | Clean | 0.1334 | 0.1606 | 0.1708 | 1.0635 | 10.6351 | Standard |
| Jet | | 50 μl | Clean | 0.1238 | 0.2301 | 0.2152 | 0.9352 | 9.3525 | Deviation |
| Jet | | 50 μl | Clean | 0.1034 | 0.1898 | 0.1637 | 0.8625 | 8.6249 | 0.731 |
| | | | | | | | | | CV 7.7% |

TABLE 14

HBsAg Test (Conjugate coated by Bio-jet or Rinse)

| Jet | HC Dr | LC Dr | HBsAg Dr | RI = HBsAg Dr/HC Dr | ng/ml | Rinse | HC Dr | LC Dr | HBsAg Dr | RI = HBsAg Dr/HC Dr | ng/ml |
|---|---|---|---|---|---|---|---|---|---|---|---|
| 1 | 0.2153 | 0.1433 | 0.0153 | 0.0711 | 3.9 | 1 | 0.23 | 0.25 | 0.011 | 0.0478 | 2.6 |
| 2 | 0.1879 | 0.1163 | 0.0144 | 0.0766 | 4.3 | 2 | 0.31 | 0.33 | 0.019 | 0.0613 | 3.4 |
| 3 | 0.1759 | 0.1245 | 0.0167 | 0.0949 | 5.5 | 3 | 0.34 | 0.34 | 0.017 | 0.0500 | 2.5 |
| 4 | 0.1419 | 0.0845 | 0.0135 | 0.0951 | 5.5 | 4 | 0.26 | 0.29 | 0.013 | 0.0500 | 2.6 |
| 5 | 0.1985 | 0.1242 | 0.0176 | 0.0887 | 5.1 | 5 | 0.36 | 0.35 | 0.02 | 0.0556 | 3 |
| 6 | 0.202 | 0.1267 | 0.014 | 0.0693 | 3.8 | 6 | 0.35 | 0.34 | 0.017 | 0.0486 | 2.6 |
| 7 | 0.1898 | 0.1291 | 0.0152 | 0.0801 | 4.5 | 7 | 0.34 | 0.33 | 0.019 | 0.0559 | 3 |
| 8 | 0.1764 | 0.1456 | 0.0143 | 0.0811 | 4.6 | 8 | 0.43 | 0.36 | 0.021 | 0.0488 | 2.5 |
| 9 | 0.2306 | 0.1917 | 0.0206 | 0.0893 | 5.1 | 9 | 0.36 | 0.36 | 0.018 | 0.0500 | 2.6 |
| 10 | 0.192 | 0.1168 | 0.0139 | 0.0724 | 4 | 10 | 0.35 | 0.34 | 0.019 | 0.0543 | 2.9 |
| 11 | 0.1895 | 0.1219 | 0.017 | 0.0897 | 5.2 | 11 | 0.27 | 0.28 | 0.016 | 0.0593 | 3.1 |
| 12 | 0.2355 | 0.1692 | 0.021 | 0.0892 | 5.1 | 12 | 0.39 | 0.36 | 0.02 | 0.0513 | 2.7 |
| 13 | 0.2369 | 0.1589 | 0.0156 | 0.0659 | 3.6 | 13 | 0.38 | 0.35 | 0.019 | 0.0500 | 2.7 |
| 14 | 0.2041 | 0.1543 | 0.015 | 0.0735 | 4.1 | 14 | 0.32 | 0.29 | 0.013 | 0.0406 | 2.1 |
| 15 | 0.2294 | 0.1633 | 0.0175 | 0.0763 | 4.3 | 15 | 0.37 | 0.33 | 0.019 | 0.0514 | 2.7 |
| 16 | 0.1611 | 0.0947 | 0.0146 | 0.0906 | 5.2 | 16 | 0.32 | 0.28 | 0.014 | 0.0438 | 2.3 |
| 17 | 0.2204 | 0.1518 | 0.0218 | 0.0989 | 5.8 | 17 | 0.2 | 0.22 | 0.013 | 0.0650 | 3.6 |
| 18 | 0.1785 | 0.1272 | 0.0151 | 0.0846 | 4.8 | 18 | 0.33 | 0.27 | 0.017 | 0.0515 | 2.7 |
| 19 | 0.2607 | 0.1911 | 0.0231 | 0.0886 | 5.1 | 19 | 0.32 | 0.26 | 0.019 | 0.0594 | 3.1 |
| 20 | 0.1884 | 0.1161 | 0.0162 | 0.0860 | 4.9 | 20 | 0.28 | 0.3 | 0.015 | 0.0536 | 2.9 |
| AV | 0.2007 | 0.1376 | 0.0166 | 0.0831 | 4.72 | AV | 0.3255 | 0.3115 | 0.0170 | 0.0524 | 2.7800 |
| SD | 0.0289 | 0.0285 | 0.0028 | 0.0095 | 0.63 | SD | 0.0556 | 0.0417 | 0.0029 | 0.0058 | 0.3548 |
| CV | | | | 11.5% | 13.0% | CV | | | | 11.2% | 12.8% |

Dr stands for density of reflectance which is calculated the same way as optical density (OD), except Dr is for reflected light. Dr is the raw data generated by the ReLIA machine. The CV on the ng/ml result is the same for rinse and Biojet coated conjugate, so the testing accuracies are the same.

Example 10

Effect of Sample Volume on Assay

To determine the effect of sample volume on the accuracy of the present assay, the following experiment was conducted. Glass fiber element #142 pretreated with 0.25 mg/ml of rabbit anti-hRBC was used as the sample filter in Port-1. HIV-positive whole blood containing a RBC volume of 45.3% was used as sample in a HIV testing cassette. HBsAg-positive whole blood, having a hematocrit of 44%, was used as sample in an HBsAg testing cassette. Varying sample volumes were applied to the sample filter at Port-2. The assay was conducted as before. Briefly, the HIV assay with whole blood as sample was performed with the sample added to Port 1. The sample filter in port 1 consists of glass fiber element #142 pretreated with 0.25 mg/ml of rabbit anti-hRBC. After the sample had flowed down the strip and stopped, buffer was added to Port-2. Results are recorded in Table 15.

TABLE 15

Comparison of HIV Testing Results with Varying Volumes of a Blood Specimen

| Sample | Sample Vol. μl | Migration Rate mm/min | RBC remain | Back-ground on NC | HC Dr | LC Dr | TEST Dr | RI = TEST Dr/LC Dr | S/CO | Avg | CV | Test Time (min) |
|---|---|---|---|---|---|---|---|---|---|---|---|---|
| HIV (+) | 30 | □16 | No | Clean | 0.4752 | 0.226 | 0 | 0 | 0 | 0 | — | 20 |
| Blood | 30 | □16 | No | Clean | 0.4154 | 0.2432 | 0 | 0 | 0 | | | |
| | 30 | □16 | No | Clean | 0.4163 | 0.2317 | 0 | 0 | 0 | | | |
| | 40 | □16 | No | Clean | 0.2936 | 0.1979 | 0.2043 | 1.0323 | 10.3223 | 9.0592 | 12.9% | 20 |
| | 40 | □16 | No | Clean | 0.2697 | 0.1958 | 0.1731 | 0.8841 | 8.8396 | | | |
| | 40 | □16 | No | Clean | 0.2994 | 0.1986 | 0.1592 | 0.8016 | 8.0156 | | | |
| | 40 | □16 | No | Clean | 0.371 | 0.225 | 0.2507 | 1.1142 | 9.1408 | 9.5644 | 8.86% | 30 |
| | 40 | □16 | No | Clean | 0.1701 | 0.1983 | 0.209 | 1.054 | 10.5396 | | | |
| | 40 | □16 | No | Clean | 0.3206 | 0.1955 | 0.1762 | 0.9013 | 9.0128 | | | |
| | 50 | ≦16 | (+/−) | Clean | 0.2037 | 0.1697 | 0.2164 | 1.2752 | 12.7513 | 12.0134 | 6.5% | 30 |
| | 50 | ≦16 | (+/−) | Clean | 0.2572 | 0/.1876 | 0.2271 | 1.2106 | 12.1034 | | | |
| | 50 | ≦16 | (+/−) | Clean | 0.0603 | 0.1729 | 0.1934 | 1.1186 | 11.1856 | | | |
| | 60 | □16 | (+) | Clean | 0.3271 | 0.2474 | 0.2005 | 0.8104 | 8.105 | 9.8273 | 20.42% | 30 |
| | 60 | □16 | (+) | Clean | 0.3456 | 0.1984 | 0.2387 | 1.2031 | 12.0302 | | | |
| | 60 | □16 | (+) | Clean | 0.1926 | 0.246 | 0.2299 | 0.9346 | 9.3467 | | | |
| | 70 | □16 | (+) | Clean | 0.1296 | 0.1983 | 0.1913 | 0.9647 | 9.649 | 9.6556 | 8.4% | 30 |
| | 70 | □16 | (+) | Clean | 0.1387 | 0.245 | 0.2168 | 0.8849 | 8.8477 | | | |
| | 70 | □16 | (+) | Clean | 0.1119 | 0.2401 | 0.2514 | 1.0471 | 10.4702 | | | |

In this HIV testing experiment, sample volumes of from 30 μl up to 70 μl were used. The 30 μl sample volume did not generate any readable test results, while sample volumes higher than 30 μl did. For the 40 μl samples, for example, readable results were obtained regardless of whether the test was conducted for 20 min. or 30 min. The background on the NC element was clean for all the sample volumes applied. Thus, a 40 μl sample volume is sufficient for running this assay, but results are not significantly different at sample sizes of 50, 60, or 70 μl.

TABLE 16

Comparison of varying specimen volume in an HBsAg Test at Different Assay Times. Assays were run in triplicate

| | | | Testing results | | | | | | | | |
|---|---|---|---|---|---|---|---|---|---|---|---|
| Whole | | Plasma | 20 min | | | 30 min | | | 40 min | | |
| Blood (μl) | RBC Leaking | Migrate (mm/min) | RBC remained | HBsAg (ng/ml) | CV % | RBC remained | HBsAg (ng/ml) | CV % | RBC remained | HBsAg (ng/ml) | CV % |
| 150 | No | >16 mm | (+/−) | 3.2 | 42% | (−) | 3.94 | 42 | (−) | 4.1 | 46% |
| 200 | No | >16 mm | (+) | 3.28 | 9% | (+/−) | 3.46 | 3 | (−) | 3.27 | 19% |
| 250 | No | >16 mm | (++) | 2.63 | 6% | (+) | 2.77 | 6 | (+/−) | 2.75 | 4% |
| 300 | No | >16 mm | (+++) | 2.77 | 6% | (++) | 2.83 | 9 | (++) | 3.13 | 10% |
| Plasma 150 ul | | | 30 min 3.36 | | | | | CV % 5% | | | |

Results from HBsAg testing showed that using a sample volume of 150 μl resulted in a high CV %. At sample volumes greater than 150 μl, such as 200 μl, 250 μl, or 300 μl, the CV % were low, in the range of 6%-9% for the 20 min. assay, 3%-9% for the 30 min. assay and 4%-19% for the 40 min. assay. For the 250 μl sample volume, the CV % was low, in the range of in 4%-6% at the 20 min., 30 min. or 40 min. assay times. Thus, a 250 μl sample volume is sufficient for running this assay, but results are not significantly different at sample sizes of 200, 250, or 300 μl if the assay is run for either 20 or 30 minutes. The CV was higher (19%) for the 200 μl assay if the assay was carried out for 40 minutes rather than 20 or 30 minutes.

With respect to ranges of values, the invention encompasses each intervening value between the upper and lower limits of the range to at least a tenth of the lower limit's unit, unless the context clearly indicates otherwise. Moreover, the invention encompasses any other stated intervening values and ranges including either or both of the upper and lower limits of the range, unless specifically excluded from the stated range.

Unless defined otherwise, the meanings of all technical and scientific terms used herein are those commonly understood by one of ordinary skill in the art to which this invention belongs. One of ordinary skill in the art will also appreciate that any methods and materials similar or equivalent to those described herein can also be used to practice or test this invention.

The publications and patents discussed herein are provided solely for their disclosure prior to the filing date of the present application. Nothing herein is to be construed as an admission that the present invention is not entitled to antedate such publication by virtue of prior invention. Further the dates of publication provided may be different from the actual publication dates which may need to be independently confirmed.

All the publications cited are incorporated herein by reference in their entireties, including all published patents, patent applications, literature references, as well as those publications that have been incorporated in those published documents. However, to the extent that any publication incorporated herein by reference refers to information to be published, applicants do not admit that any such information published after the filing date of this application to be prior art.

As used in this specification and in the appended claims, the singular forms include the plural forms. For example the terms "a," "an," and "the" include plural references unless the content clearly dictates otherwise. Hence, unless otherwise indicated, reference to "a sample filter," includes one or more sample filters. Optionally, a buffer pad can be situated above any sample filter or assemblage of sample filters. This applies to all embodiments described below.

All alternatives described above in terms of the general format, such as the placement of absorbers, the use or omission of a sample filter or its replacement with a sample pad, the use or omission of agglutinating agents, the replacement of hydrophobic elements such as elements with hydrophilic elements, the placement of detectable agents in a conjugate pad or in the test strip itself, or the omission of the detectable agent from the test strip, the use or omission of buffer pads, or the placement of conjugate pads, can be applied to the specific formats, such as those of FIG. 2, 3, 3A, 3B, 4, 4A, 4B, 8, 9, 10, 11, 12, or 13 as long as such alternatives are consistent with the configurations of those specific formats. Additionally, the term "at least" preceding a series of elements is to be understood as referring to every element in the series. Those skilled in the art will recognize, or will be able to ascertain using no more than routine experimentation, many equivalents to the specific embodiments of the invention described. Such equivalents are intended to be encompassed by the following claims.

REFERENCES

Fu, G. et al. (2004). Purification and characterization of the human erythrocyte band 3 protein C-terminal domain. *Biochemistry* 43(6) 1633-8.

Wang, D. N. (1994). Band 3 protein: structure, flexibility and function. *FEBS Lett.* 346(1): 26-31.

Young, M. T. and Tanner, M. J. (2003). Distinct regions of human glycophorin A enhance human red cell anion exchanger (Band 3; AE1) transport function and surface trafficking. *J. Biol. Chem.* 278(35): 32954-61. Epub 2003 Jun. 17.

We claim:

1. A test strip for conducting a lateral flow assay for detection of at least one analyte in a sample, comprising:
   (a) a chromatographic strip comprising a first end and a second end;
   (b) at least one capture band, wherein the one capture band is a first capture band, and is located on the chromatographic strip, and wherein the first capture band comprises a first immobilized capture agent for capturing a first analyte in the sample;
   (c) optionally, a second capture band that is located on the chromatographic strip, wherein the second capture band comprises a second immobilized capture agent for capturing a second analyte in the sample;
   (d) at least one control band optionally comprising an immobilized control agent;
   (e) at least one sample filter, wherein the one sample filter is a first sample filter, and wherein the first sample filter is in capillary contact with the chromatographic strip, and optionally comprises an agglutinating agent;
   (f) a fluid-impermeable barrier, wherein the barrier is in capillary contact with at least the first sample filter and the chromatographic strip and slows fluid flow from the first sample filter to the chromatographic strip;
   (g) at least one mobilizable detectable agent, wherein the one mobilizable detectable agent is a first mobilizable detectable agent that is capable of binding to the first analyte or to a first capture agent or to a complex formed by the combination of the first analyte and the first capture agent, wherein the first mobilizable detectable agent is provided on the chromatographic strip or can be released onto the chromatographic strip;
   (h) optionally, a backing that supports the test strip;
   (i) a first absorbent pad, that is in capillary contact with the chromatographic strip;
   (j) optionally, a second absorbent pad that is in capillary contact with the first absorbent pad;
   wherein the test strip allows detection with or without quantitation of an analyte in a sample containing whole cells.

2. The test strip of claim 1, wherein the mobilizable detectable agent is provided in a conjugate pad that is in capillary contact with the chromatographic strip.

3. The test strip of claim 2, wherein the conjugate pad retains the mobilizable detectable agent until fluid is added to the conjugate pad to release the mobilizable detectable agent.

4. The test strip of claim 1, further comprising a conjugate pad that is in capillary contact with the chromatographic strip; a second sample filter that is in capillary contact with the chromatographic strip and optionally comprises an agglutinating agent; and a fluid collector, wherein the fluid collector is in capillary contact or direct physical contact with (a) the second sample filter and the conjugate pad or (b) the second sample filter and the chromatographic strip.

5. The test strip of claim 1, further comprising a buffer pad that is located at or near the second end of the chromatographic strip.

6. The test strip of claim 1, further comprising a sample filter that is located at or near the second end of the chromatographic strip.

7. The test strip of claim 1, wherein the first absorbent pad is located at or near the first end of the chromatographic strip.

8. The test strip of claim 1, further comprising a conjugate pad that is located at or near the second end of the chromatographic strip.

9. The test strip of claim 1, wherein the fluid-impermeable barrier comprises a tape, optionally, a double-sided tape.

10. The test strip of claim 1, wherein the fluid-impermeable barrier is (a) completely under the first sample filter or (b) is partially under the first sample filter and is extended in the direction of the first end.

11. The test strip of claim 1, wherein the fluid-impermeable barrier is about 5 mm wide, about 5 mm to about 10 mm long and about 2.5 mm thick.

12. The test strip of claim 1, wherein the fluid-impermeable barrier is a double-sided tape made of polyester and is optionally coated with adhesive on one or both sides.

13. The test strip of claim 12, wherein the adhesive, if present, is an inert, non-migratory acrylic adhesive.

14. The test strip of claim 1, further comprising a conjugate pad, and a buffer pad, wherein the conjugate pad and the buffer pad are both at, or near, the second end, and the first sample filter, the first absorbent pad and the second absorbent pad, if present, are at, or near, the first end.

15. The test strip of claim 1, wherein the test strip further comprises a second sample filter, a fluid collector and a conjugate pad, and wherein:
   (a) each of the first and second sample filters optionally comprises an agglutinating agent, and each of the first and second sample filters is in capillary contact with the chromatographic strip, the first sample filter being located at, or near, the first end of the chromatographic strip and the second sample filter being located near the second end of the chromatographic strip;
(b) the fluid collector is located between the second sample filter and the chromatographic strip, and is in capillary contact with both the second sample filter and the chromatographic strip;
(c) the conjugate pad is located at, or near, the second end of the chromatographic strip and is in capillary contact with the second sample filter and the fluid collector;
(d) the fluid-impermeable barrier is in direct physical contact with the first end of the chromatographic strip and is located under the first sample filter, where fluid flow from the first sample filter in the direction of the first end of the chromatographic strip is substantially slowed by forcing the fluid to flow underneath the impermeable barrier to reach the first end of the strip;
(e) the first absorbent pad is located at, or near, the first end of the chromatographic strip and is in direct physical contact with the chromatographic strip, wherein, the first absorbent pad is located closer to the first end of the chromatographic strip than the first sample filter; and
(f) the second absorbent pad, if present, is in capillary contact with the first absorbent pad or the chromatographic strip.

16. The test strip of claim 1, wherein the test strip further comprises a second sample filter that is in capillary contact with the chromatographic strip, a fluid collector, and a conjugate pad, and wherein:
(a) the fluid collector is located between the second sample filter and the chromatographic strip, and is in direct physical contact with both the second sample filter and the chromatographic strip;
(b) the conjugate pad is located at the second end of the chromatographic strip and is in direct physical contact with the second sample filter and indirect contact with the fluid collector; and
(c) the fluid-impermeable barrier is in direct physical contact with the first sample filter and the chromatographic strip at, or near, the first end, wherein fluid flow from the first sample filter in the direction of the first end of the chromatographic strip is substantially slowed by forcing the fluid to flow underneath the impermeable barrier to reach the first end of the strip.

17. A test strip for conducting a lateral flow assay for detection of at least one analyte in a sample, comprising:
(a) a chromatographic strip comprising a first end and a second end, at least one capture band comprising an immobilized capture agent for capturing the at least one analyte, and at least one control band comprising an immobilized control agent;
(b) a conjugate pad, wherein the conjugate pad is in capillary contact with the second end of the chromatographic strip, and wherein the conjugate pad comprises a mobilizable detectable agent that is capable of binding to the at least one analyte or to the capture agent after capturing the analyte;
(c) a fluid-impermeable barrier in direct contact with the first end of the chromatographic strip;
(d) a sample filter, wherein the sample filter is in capillary contact with the first end of the chromatographic strip and is in direct contact with the fluid-impermeable barrier such that flow from the sample filter in the direction of the first end of the chromatographic strip is substantially delayed, and wherein the sample filter optionally comprises an agglutinating agent;
(e) optionally, a buffer pad that is located at the second end of the chromatographic strip and is in direct contact with the conjugate pad;
(f) a first absorbent pad located at the first end of the chromatographic strip that is in direct contact with the chromatographic strip; and
(g) optionally, a second absorbent pad that is in direct contact with the first absorbent pad;
wherein the test strip allows detection with or without quantitation of an analyte in a sample containing whole cells.

18. A test strip for conducting a lateral flow assay for detection of at least one analyte in a sample, comprising:
(a) a chromatographic strip comprising a first end and a second end, at least one capture band comprising an immobilized capture agent for capturing the at least one analyte, and at least one control band comprising an immobilized control agent;
(b) a conjugate pad, wherein the conjugate pad is in direct capillary contact with the second end of the chromatographic strip, and wherein the conjugate pad comprises a mobilizable detectable agent that is capable of binding to the at least one analyte or to the capture agent after capturing the analyte;
(c) first and second sample filters, wherein each of the first and second sample filters optionally comprises an agglutinating agent, and each of the first and second sample filters is in capillary contact with the chromatographic strip, the first sample filter being located at, or near, the first end of the chromatographic strip and the second sample filter being located adjacent to the second end of the chromatographic strip;
(d) a fluid collector that is located between the second sample filter and the conjugate pad such that it is in direct contact with both the second sample filter and the conjugate pad;
(e) a fluid-impermeable barrier in direct contact with the first sample filter and the chromatographic strip at, or near, the first end such that flow from the first sample filter in the direction of the first end of the chromatographic strip is substantially delayed;
(f) a first absorbent pad located at the first end of the chromatographic strip that is in direct contact with the chromatographic strip, the first absorbent pad being located closer to the first end of the chromatographic strip than the first sample filter; and
(g) optionally, a second absorbent pad that is in direct contact with the first absorbent pad;
wherein the test strip allows detection with or without quantitation of an analyte in a sample containing whole cells.

19. A test strip for conducting a lateral flow assay for detection of at least one analyte in a sample, comprising:
(a) a chromatographic strip comprising a first end and a second end, at least one capture band comprising an immobilized capture agent for capturing the at least one analyte, and at least one control band comprising an immobilized control agent;
(b) first and second sample filters, wherein each of the first and second sample filters optionally comprises an agglutinating agent, and each of the first and second sample filters is in capillary contact with the chromatographic strip, the first sample filter being located at, or near, the first end of the chromatographic strip and the second sample filter being located adjacent to the second end of the chromatographic strip;
(c) a fluid collector that is located between the second sample filter and the chromatographic strip such that it is in direct contact with both the second sample filter and the chromatographic strip;
(d) a conjugate pad located at the second end of the chromatographic strip and that is in direct contact with the second sample filter and indirect contact with the fluid collector, and wherein the conjugate pad comprises a mobilizable detectable agent that is capable of binding to the at least one analyte or to the capture agent after capturing the analyte;
(e) a fluid-impermeable barrier in direct contact with the first sample filter and the chromatographic strip at, or near, the first end such that flow from the first sample filter in the direction of the first end of the chromatographic strip is substantially delayed;
(f) a first absorbent pad located at the first end of the chromatographic strip that is in direct contact with the chromatographic strip, the first absorbent pad being located closer to the first end of the chromatographic strip than the first sample filter; and
(g) optionally, a second absorbent pad that is in direct contact with the first absorbent pad;
wherein the test strip allows detection with or without quantitation of an analyte in a sample containing whole cells.

20. The test strip of claim 19, wherein each of the conjugate pad, second sample filter, and fluid collector can be offset so that the conjugate pad partially overlaps the second sample filter and the second sample filter partially overlaps the fluid collector, or the conjugate pad can partially overlap the second sample filter, and the second sample filter substantially overlaps the fluid collector.

21. The test strip of claim 1, wherein the mobilizable detectable agent comprises an antibody, an antigen, colored material, a label or a particle.

22. The test strip of claim 21, wherein the label comprises a colloidal particle label, a fluorescent label, a chemiluminescent label, a bioluminescent label, a redox label, a radiofrequency label, a quantum dot conjugate; an enzyme label, a radioactive label, or a combination thereof.

23. The test strip of claim 22, wherein the colloidal particle label comprises colloidal gold particles, colloidal sulfur particles, colloidal selenium particles, colloidal barium sulfate particles, colloidal iron sulfate particles, colloidal metal iodate particles, colloidal silver halide particles, colloidal silica particles, or colloidal metal (hydrous) oxide particles.

24. The test strip of claim 22, wherein the colloidal particle label comprises a colloidal gold label.

25. The test strip of claim 21, wherein the mobilizable detectable agent is coupled to an analyte nonspecific agent, optionally, a control binding agent.

26. The test strip of claim 1, wherein the chromatographic strip comprises a nitrocellulose element.

27. The test strip of claim 1, wherein the first analyte or the second analyte, if present, comprises an antigen, an antibody, a hormone, a drug, a cell protein, a DNA, a cardiac marker, a tumor marker, a ligand, a receptor or an autoimmune disease marker.

28. The test strip of claim 1, wherein the chromatographic strip comprises at least two control bands.

29. The test strip of claim 1, comprising a backing, wherein the backing comprises a liquid impermeable material.

30. The test strip of claim 1, wherein the chromatographic strip comprises a high capacity protein binding element.

31. The test strip of claim 1, wherein:
(a) the sample contains two analytes and the chromatographic strip comprises two capture bands, each capture band comprising an immobilized capture agent that is specific for capturing one analyte but not the other, or
(b) the sample contains three analytes and the chromatographic strip comprises three capture bands, each capture band comprising an immobilized capture agent that is specific for capturing one analyte but not the other two.

32. A cassette comprising the test strip of claim 1.

33. The cassette of claim 32, wherein the cassette can be read in a device, optionally, in a device that measures reflectance.

34. The cassette of claim 32, wherein the cassette comprises a Port-1 and a Port-2 for application of sample and/or buffer.

35. A method of conducting a lateral flow assay for detection or determination of an analyte in a sample containing a fluid comprising the steps of:
(a) applying a first aliquot of the sample to the sample filter of the test strip of claim 1;
(b) causing the fluid from the sample to migrate to the first capture band;
(c) causing the first detectable agent to migrate to the first capture band;
(d) causing the first detectable agent, the analyte from the fluid from the first aliquot and the first capture band to interact; and
(e) detecting or determining the first detectable agent at the first capture band.

36. The method of claim 35, wherein the detection or determination of the first detectable agent is correlated with an amount of the analyte.

37. The method of claim 35, wherein the first detectable agent is detected or determined by an optical reflectance measurement, by fluorescence or by chemiluminescence.

38. The method of claim 35, wherein the sample contains blood cells.

39. The method of claim 35, further comprising the step of detecting or determining a second or a third detectable agent at a second or a third capture band.

* * * * *